US006451315B1

(12) United States Patent
Reed et al.

(10) Patent No.: US 6,451,315 B1
(45) Date of Patent: Sep. 17, 2002

(54) COMPOUNDS AND METHODS FOR THE DIAGNOSIS AND TREATMENT OF *B. MICROTI* INFECTION

(75) Inventors: Steven G. Reed, Bellevue; Michael J. Lodes, Seattle; Raymond L. Houghton, Bothell; Paul R. Sleath, Seattle; Patricia D. McNeill, Des Moines, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/528,784

(22) Filed: Mar. 17, 2000

Related U.S. Application Data

(63) Continuation-in-part of application No. 09/286,488, filed on Apr. 5, 1999, which is a continuation-in-part of application No. 08/990,571, filed on Dec. 11, 1997, now Pat. No. 6,214,971, which is a continuation-in-part of application No. 08/845,258, filed on Apr. 24, 1997, now Pat. No. 6,183,976, which is a continuation-in-part of application No. 08/723,142, filed on Oct. 1, 1996, now Pat. No. 6,306,396.

(51) Int. Cl.$^7$ .................... A61K 39/002; A61K 39/015; C07K 14/44; C07K 1/00; G01N 33/569
(52) U.S. Cl. ............................... 424/191.1; 424/184.1; 424/185.1; 424/192.1; 424/265.1; 424/270.1; 435/7.22; 435/7.1; 435/69.3; 435/69.7; 435/71.1; 530/350; 530/822; 514/44
(58) Field of Search .......................... 424/184.1, 185.1, 424/191.1, 192.1, 265.1, 270.1; 514/44; 530/350, 822, 7.22; 435/69.7, 71.1, 7.1, 69.3

(56) References Cited

U.S. PATENT DOCUMENTS

| | | | |
|---|---|---|---|
| 4,879,213 A | 11/1989 | Fox et al. | |
| 5,171,685 A | 12/1992 | McElwain et al. | |
| 5,837,545 A | 11/1998 | Guy et al. | |

FOREIGN PATENT DOCUMENTS

| | | |
|---|---|---|
| EP | 018 579 A | 11/1990 |
| EP | 0834 567 A | 4/1998 |
| WO | WO 90/11776 | 10/1990 |
| WO | WO 99/29869 | 6/1999 |

OTHER PUBLICATIONS

Plotkin et al., *Vaccines*, W.B. Saunders Company, Philadelphia, 1988, Chapter 29, p. 571 ($2^{nd}$ full paragraph).
Rudinger et al., *Peptide Hormones*, University Park Press, Baltimore, MD, 1976, Ch. I, "Characteristics of the Amino Acids as Components of a Peptide Hormone Sequence," pp. 1–7.

Tetzlaff et al., "Isolation and Characterization of a Gene Associated with a Virulent Strain o *Babesia microti*," *Molecular and Biochemical Parasitology* 40:183–192, 1990.
Burgess et al., "Possible Dissociation of the Heparin–Binding and Mitogenic Activities of Heparin–Binding (Acidic Fibroblast) Growth Factor–1 from its Receptor–Binding Activities by Site–Directed Mutagenesis of a Single Lysine Residue," *The Journal of Cell Biology* 111:2129–2138, 1990.
Cox et al., "Antibody Levels in Mice Infected with *Babesia microti*," *Ann. Trop. Med. Parasitol* 64(2):167–173, 1970.
Foglino et al., "Nucleotide Sequence of the pepN Gene Encoding Aminopeptidase N of *Escherichia coli*," *Gene* 49:303–309, 1986.
Herwaldt et al., "A Fatal Case of Babesiosis in Missouri: Identification of Another Piroplasm that Infects Humans," *Ann International Med.* 124(7):643–650, 1996.
Krause et al., "Comparison on PCR with Blood Smear and Inoculatio of Small Animals for Diagnosis of *Babesia microti* Parasitemia," *J. Clinical Microbiology* 34(11):2791–2794,1996.
Lazar et al., "Transforming Growth Factor α: Mutation of Aspartic Acid 47 Leucine 48 Results in Different Biological Activities," *Molecular and Cellular Biology* 8(3):1247–1252, 1988.
Levinson et al. (ed.), *Medical Microbiology & Immunology*, $3^{rd}$ ed., Prentice Halll, Englewood Cliffs, NJ, 1998, pp. 292–293.
McCaman and Gabe, "The Nucleotide Sequence of the pepN Gene and it Over–Expression in *Escherichia Coli*," *Gene* 48:145–153, 1986.

*Primary Examiner*—Lynette R. F. Smith
*Assistant Examiner*—Padma Baskar
(74) *Attorney, Agent, or Firm*—Seed Intellectual Property Law Group PLLC

(57) ABSTRACT

Compounds and methods for the diagnosis and treatment of *B. microti* infection are disclosed. The compounds provided include polypeptides that contain at least one antigenic portion of a *B. microti* antigen, DNA sequences encoding such polypeptides, and fusion proteins comprising such polypeptides. Antigenic epitopes of such antigens are also provided, together with pharmaceutical compositions and vaccines comprising such polypeptides, DNA sequences, fusion proteins or antigenic epitopes. Diagnostic kits containing such polypeptides, DNA sequences, fusion proteins or antigenic epitopes and a suitable detection reagent may be used for the detection of *B. microti* infection in patients and biological samples. Antibodies directed against such polypeptides and antigenic epitopes are also provided.

4 Claims, 9 Drawing Sheets

```
AACTAGATGCAGCACCACAATCACTACCACGTACCAATCATATACCAATAATGTACTAATAATGTACCAATAACTATGGTTTATAAAGATGGTGTCATTTAAATCAATATTAGTTCCTTATATTA  125
                                                                              M  V  S  F  K  S  I  L  V  P  Y  I

CACTCTTTTTAATGAGCGGTGCTGTCTTTGCAAGTGATACCGATCCCGAAGCTGGTGGGCCTAGTGAAGCTGGTGGGCCTAGTGGAACTGTTGGGCCCAGTGAAGCTGGTGGGCCTAGTGAAGCT  250
                                                              Repeat Sequences
 T  L  F  L  M  S  G  A  V  F  A  S  D  T  D  P  E  A  G  G  P  S  E  A  G  G  P  S  G  T  V  G  P  S  E  A  G  G  P  S  E  A GGTGGGCCTAGTGGAACTGGTTGGCCTAGTGAAGCTGGTGGGCCTAGTGAAGCTGGTGGGCCTAGTGAAGCTGGTGGGCCTAGTGAAGCTGGTGGGCCTAGTGAACTGGTTGGCCTAGTGGAAC  375
                                                        Repeat Sequences
 G  G  P  S  G  T  G  W  P  S  E  A  G  G  P  S  E  A  G  G  P  S  E  A  G  G  P  S  E  A  G  G  P  S  G  T  G  W  P  S  G  T TGGTTGGCCTAGTGAAGCTGGTTGGTCTAGTGAACGATTTGGATATCAGCTTCTTCCGTATTCTAGAAGAATAGTTATATTTAATGAAGTTTGTTTATCTTATATATACAAACATAGTGTTATGA  500
       Repeat Sequences
 G  W  P  S  E  A  G  W  S  S  E  R  F  G  Y  Q  L  L  P  Y  S  R  R  I  V  I  F  N  E  V  C  L  S  Y  I  Y  K  H  S  V  M TATTGGAACGAGATAGGGTGAACGATGGTCATAAAGACTACATTGAAGAAAAAACCAAGGAGAAGAATAAATTGAAAAAAGAATTGGAAAAATGTTTTCCTGAACAATATTCCCTTATGAAGAAA  625

I  L  E  R  D  R  V  N  D  G  H  K  D  Y  I  E  E  K  T  K  E  K  N  K  L  K  K  E  L  E  K  C  F  P  E  Q  Y  S  L  M  K  K

GAAGAATTGGCTAGAATATTTGATAATGCATCCACTATCTCTTCAAAATATAAGTTATTGGTTGATGAAATATCAAACAAGGCCTATGGTACATTGGAAGGTCCAGCTGCTGATAATTTTGACCA  750

E  E  L  A  R  I  F  D  N  A  S  T  I  S  S  K  Y  K  L  L  V  D  E  I  S  N  K  A  Y  G  T  L  E  G  P  A  A  D  N  F  D  H

TTTCCGTAATATATGGAAGTCTATTGTACTTAAAGATATGTTTATATATTGTGACTTATTATTACAACATTTAATCTATAAATTCTATTATGACAATACCGTTAATGATATCAAGAAAAATTTTG  875

F  R  N  I  W  K  S  I  V  L  K  D  M  F  I  Y  C  D  L  L  L  Q  H  L  I  Y  K  F  Y  Y  D  N  T  V  N  D  I  K  K  N  F

ACGAATCCAAATCTAAAGCTTTAGTTTTGAGGGATAAGATCACTAAAAAGGATGGAGATTATAACACTCATTTTGAGGACATGATTAAGGAGTTGAATAGTGCAGCAGAAGAATTTAATAAAATT  1000

D  E  S  K  S  K  A  L  V  L  R  D  K  I  T  K  K  D  G  D  Y  N  T  H  F  E  D  M  I  K  E  L  N  S  A  A  E  E  F  N  K  I

GTTGACATCATGATTTCCAACATTGGGGATTATGATGAGTATGACAGTATTGCAAGTTTCAAACCATTTCTTTCAATGATCACCGAAATCACTAAAATCACCAAAGTTTCTAATGTAATAATTCC  1125

V  D  I  M  I  S  N  I  G  D  Y  D  E  Y  D  S  I  A  S  F  K  P  F  L  S  M  I  T  E  I  T  K  I  T  K  V  S  N  V  I  I  P

TGGAATTAAGGCACTAACTTTAACCGTTTTTTTAATATTTATTACAAAATAGATGTAATACCAGATGTATACATTATTATATATTACAAAATTTACACATTATTTATGTATGAACGAACGAACAT  1250

```
CTCAGTCTTAAATGAAGAAATTGGGATAAATATGGAAATAGATTAAAGTAACATGAGAAAGATGAATATAATATTAGAATATGAAATTTAACAGAAATAAAATGAAGTAAAAGAGTGTATTTTGT    1375

AATAATTTATAATAAATTAGTATACAATGATTATATTACAGATGACTATTGATTATTGTATCAATTAAATATTGATTATTAATGATATCATATATGTATATGTTAATGATTGATTTGTTATACGT    1500

TGTGAATATGTTATATAATGACATACTATAATAATTAATATAATGTAGAGGATATTTTTTTTAATAGTATTTAATGAATATTATAGTTATAATTATAATAATGTAGATAAAAATGACATTAATTT    1625

GAATGTTTAAATTGAAATGTATGTAAAAATATGTATTTATAATCTGAATTGATTAATAATATAATATTCTACAATTAATTATTTTTGTAATTATAATAATTGATTATATTAATCTTTGAATTATT    1750

ATAAATAATATTATACTTCATTAAATTATTTCACATAAATTTCCAAATTATTATCCTTTATCTTAATGTTATCCAATTTTACACATCTTTCTTCATTACAATATTTTTTACTAATCCTGTATGC    1875

TCATATTCATATTCTTTAGAAATATAACGAAAATTAGATGTAACTTCGCCACTTACAAGTAAACTACCATCAATATAATAATAATGAATACCATTCATGTCCGTATATTCTTTATATTTTTTATC    2000

ATATTTTATTTTGTGATTATTCCATTCATTTGTATCATTATTCAATGAGAGAAATAATAGCAGAAAGATCCTTCTATAGAAACATAAAATTCAATTAATACTGGATTATTATGTTTGCAAGTATA    2125

GATGTTTAAATCAATAACACTACCAGTTGGTAATTTAGCATTGTCATCAAATTCAATTATATAATCAGAAATTTTGATTTTATCAATTTTATTCGGATGTGATAATTTATTTTGTTCTGATTCAT    2250

CGATCATGTATACAAATACTATTGTTAAAGGTTCCCTATCCTTATAATTAAAGTGGCCAATAAGATTGGCATTAATTACATTAGTAGTGTGTATTTGTAATAGTATCATTAGTGGTACTGACA    2375

GTTGTTATAGGTTTTGATTTCCATAATGAAACATCATTTTTATCTACACAATACA    2430
```

*Fig. 1B*

```
BI254    .......... ..AGDTDREA GGPSGTVGP. .......... ..........
BI1053   .......... ...GDTDREA GGPSGTVGP. .......... ..........
BI2227   .......... ..AGDTDREA GGPSGTVGP. .......... .SEAGGPSEA
BI2259   .......... ..AGDTDREA GGPSGTVGP. .......... .SEAGGPSEA
BI2253   .......... ........EA GGPSGTVGP. .......... .SEAGGPSEA
GRAC,S   .......... ...GDTDREA GGPSGTVGP. .....SEAGG PSEAGGPSEA
FISH,S   .......... ..AGDTDREA GGPSGTVGPS SAGGPSEAGG PSEAGGPSEA
MN1HAM   .......... ..AGDTDREA GGPSGTVGP. .......... .......SEA
MN2      .......... ..AGDTDREA GGPSGTVGP. .......... ..........
MN1PAT   .......... ..AGDTDREA GGPSGTVGP. .......... .......SEA
Bmni-6   YITLFLMSGA VFAGDTDREA GGPSGTVGP. .......... .......SEA
MN3      .......... ..AGDTDREA GGPSGTVGP. .......... .SEAGGPSEA
MR.T     .......... ..AGDTDREA GGPSGTVGP. .......... .SEAGGPSEA
         51                                                 100
BI254    ...SEAGGPS EAGGPSGTVG PSEAGGPSEA GGPSGTGWPS EAGGPSGTVG
BI1053   ...SEAGGPS EAGGPSGTVG PSEAGGPSEA GGPSGTGWPS EAGGPSGTVG
BI2227   GGPSEAGGPS EAGGPSEAGG PSEAGGPSEA GGPSEAGGPS EAGGPSEAGW
BI2259   GGPSEAGGPS EAGGPSEAGG PSEAGGPSEA GGPSEAGGPS EAGGPSEAGW
BI2253   GGPSEAGGPS EAGGPSEAGG PSEAGGPSEA GGPSEAGGPS EAGGPSEAGW
GRAC,S   GGPSEAGGPS EAGGPSEAGG PSEAGGPSEA GGPSEAGGPS EAGGPSEAGW
FISH,S   GGPSEAGGPS EAGGPSEAGG PSEAGGPSEA GGPSEAGGPS EAGGPSEAGW
MN1HAM   GGPSEAGGPS EAGGPSEAGG PSEAGGPSEA GGPSEAGGPS EAGGPSGTGW
MN2      ...SEAGGPS EAGGPSEAGG PSEAGGPSEA GGPSEAGGPS EAGGPSGTGW
MN1PAT   GGPSEAGGPS EAGGPSEAGG PSEAGGPSEA GGPSEAGGPS EAGGPSGTGW
Bmni-6   GGPSEAGGPS EAGGPSEAGG PSEAGGPSEA GGPSHAGGPS EAGGPSGTGW
MN3      GGPSEAGGPS EAGGPSEAGG PSEAGGPSEA GGPSEAGGPS EAGGPSGTGW
MR.T     GGPSEAGGPS EAGGPSEAGG PSEAGGPSEA GGPSEAGGPS EAGGPSGTGW
         101                                                150
BI254    PSEAGGP... .........S EAGGPSGTGW PSGTGWPSEV GWPSERFGYQ
BI1053   PSEAGGP... .........S EAGGPSGTGW PSGTGWPSEV GWPSERFGYQ
BI2227   PSEAGWPSEA GGPSGTGWPS EAGWPSEAGW PSEAGWPSEA GW........
BI2259   PSEAGWPSEA GGPSGTGWPS EAGWPSEAGW PSEAGWPSEA GWPSERFGYQ
BI2253   PSEAGWPSEA GGPSGTGWPS EAGWPSEAGW PSEAGWPSEA GWPSER....
GRAC,S   PSEAGWPSEA GGPSGTGWPS EAGWPSEAGW PSEAGWPSEA GWPSERFGYQ
FISH,S   PSEAGWPSEA GGPSGTGWPS EAGWPSEAGW PSEAGWPSEA GWPSERFGYQ
MN1HAM   PSEAGWP... .........S EAGWPSEAGW PSEAGWPSEA GWPSERFGYQ
MN2      PSEAGWP... .........S EAGWPSEAGW PSEAGWPSEA GW........
MN1PAT   PSEAGWP... .........S EAGWPSEAGW PSEAGWPSEA GWPSERFGYO
Bmni-6   PSEAGWP... .........S EAGWPSEAGW PSEAGWPSEA GWPSERFGYQ
MN3      PSEAGWP... .........S EAGWPSEAGW PSEAGWPSEA GWPSERFGYQ
MR.T     PSEAGWP... .........S EAGWPSEAGW PSEAGWPSEA GWPSERFGYQ
```

*Fig. 6A*

|         | 151        | 177       |            |
|---------|------------|-----------|------------|
| BI254   | LLWYSRRIVI | .......... | ....... |
| BI1053  | LLWYSRRIVI | .......... | ....... |
| BI2227  | .......... | .......... | ....... |
| BI2259  | LLWYSRRIVI | .......... | ....... |
| BI2253  | .......... | .......... | ....... |
| GRAC,S  | LLWYS..... | .......... | ....... |
| FISH,S  | .......... | .......... | ....... |
| MN1HAM  | LLWYSRRIVI | .......... | ....... |
| MN2     | .......... | .......... | ....... |
| MN1PAT  | LLWYS..... | .......... | ....... |
| Bmni-6  | LLWYSRRIVI | FNEIYLSHIY | EHSVMIL |
| MN3     | LLWYSR.... | .......... | ....... |
| MR.T    | LLWYSR.... | .......... | ....... |

*Fig. 6B*

… # COMPOUNDS AND METHODS FOR THE DIAGNOSIS AND TREATMENT OF *B. MICROTI* INFECTION

CROSS-REFERENCE TO RELATED APPLICATIONS

This application is a continuation-in-part of U.S. application Ser. No. 09/286,488, filed Apr. 5, 1999, which is a continuation-in-part of U.S. application Ser. No. 08/990, 571, U.S. Pat. No. 6,214,971, filed Dec. 11, 1997 which is a continuation-in-part of U.S. application Ser. No. 08/845, 258, U.S. Pat. No. 6,183,976, filed Apr. 24, 1997, which is a continuation-in-part of U.S. application Ser. No. 08/723, 142 U.S. Pat. No. 6,306,396, filed Oct. 1, 1996.

TECHNICAL FIELD

The present invention relates generally to the detection of *Babesia microti* infection. In particular, the invention is related to polypeptides comprising a *B. microti* antigen, to antigenic epitopes of such an antigen and the use of such polypeptides and antigenic epitopes for the serodiagnosis and treatment of *B. microti* infection.

BACKGROUND OF THE INVENTION

Babesiosis is a malaria-like illness caused by the rodent parasite *Babesia microti* (*B. microti*) which is generally transmitted to humans by the same tick that is responsible for the transmission of Lyme disease and ehrlichiosis, thereby leading to the possibility of co-infection with babesiosis, Lyme disease and ehrlichiosis from a single tick bite. While the number of reported cases of *B. microti* infection in the United States is increasing rapidly, infection with *B. microti*, including co-infection with Lyme disease, often remains undetected for extended periods of time. Babesiosis is potentially fatal, particularly in the elderly and in patients with suppressed immune systems. Patients infected with both Lyme disease and babesiosis have more severe symptoms and prolonged illness compared to those with either infection alone.

The preferred treatments for Lyme disease, ehrlichiosis and babesiosis are different, with penicillins, such as doxycycline and amoxicillin, being most effective in treating Lyme disease, tetracycline being preferred for the treatment of ehrlichiosis, and anti-malarial drugs, such as quinine and clindamycin, being most effective in the treatment of babesiosis. Accurate and early diagnosis of *B. microti* infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. Indirect fluorescent antibody staining methods for total immunoglobulins to *B. microti* may be used to diagnose babesiosis infection, but such methods are time-consuming and expensive. There thus remains a need in the art for improved methods for the detection of *B. microti* infection.

SUMMARY OF THE INVENTION

The present invention provides compositions and methods for the diagnosis and treatment of *B. microti* infection. In one aspect, polypeptides are provided comprising an immunogenic portion of a *B. microti* antigen, or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–17, 37, 40, 42, 45, 50 and 51; (b) the complements of said sequences; and (c) sequences that hybridize to a sequence of (a) or (b) under moderately stringent conditions.

In another aspect, the present invention provides an antigenic epitope of a *B. microti* antigen comprising the amino acid sequence -$X_1$-$X_2$-$X_3$-$X_4$-$X_5$-Ser- (SEQ ID NO: 35), wherein $X_1$ is Glu or Gly, $X_2$ is Ala or Thr, $X_3$ is Gly or Val, $X_4$ is Trp or Gly and $X_5$ is Pro or Ser. In one embodiment of this aspect, $X_1$ is Glu, $X_2$ is Ala and $X_3$ is Gly. In a second embodiment $X_1$ is Gly, $X_2$ is Thr and $X_5$ is Pro. The present invention further provides polypeptides comprising at least two of the above antigenic epitopes, the epitopes being contiguous.

In yet another aspect, the present invention provides an antigenic epitope of a *B. microti* antigen comprising an amino acid sequence selected from the group consisting of SEQ ID NO: 36 and 39, together with polypeptides comprising at least two such antigenic epitopes, the epitopes being contiguous.

In a related aspect, polynucleotides encoding the above polypeptides, recombinant expression vectors comprising these polynucleotides and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope. In specific embodiments, fusion proteins comprising an amino acid sequence of SEQ ID NO: 85 or 87 are provided.

In further aspects of the subject invention, methods and diagnostic kits are provided for detecting *B. microti* infection in a patient. In one embodiment, the method comprises: (a) contacting a biological sample with at least one polypeptide comprising an immunogenic portion of a *B. microti* antigen; and (b) detecting in the sample the presence of antibodies that bind to the polypeptide, thereby detecting *B. microti* infection in the biological sample. In other embodiments, the methods comprise: (a) contacting a biological sample with at least one of the above polypeptides or antigenic epitopes; and (b) detecting in the sample the presence of antibodies that bind to the polypeptide or antigenic epitope. Suitable biological samples include whole blood, sputum, serum, plasma, saliva, cerebrospinal fluid and urine. The diagnostic kits comprise one or more of the above polypeptides or antigenic epitopes in combination with a detection reagent.

The present invention also provides methods for detecting *B. microti* infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of a DNA sequence encoding the above polypeptides.

In a further aspect, the present invention provides a method for detecting *B. microti* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment of this aspect, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of *B. microti* infection.

Within other aspects, the present invention provides pharmaceutical compositions that comprise one or more of the above polypeptides or antigenic epitopes, or a polynucleotide encoding such polypeptides, and a physiologically acceptable carrier. The invention also provides vaccines comprising one or more of the inventive polypeptides or antigenic epitopes and a non-specific immune response enhancer, together with vaccines comprising one or more polynucleotides encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A and 1B show the genomic sequence of the *B. microti* antigen BMNI-3 (SEQ ID NO: 3) including a translation of the putative open reading frame (SEQ ID NO: 49). An internal six amino acid repeat sequence (SEQ ID NO: 35) is indicated by vertical lines within the open reading frame.

FIGS. 6A and 6B show an alignment of the repeat region of different homologues of the *B. microti* antigen BMNI-6, illustrating the geographic variation in the number and location of the repeats.

DETAILED DESCRIPTION OF THE INVENTION

Figure 2A:
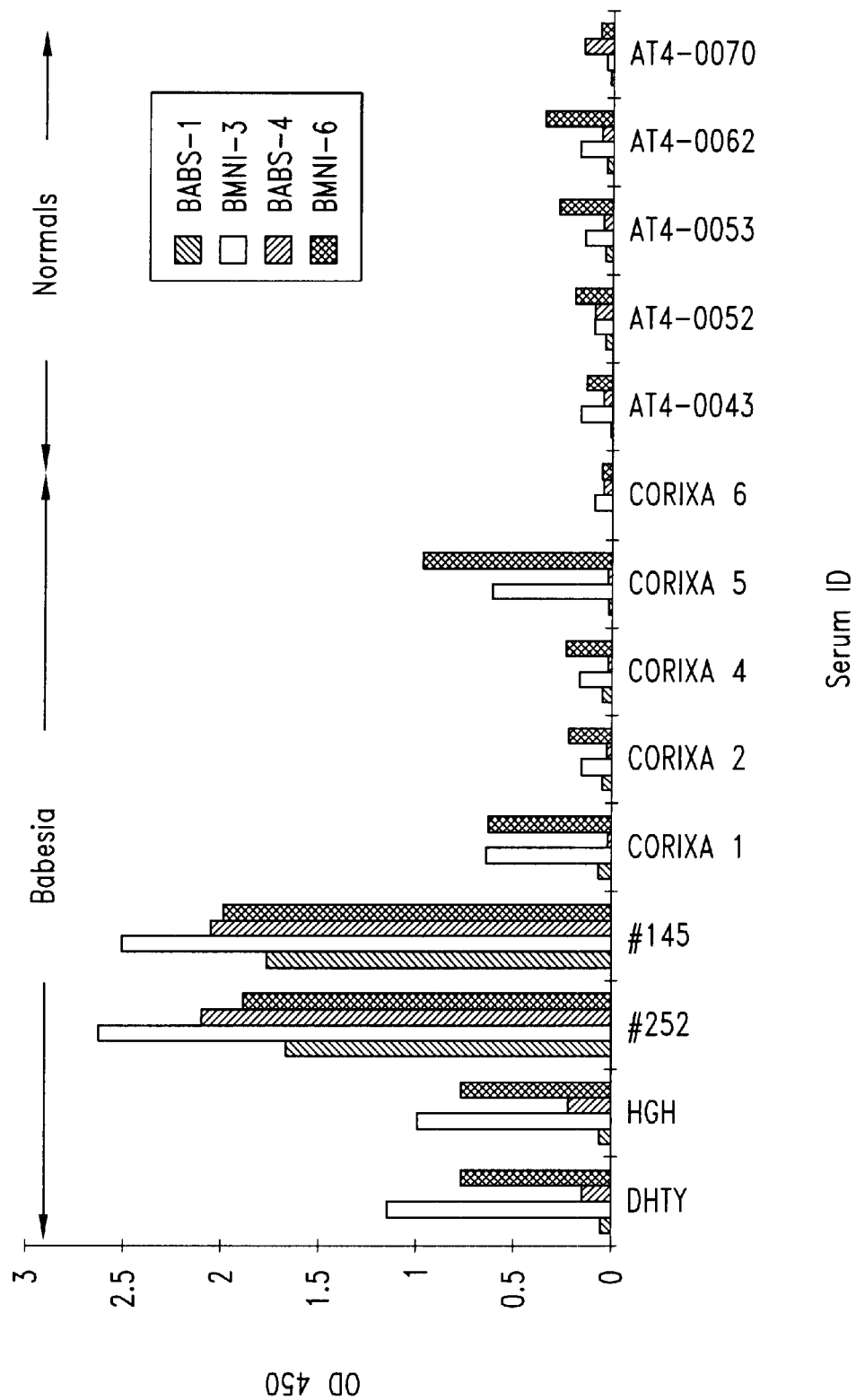
FIG. 2a shows the reactivity of the *B. microti* antigens BMNI-3 and BMNI-6, and the peptides BABS-1 and BABS-4 with sera from *B. microti*-infected individuals and from normal donors as determined by ELISA.
Figure 2B:
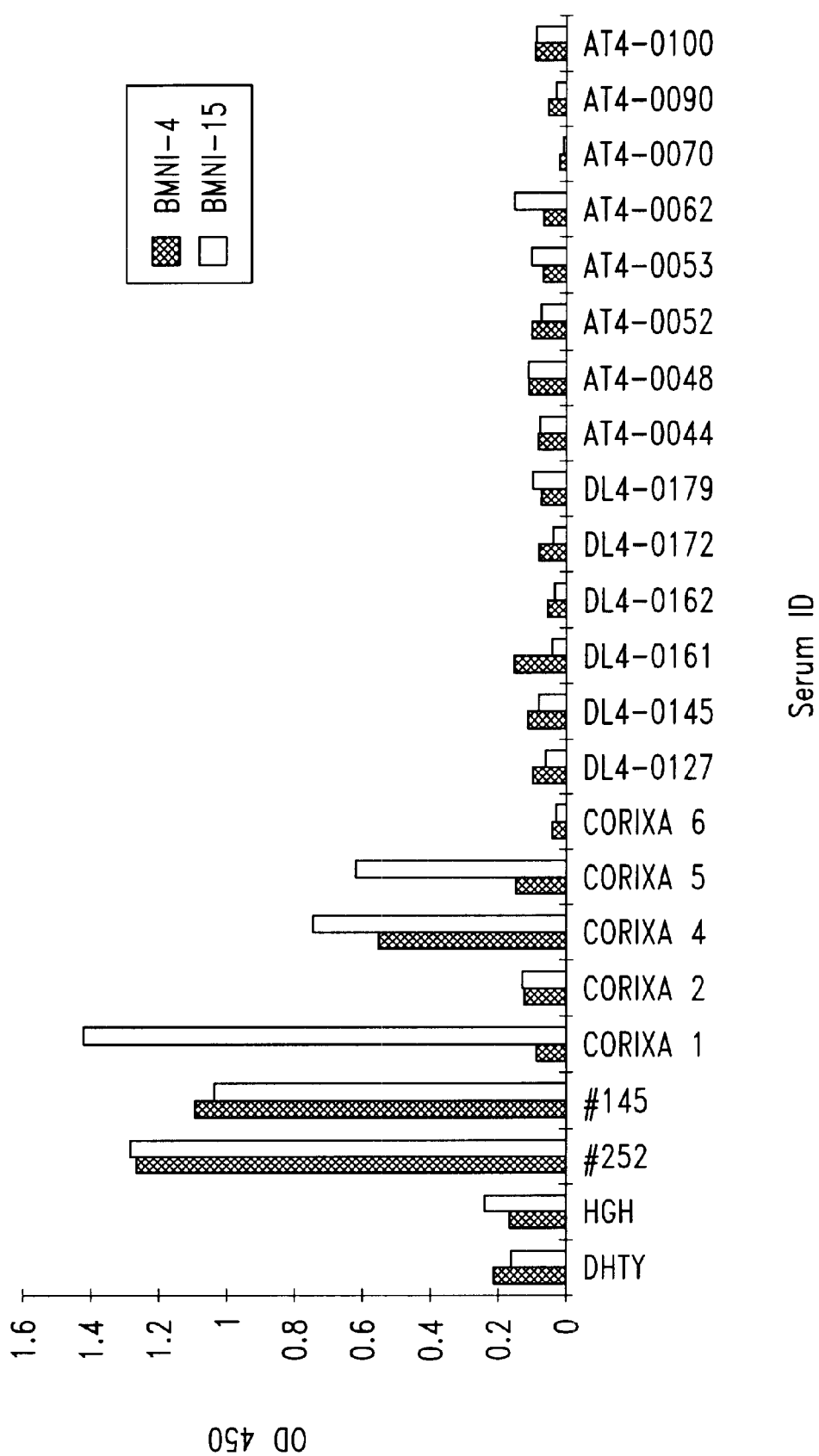
FIG. 2b shows the reactivity of the *B. microti* antigens BMNI-4 and BMNI-15 with sera from *B. microti*-infected individuals and from normal donors as determined by ELISA.
Figure 3:
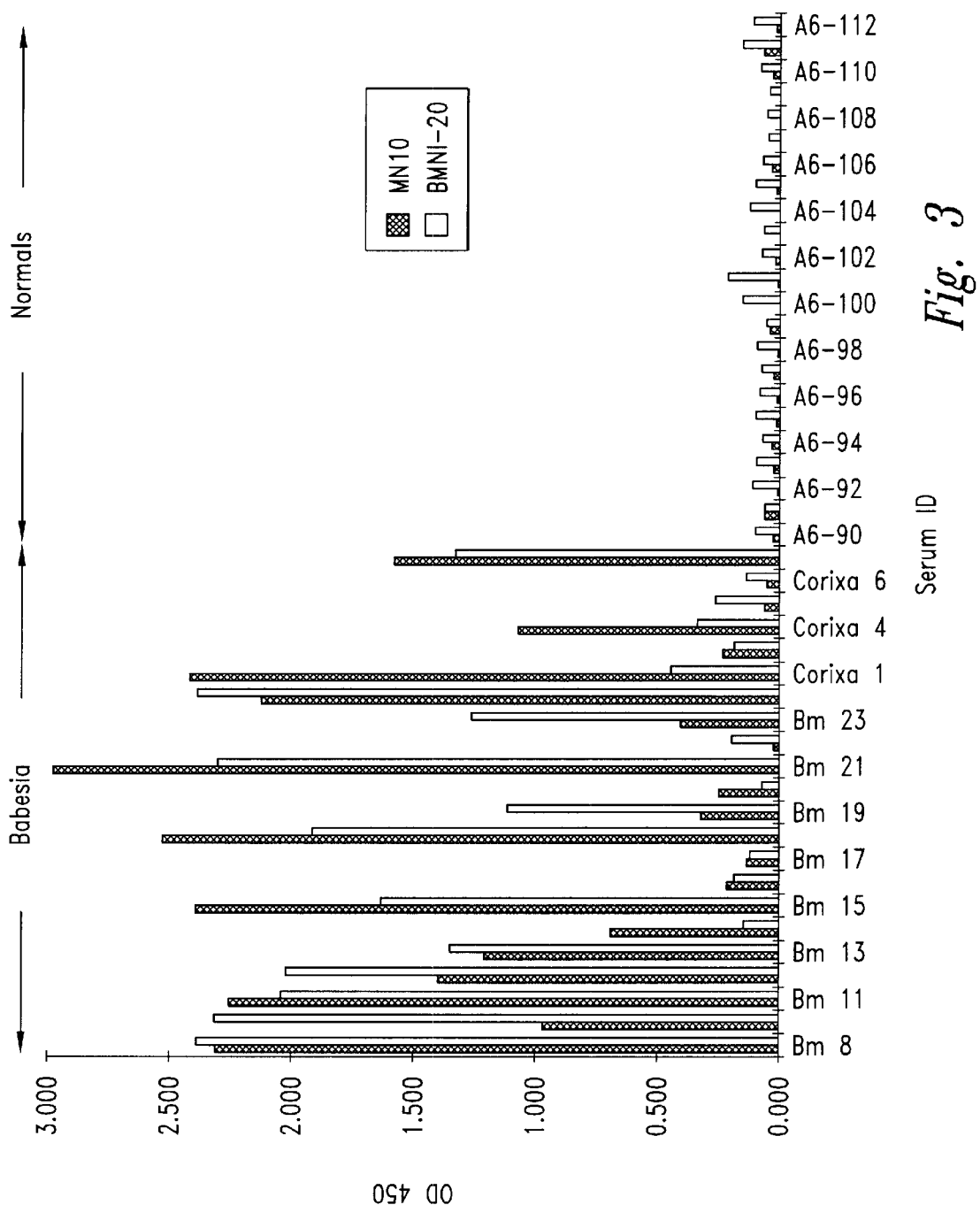
FIG. 3 shows the reactivity of the *B. microti* antigens MN-10 and BMNI-20 with sera from *B. microti*-infected patients and from normal donors as determined by ELISA.

As noted above, the present invention is generally directed to compositions and methods for the diagnosis and treatment of *B. microti* infection. In one aspect, the compositions of the subject invention include polypeptides that comprise at least one immunogenic portion of a *B. microti* antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *B. microti* antigen or may be heterologous, and such sequences may (but need not) be immunogenic.

An "immunogenic portion" of an antigen is a portion that is capable of reacting with sera obtained from a *B. microti*-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more *B. microti* antigens as described herein may generally be used, alone or in combination, to detect *B. microti* in a patient. Polynucleotides encoding the inventive polypeptides are also provided. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

The compositions and methods of the present invention also encompass variants of the above polypeptides and polynucleotides. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A polynucleotide "variant" is a sequence that differs from the recited polynucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Polynucleotide variants may be naturally occurring allelic variants, or non-naturally occurring variants. Variant polynucleotide sequences preferably exhibit at least about 70%, more preferably at least about 80% and most preferably at least about 90% identity (determined as described below) to the recited sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

In specific embodiments, the subject invention discloses polypeptides comprising at least an immunogenic portion of a *B. microti* antigen (or a variant of such an antigen), that comprises one or more of the amino acid sequences encoded by (a) a DNA sequence selected from the group consisting of SEQ ID NO: 1–17, 37, 40, 42, 45 50, 51 and 56–67, (b) the complements of such DNA sequences or (c) DNA sequences substantially homologous to a sequence of (a) or (b).

The *B. microti* antigens provided by the present invention include variants that are encoded by polynucleotides which are substantially homologous to one or more of the polynucleotides specifically recited herein. "Substantial homology," as used herein, refers to polynucleotides that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotides are also within the scope of this invention, as are polynucleotide sequences that, due to code degeneracy, encode an immunogenic polypeptide that is encoded by a hybridizing polynucleotide.

In general, *B. microti* antigens, and polynucleotides encoding such antigens, may be prepared using any of a variety of procedures. For example, polynucleotides encoding *B. microti* antigens may be isolated from a *B. microti* genomic or cDNA expression library by screening with sera from *B. microti*-infected individuals as described below in Example 1, and sequenced using techniques well known to those of skill in the art. Polynucleotides encoding *B. microti* antigens may also be isolated by screening an appropriate *B. microti* expression library with anti-sera (e.g., rabbit) raised specifically against *B. microti* antigens.

Antigens may be induced from such clones and evaluated for a desired property, such as the ability to react with sera obtained from a *B. microti*-infected individual as described herein. Alternatively, antigens may be produced recombinantly, as described below, by inserting a polynucleotide that encodes the antigen into an expression vector and expressing the antigen in an appropriate host. Antigens may be partially sequenced using, for example, traditional Edman chemistry. See Edman and Berg, *Eur. J. Biochem.* 80:116–132, 1967.

Polynucleotides encoding antigens may also be obtained by screening an appropriate *B. microti* cDNA or genomic DNA library for polynucleotides that hybridize to degenerate oligonucleotides derived from partial amino acid sequences of isolated antigens. Degenerate oligonucleotides for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of *B. microti* antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a *B. microti* antigen generates at least about 20%, and preferably about 100%, of the signal induced by the full length antigen in a model ELISA as described herein.

Portions and other variants of *B. microti* antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a polynucleotide encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line, such as COS or CHO. The polynucleotides expressed in this manner may encode naturally occurring antigens, portions of naturally occurring antigens, or other variants thereof.

In another aspect, the present invention provides epitope repeat sequences, or antigenic epitopes, of a *B. microti* antigen, together with polypeptides comprising at least two such contiguous antigenic epitopes. As used herein an "epitope" is a portion of an antigen that reacts with sera from *B. microti*-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise the amino acid sequence -$X_1$-$X_2$-$X_3$-$X_4$-$X_5$-Ser- (SEQ ID NO: 35), wherein $X_1$ is Glu or Gly, $X_2$ is Ala or Thr, $X_3$ is Gly or Val, $X_4$ is Trp or Gly, and $X_5$ is Pro or Ser. In another embodiment, the antigenic epitopes of the present invention comprise an amino acid sequence selected from the group consisting of SEQ ID NO: 36 and 39. As discussed in more detail below, antigenic epitopes provided herein may be employed in the diagnosis and treatment of *B. microti* infection, either alone or in combination with other *B. microti* antigens or antigenic epitopes. Antigenic epitopes and polypeptides comprising such epitopes may be prepared by synthetic means, as described generally above and in detail in Example 2.

In general, regardless of the method of preparation, the polypeptides, polynucleotides and antigenic epitopes disclosed herein are prepared in an isolated, substantially pure, form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope or an inventive polypeptide and an antigenic epitope of the present invention, together with variants of such fusion proteins. The fusion proteins of the present invention may also include a linker peptide between the polypeptides or antigenic epitopes.

A polynucleotide encoding a fusion protein of the present invention is constructed using known recombinant DNA techniques to assemble separate polynucleotides encoding, for example, the first and second polypeptides into an appropriate expression vector. The 3' end of a polynucleotide encoding the first polypeptide is ligated, with or without a peptide linker, to the 5' end of a polynucleotide encoding the second polypeptide so that the reading frames of the sequences are in phase to permit mRNA translation of the two polynucleotides into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. Nos. 4,935,233 and 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using polypeptides comprising an immunogenic portion of a *B. microti* antigen and/or the antigenic epitopes described above to diagnose babesiosis. In this aspect, methods are provided for detecting *B. microti* infection in a biological sample, using one or more of the above polypeptides and antigenic epitopes, alone or in combination. For clarity, the term "polypeptide" will be used when describing specific embodiments of the inventive diagnostic methods. However, it will be clear to one of skill in the art that the antigenic epitopes of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *B. microti* antigens which may be indicative of babesiosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *B. microti*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *B. microti*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*B. microti* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for babesiosis. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for babesiosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*B. microti* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies: A Laboratory Manual,* Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide or antigenic epitope coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of *B. microti* antigens using assays similar to those detailed above and other techniques well known to those of skill in the art, thereby providing a method for detecting *B. microti* infection in a patient.

Diagnostic reagents of the present invention may also comprise oligonucleotides encoding one or more of the above polypeptides, or one or more portions thereof. For example, at least two oligonucleotide primers may be employed in a polymerase chain reaction (PCR) based assay to amplify *B. microti*-specific cDNA derived from a biological sample, wherein at least one of the oligonucleotide primers is specific for (i.e. hybridizes to) a polynucleotide encoding a polypeptide of the present invention. The presence of the amplified cDNA is then detected using techniques well known in the art, such as gel electrophoresis. Similarly, oligonucleotide probes that specifically hybridize to a polynucleotide encoding a polypeptide of the present invention may be used in a hybridization assay to detect the presence of an inventive polypeptide in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an inventive polypeptide that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a polynucleotide of the present invention. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an uninfected individual. The amplification reaction may be performed on several dilutions of cDNA spanning two orders of magnitude. A two-fold or greater increase in expression in several dilutions of the test patient sample as compared to the same dilutions of the non-infected sample is typically considered positive.

Primers or probes may thus be used to detect *B. microti*-specific sequences in biological samples, preferably sputum, blood, serum, saliva, cerebrospinal fluid or urine. Oligonucleotide primers and probes may be used alone or in combination with each other.

In another aspect, the present invention provides methods for using one or more of the above polypeptides, antigenic epitopes or fusion proteins (or polynucleotides encoding such polypeptides) to induce protective immunity against *B. microti* infection in a patient. As used herein, a "patient" refers to any warm-blooded animal, preferably a human. A patient may be afflicted with a disease, or may be free of detectable disease and/or infection. In other words, protective immunity may be induced to prevent or treat babesiosis.

In this aspect, the polypeptide, antigenic epitope, fusion protein or polynucleotide is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *B. microti* antigens, either incorporated into a combination polypeptide or present within a separate polypeptide.

Alternatively, a vaccine may contain a polynucleotide encoding one or more polypeptides, antigenic epitopes or fusion proteins as described above, such that the polypeptide is generated in situ. In such vaccines, the polynucleotide may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotide may be introduced using a viral expression system (e.g., vaccinia or other pox virus, retrovirus, or adenovirus), which may involve the use of a non-pathogenic (defective), replication competent virus. Techniques for incorporating polynucleotides into such expression systems are well known to those of ordinary skill in the art. The polynucleotide may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *B. microti* antigen. For example, administration of a polynucleotide encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or polynucleotide that, when administered as described above, is capable of raising an immune response in an immunized patient sufficient to protect the patient from B. microti infection for at least 1–2 years. In general, the amount of polypeptide present in a dose (or produced in situ by the polynucleotide in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or Mycobacterium tuberculosis. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

The following Examples are offered by way of illustration and not by way of limitation.

EXAMPLE 1

Isolation of DNA Sequences Encoding B. Microti Antigens

This example illustrates the preparation of DNA sequences encoding B. microti antigens by screening a B. microti expression library with sera obtained from patients infected with B. microti.

B. microti genomic DNA was isolated from infected hamsters and sheared by sonication. The resulting randomly sheared DNA was used to construct a B. microti genomic expression library (approximately 0.5–4.0 kbp inserts) with EcoRI adaptors and a Lambda ZAP II/EcoRI/CIAP vector (Stratagene, La Jolla, Calif.). The unamplified library (1.2× $10^6$/ml) was screened with an E. coli lysate-absorbed B. microti patient serum pool, as described in Sambrook et al., *Molecular Cloning: A Laboratory Manual,* Cold Spring Harbor Laboratories, Cold Spring Harbor, N.Y., 1989. Positive plaques were visualized and purified with goat-antihuman alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Seventeen antigens (hereinafter referred to as BMNI-1–BMNI-17) were purified and three were possibly redundant. The determined DNA sequences for BMNI-1–BMNI-17 are shown in SEQ ID NO: 1–17, respectively. The deduced amino acid sequences for BMNI-1–BMNI-6, BMNI-8 and BMNI-10–BMNI-17 are shown in SEQ ID NO: 18–32, respectively, with the predicted 5' and 3' protein sequences for BMNI-9 being shown in SEQ ID NO: 33 and 34, respectively.

The isolated DNA sequences were compared to known sequences in the gene bank using the DNA STAR system. Nine of the seventeen antigens (BMNI-1, BMNI-2, BMNI-3, BMNI-5, BMNI-6, BMNI-7, BMNI-12, BMNI-13 and BMNI-16) share some homology, with BMNI-1 and BMNI-16 being partial clones of BMNI-3. All of these nine antigens contain a degenerate repeat of six amino acids (SEQ ID NO: 35), with between nine to twenty-two repeats occurring in each antigen. The repeat portion of the sequences was found to bear some similarity to a *Plasmodium falciparum* merozoite surface antigen (MSA-2 gene). FIG. 1 shows the genomic sequence of BMNI-3 including a translation of the putative open reading frame, with the internal six amino acid repeat sequence being indicated by vertical lines within the open reading frame.

A second group of five antigens bear some homology to each other but do not show homology to any previously identified sequences (BMNI-4, BMNI-8, BMNI-9, BMNI-10 and BMNI-11). These antigens may belong to a family of genes or may represent parts of a repetitive sequence. BMNI-17 contains a novel degenerate repeat of 32 amino acids (SEQ ID NO: 36). Similarly, the reverse complement of BMNI-17 (SEQ ID NO: 37) contains an open reading frame that encodes an amino acid sequence (SEQ ID NO: 38) having a degenerate 32 amino acid repeat (SEQ ID NO: 39).

The reverse complement of BMNI-3 (SEQ ID NO: 40) has an open reading frame which shows homology with the BMNI-4-like genes. The predicted amino acid sequence encoded by this open reading frame is shown in SEQ ID NO: 41. The reverse complement of BMNI-5 (SEQ ID NO: 42) contains a partial copy of a BMNI-3-like sequence and also an open reading frame with some homology to two yeast genes (*S. cerevisiae* G9365 ORF gene, and *S. cerevisiae* accession no. U18922). The predicted 5' and 3' amino acid sequences encoded by this open reading frame are shown in SEQ ID NO: 43 and 44, respectively. The reverse complement of BMNI-7 (SEQ ID NO: 45) contains an open reading frame encoding the amino acid sequence shown in SEQ ID NO: 46.

A telomeric repeat sequence, which is conserved over a wide range of organisms, was found in five antigens (BMNI-2, BMNI-5, BMNI-6, BMNI-7 and BMNI-16), indicating that many of the isolated genes may have a telomere-proximal location in the genome. BMNI-10 appears to include a double insert, the 3'-most segment having some homology to *E. coli* aminopeptidase N. In addition, BMNI-7 contains apparently random insertions of hamster DNA. One such insertion has characteristics of a transposible element (i.e. poly A tail and flanked by a direct repeat).

In subsequent studies, two additional *B. microti* antigens were isolated by screening the *B. microti* genomic DNA expression library described above with a serum pool from *B. microti* infected patients that showed low reactivity with recombinant proteins generated from clones BMNI-2–BMNI-17. The determined DNA sequences for these two clones, hereinafter referred to as MN-10 and BMNI-20, are provided in SEQ ID NO: 50 and 51, respectively, with the corresponding predicted amino acid sequences being provided in SEQ ID NO: 52 and 53. MN-10 was found to extend the sequence of BMNI-4 in the 3' direction and BMNI-20 was found to extend the sequence of BMNI-17 in the 5' direction.

EXAMPLE 2

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize two peptides (hereinafter referred to as BABS-1 and BABS-4) made to the repeat region of the isolated *B. microti* antigen BMNI-3. The sequences of BABS-1 and BABS-4 are shown in SEQ ID NO: 47 and 48, respectively.

EXAMPLE 3

Use of Representative Antigens and Peptides for Serodiagnosis of *B. Microti* Infection A. Diagnostic Properties of Representative Antigens and Peptides as Determined by ELISA The diagnostic properties of recombinant BMNI-3, BMNI-4, BMNI-6, BMNI-15, MN-10 and BMNI-20, and the BABS-1 and BABS-4 peptides were determined as follows.

Assays were performed in 96 well plates coated overnight at 4° C. with 200 ng antigen/well added in 50 μl of carbonate coating buffer. The plate contents were then removed and the wells were blocked for 2 hours with 200 μl of PBS/1% BSA. After the blocking step, the wells were washed six times with PBS/0.1% Tween 20™. Fifty microliters of sera, diluted 1:100 in PBS/0.1% Tween 20™/0.1% BSA, was then added to each well and incubated for 30 minutes at room temperature. The plates were then washed six times with PBS/0.1% Tween 20™.

The enzyme conjugate (horseradish peroxidase-Protein A, Zymed, San Francisco, Calif.) was then diluted 1:20,000 in PBS/0.1% Tween 20™/0.1% BSA, and 50 μl of the diluted conjugate was added to each well and incubated for 30 minutes at room temperature. Following incubation, the wells were washed six times with PBS/0.1% Tween 20™, 100 μl of tetramethylbenzidine peroxidase substrate (Kirkegaard and Perry Laboratories, Gaithersburg, Md.) was added, undiluted, and incubated for 15 minutes. The reaction was stopped by the addition of 100 μl of 1N $H_2SO_4$ to each well and the plates were read at 450 nm.

FIG. 2*a* shows the reactivity of the recombinant BMNI-3 and BMNI-6 antigens and the two peptides BABS-1 and BABS-4 in the ELISA assay. The recombinant antigens and the two peptides were negative in ELISA with all seven samples from normal (*B. microti* negative) individuals. In contrast, both BMNI-3 and BMNI-6 detected six of the nine *B. microti*-infected samples, as compared to two out of the nine for the BABS-1 and BABS-4 peptides. This would suggest that BMNI-3 and BMNI-6 may contain other antigenic epitopes in addition to those present in the repeat epitopes in BABS-1 and BABS-4, or that an insufficient number of repeats are available in the peptides to fully express the antigenic epitopes present in the recombinant antigens BMNI-3 and BMNI-6.

FIG. 2*b* shows the ELISA reactivity of the recombinant antigens BMNI-4 and BMNI-15. Both recombinants were negative with all fifteen samples from normal individuals. BMNI-4 detected four out of nine *B. microti*-infected samples and BMNI-15 detected six out of nine *B. microti*-infected samples. Both BMNI-4 and BMNI-15 detected a *B. microti*-infected sample which was not detected by BMNI-3 or BMNI-6, suggesting that BMNI-4 and BMNI-15 might be complementary to BMNI-3 and BMNI-6 in the ELISA test described herein.

The ELISA reactivity of recombinant MN-10 and BMNI-20 with sera from *B. microti*-infected patients and from normal donors is shown in FIG. 3. MN-10 and BMNI-20 were found to be reactive with *B. microti*-infected sera that were not reactive with recombinant BMNI-2 through BMNI-17. Therefore, MN-10 and BMNI-20 may be usefully employed in combination with other *B. microti* antigens of the present invention for the detection of *B. microti* infection.

Table 1 shows the reactivity of the recombinant *B. microti* antigens BMNI-2, BMNI-17, MN-10 and a combination of BMNI-17 and MN-10, as determined by ELISA, with Babesia-positive sera, sera positive for both Babesia and Ehrlichia, sera positive only for Ehrlichia, Lyme disease sera and sera from normal donors. The data indicate a sensitivity of approximately 93% and a specificity in normal donors in excess of 98%. These results indicate that a combination of BMNI-17 and MN-10 is particularly effective in the diagnosis of *B. microti* infection.

TABLE 1

| Antigen | Babesia | Babesia/Ehrlichia | Ehrlichia | Lyme | Normal donors |
|---|---|---|---|---|---|
| BMNI-2 | 27/50 | 2/3 | 1/4 | 0/10 | 1/73 |
| BMNI-17 | 35/50 | 3/3 | 0/4 | 0/10 | 0/86 |
| MN-10 | 37/49 | 3/3 | 0/4 | 1/10 | 1/98 |
| BMNI-17/ MN-10 | 46/50 | 3/3 | 0/4 | 1/10 | 1/98 |

B. Diagnostic Properties of Representative Antigens and Peptides as Determined by Western Analysis Western blot analyses were performed on representative *B. microti* antigens as follows.

Antigens were induced as pBluescript SK− constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 0.1% Tween 20™/PBS. Blots were then washed 3 times in 0.1% Tween 20™/PBS and incubated with a *B. microti* patient serum pool (1:200) for a period of 2 hours. After washing blots in 0.1% Tween 20™/PBS 3 times, immunocomplexes were detected by the addition of Protein A conjugated to $^{125}$I (1/25000; NEN-Dupont, Billerica, Mass.) followed by exposure to X-ray film (Kodak XAR 5; Eastman Kodak Co., Rochester, N.Y.) at −70° C. for 1 day.

Figure 4:
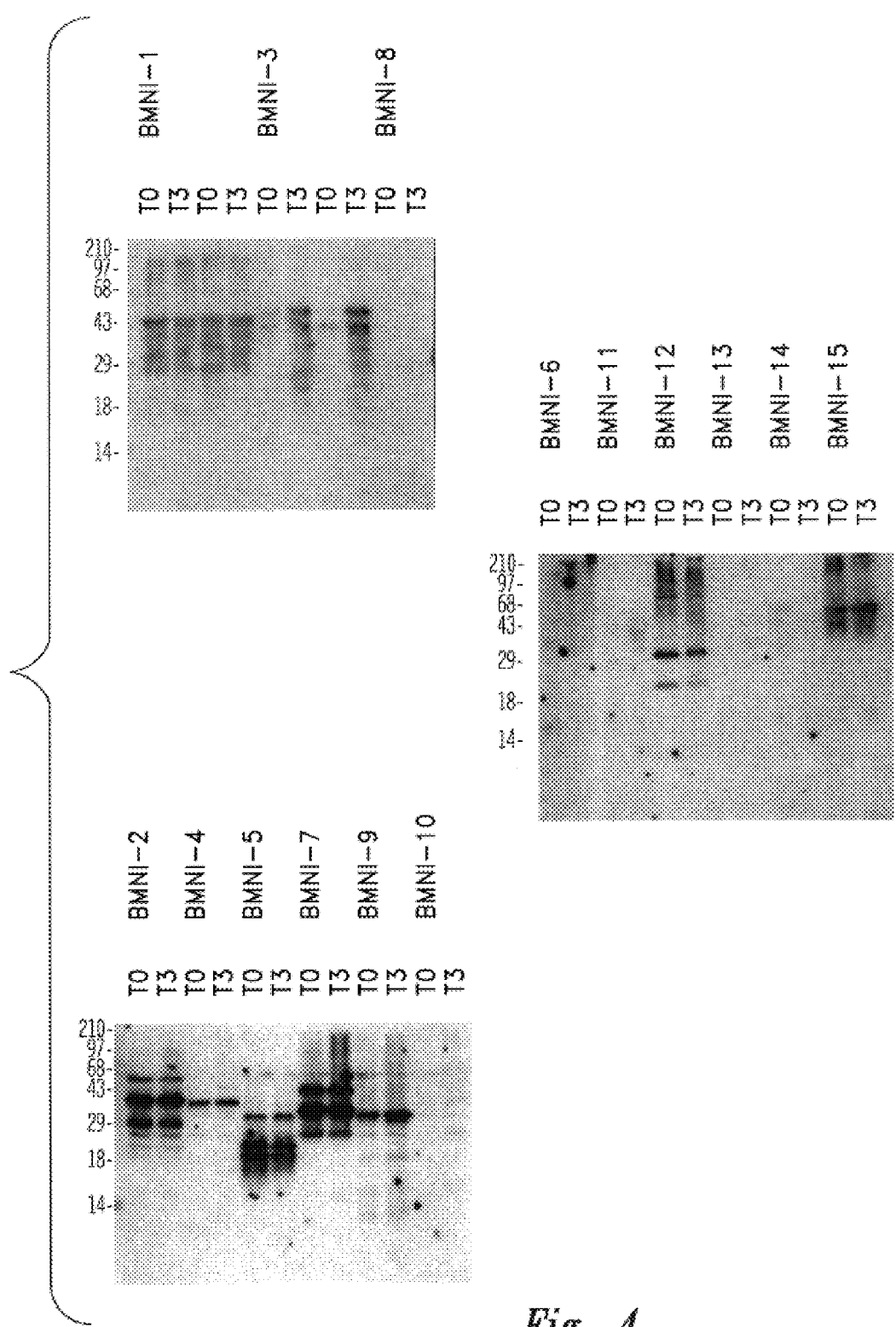
FIG. 4 shows the results of Western blot analysis of representative *B. microti* antigens of the present invention.

As shown in FIG. 4, resulting bands of reactivity with serum antibody were seen at 43 kDa for BMNI-1, 38 kDa for BMNI-2, 45 kDa for BMNI-3, 37 kDa for BMNI-4, 18 and 20 kDa for BMNI-5, 35 and 43 kDa for BMNI-7, 32 kDa for BMNI-9, 38 kDa for BMNI-11, 30 kDa for BMNI-12, 45 kDa for BMNI-15, and 43 kDa for BMNI-17 (not shown). Antigen BMNI-6, after reengineering as a pET 17b construct (Novagen, Madison, Wis.) showed a band of reactivity at 33 kDa (data not shown). Protein size standards, in kDa (Gibco BRL, Gaithersburg, MB), are shown to the left of the blots.

Western blots were performed on purified BMNI-3, BMNI-2, BMNI-15, BMNI-17 and MN-10 recombinant antigen with a series of patient sera from *B. microti* patients and from patients with either Lyme disease or ehrlichiosis. Specifically, purified recombinant antigen (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 5:
FIG. 5 shows the reactivity of purified recombinant *B. microti* antigen BMNI-3 with sera from *B. microti*-infected patients, Lyme disease-infected patients, ehrlichiosis-infected patients and normal donors as determined by Western blot analysis.

Lanes 1–9 of FIG. 5 show the reactivity of purified recombinant BMNI-3 with sera from nine *B. microti*-infected patients, of which five were clearly positive and a further two were low positives detectable at higher exposure to the hyperfilm ECL. This correlates with the reactivity as determined by ELISA. In contrast, no immunoreactivity was seen with sera from patients with either ehrlichiosis (lanes 10 and 11) or Lyme disease (lanes 12–14), or with sera from normal individuals (lanes 15–20). A major reactive band appeared at 45 kDa and a small break down band was seen at approximately 25 kDa.

Table 2, below, summarizes the reactivity of the recombinant antigens BMNI-2, BMNI-15, BMNI-17 and MN-10 with *B. microti* positive sera. No reactivity was seen with Lyme or Ehrlichia-infected sera, with little or no reactivity being seen with normal sera.

TABLE 2

| Sample ID | BMNI-2 | BMNI-15 | BMNI-17 | MN-10 |
|---|---|---|---|---|
| BM8 | ++ | ++ | +++++ | — |
| BM21 | ++ | — | ++++ | ++++ |
| COR4 | ± | ++++ | ++++ | + |
| COR5 | ± | +++ | + | — |
| 252 | ++++ | ++++ | ++++++ | +++ |

— indicates no reactivity

EXAMPLE 4

Analysis of Georgraphic Variation within Antigens

The reactivity of the inventive antigens with sera from *B. microti* patients, as determined by Western blot, was found to vary with the U.S. location of the patients. Accordingly, geographic variation within the gene encoding the exemplary antigen BMNI-6 was examined as follows.

Two PCR primers, referred to as BMNI-6/5' and BMNI-6/3' (SEQ ID NOS: 54 and 55, respectively) were designed based on the region flanking the six amino acid degenerate repeat region of BMNI-6 (SEQ ID NO: 6). These primers were employed to amplify genomic DNA from whole blood obtained from twelve *B. microti*-infected patients and genomic DNA from whole blood from *P. leucopus* and hamsters in a Perkin Elmer 480 thermal cycler using the manufacturer's protocol. PCR products were evaluated for size on 2% agarose gels and then Southern blotted and probed with a DIG-labeled oligonucleotide. Positive clones were sequenced using an Applied Biosystems Model 373A or 377 sequencer. RT-PCR was performed on Trizol LS extracted *B. microti*-infected hamster whole blood RNA using the primers described above, and the resulting clones were sequenced as described above.

These studies resulted in the isolation of twelve BMNI-6 homologues, referred to hereinafter as BI254, BI1053, BI2227, BI2259, BI2253, BI2018, RIFS, MN1HAM, MN2, MN1PAT, MN3 and MRT with MN1HAM being obtained from hamster and the other eleven from patients. The determined DNA sequences of these clones are provided in SEQ ID NO: 56–67, respectively, with the corresponding predicted amino acid sequences being provided in SEQ ID NO: 68–79, respectively. Isolates from hamsters had the same sequences as found in the corresponding human blood, suggesting that genetic variation of BMNI-6 does not occur during passage. However, clones from different patients often showed variation in the number and location of the degenerate repeat found within BMNI-6. An alignment of the repeat regions from each of the twelve clones is provided in FIG. 6. Furthermore, strains that were closely related geographically were also closely related at the sequence level. For example, three patients from Nantucket Island, Mass., harbored clones (BI2253, BI2259 and BI2227) that were indistinguishable from each other but distinct from those found in other northeastern or upper midwestern strains. These results suggest that considerable antigenic diversity exists among isolates of *B. microti* from the U.S. and that geographic clustering of subtypes exists.

EXAMPLE 5

Preparation and Characterization of B. Microti Fusion Proteins

A. Preparation of a Fusion Protein Containing MN-10 and BMNI-17

A fusion protein containing the B. microti antigens MN-10 and BMNI-17, referred to as BaF-3, was prepared as follows.

MN-10 and BMNI-17 DNA was used to perform PCR using the primers PDM-285 and PDM-286 (SEQ ID NO: 80 and 81); and PDM-283 and PDM-284 (SEQ ID NO: 82 and 83), respectively. In both cases, the DNA amplification was performed using 10 µl of 10× Pfu buffer (Stratagene), 1 µl of 10 mM dNTPs, 2 µl each of the PCR primers at 10 µM concentration, 83 µl water, 1.5 µl Pfu DNA polymerase (Stratagene, La Jolla, Calif.) and 1 µl DNA at 50 ng/µl. Denaturation at 96° C. was performed for 2 min, followed by 40 cycles of 96° C. for 20 sec, 59° C. for 15 sec and 72° C. for 3 min, an by 72° C. for 4 min. The MN-10 and BMNI-17 PCR products were digested with SspI and then ligated using a ligation kit from Panvera (Madison, Wis.). The resulting BaF-3 fusion was PCR amplified using primers PDM 285 and PDM-284 and the same conditions as listed above. This PCR product was then digested with ScaI and EcoRI, and cloned into a modified pET28 vector. The fusion construct was confirmed by sequencing. The expression construct was transformed into BL21 (DE3) CodonPlus cells (Novagen, Madison, Wis.) for induction and expression. The protein came out in the inclusion body pellet. This pellet was washed three times with a 0.5% CHAPS wash in 20 mM Tris (8.0) and 300 mM NaCl. The pellet was then solubilized in 8 M urea, 20 mM Tris (8.0), 300 mM NaCl and batch bound to Nickel NTA resin (Qiagen). The nickel resin was washed with 100 ml 8 M urea, 20 mM Tris (9.0), 300 mM NaCl, 1% DOC. A second wash was performed as described for the first wash, but with the omission of DOC. The protein was first eluted with 8 M urea, 20 mM Tris (9.0), 100 mM NaCl and 500 mM imidazole. In a second elution, the imidazole was increased to 1 M. The elutions were run on a 4–20 SDS-PAGE gel and the fractions containing the protein of interest were pooled and dialyzed against 1 mM Tris (8.).

The determined cDNA sequence of coding region for the BaF-3 fusion protein is provided in SEQ ID NO: 84, with the corresponding amino acid sequence being provided in SEQ ID NO: 85.

B. Preparation of a Fusion Protein Containing BMNI-15, MN-10 and BMNI-17

A fusion protein containing the B. microti antigens BMNI-15, MN-10 and BMNI-17, referred to as BaF-4, was prepared as follows.

BMNI-15 DNA was used to perform PCR using the primers PDM-349 and PDM-363 (SEQ ID NO: 88 and 89). DNA amplification was performed using 10 µl of 10× Pfu buffer (Stratagene), 1 µl of 10 mM dNTPs, 2 µl each of the PCR primers at 10 µM concentration, 83 µl water, 1.5 µl Pfu DNA polymerase (Stratagene, La Jolla, Calif.) and 1 µl DNA at 50 ng/µl. Denaturation at 96° C. was performed for 2 min, followed by 40 cycles of 96° C. for 20 sec, 61° C. for 15 sec and 72° C. for 3 min, and lastly by of 72° C. for 4 min. The PCR product was digested with PvuII and EcoRI, and cloned into a modified pET28 vector, which had been cut with Eco72I and EcoRI. The construct was confirmed to be correct by sequencing. MN-10/BMNI-17 DNA from BaF-3, described above, was used to perform PCR using the primers PDM-364 and PDM-284 (SEQ ID NO: 90 and 83, respectively). DNA amplification was performed using 10 µl of 10× Pfu buffer (Stratagene), 1 µl of 10 mM dNTPs, 2 µl each of the PCR primers at 10 µM concentration, 83 µl water, 1.5 µl Pfu DNA polymerase (Stratagene, La Jolla, Calif.) and 1 µl DNA at 50 ng/µl. Denaturation at 96° C. was performed for 2 min, followed by 40 cycles of 96° C. for 20 sec, 60° C. for 15 sec and 72° C. for 6 min, and lastly by 72° C. for 4 min. The PCR product was cut with BamHI and EcoRI, and cloned into the pPDM BMNI-15 construct at the BamHI and EcoRI sites. The resulting construct was found by sequence analysis to have a single base pair deletion 419 bp in from the stop codon. This base pair deletion was corrected by digesting the pPDM BaF4B-6 clone with KpnI and SphI, and purifying the 2.6 kb insert plus 5' vector. This band was then cloned into pPDM Trx2H BaF3-10 that was digested with the same enzymes and contained the 3' end of BMNI-17 plus most of the pPDM vector. The correct sequence was confirmed by sequence analysis and then transformed into the BL21 CodonPlus expression host (Novagen).

The determined cDNA sequence of the coding region of the BaF-4 fusion protein is provided in SEQ ID NO: 86, with the corresponding amino acid sequence being provided in SEQ ID NO: 87.

One of skill in the art will appreciate that the order of the individual antigens within the fusion protein may be changed and that comparable or enhanced activity could be expected provided each of the epitopes is still functionally available. In addition, truncated forms of the proteins containing active epitopes may be used in the construction of fusion proteins.

Although the present invention has been described in some detail by way of illustration and example for purposes of clarity of understanding, changes and modifications can be carried out without departing from the scope of the invention which is intended to be limited only by the scope of the appended claims.

---

SEQUENCE LISTING

<160> NUMBER OF SEQ ID NOS: 90

<210> SEQ ID NO 1
<211> LENGTH: 792
<212> TYPE: DNA
<213> ORGANISM: Babesia microti

<400> SEQUENCE: 1
cactcttttt aatgagcggt gctgtctttg caagtgatac cgatcccgaa gctggtgggc    60

-continued

```
ctagtgaagc tggtgggcct agtggaactg ttgggcccag tgaagctggt gggcctagtg      120
aagctggtgg gcctagtgga actggttggc ctagtgaagc tggtgggcct agtgaagctg      180
gtgggcctag tgaagctggt gggcctagtg aagctggtgg gcctagtgga actggttggc      240
ctagtggaac tggttggcct agtgaagctg ttggtctagt gaacgatttt ggatatcagc      300
ttcttccgta ttctagaaga atagttatat ttaatgaagt ttgttatctt tatatataca      360
aacatagtgt tatgatattg aacgagatag ggtgaacga tggtcataaa gactacattg       420
aagaaaaaac caaggagaag aataaattga aaaagaatt ggaaaatgt tttcctgaac         480 aatattccct tatgaagaaa aagaattgg ctagaatatt tgataatgca tccactatct        540
cttcaaaata taagttattg gttgatgaaa tatcaaacaa ggcctatggt acattggaag      600
gtccagctgc tgataatttt gaccatttcc gtaatatatg aagtctatt gtacttaaag       660 atatgtttat atattgtgac ttattattac aacatttaat ctataaattc tattatgaca      720
ataccgttaa tgatatcaag aaaaattttg acgaatccaa atctaaagct ttagttttga      780
gggataagat ca                                                          792
```

<210> SEQ ID NO 2
<211> LENGTH: 2732
<212> TYPE: DNA
<213> ORGANISM: Babesia microti

<400> SEQUENCE: 2

```
aaaccctaaa ccctaaaccc taaccctaa accctaaacc ctaaaccct aaaccctaaa        60 ccctaaaccc taaaccctaa accctaaac ctaaaccct aaaccctaaa ccctaaaccc        120
taaaccctaa accctaaacc ctaaacccta accctaaac cctaaaccct aaaccctaaa       180
ccctaaaccc taaaccctaa accctaaacc ctaaacccct aaaccctaaa ccctaaaccc      240
taaaccctaa accctaaacc ctaaacccta accctaaac cctaaaccct aaaccctaaa       300
ccctaaaccc taaaccctaa accctaaacc ctaaaacccct aaaccctaaa ccctaaaccc      360
taaaccctaa accctaaacc cctaaaccct aaaccctaaa ccctaaaccc taaaccctaa      420
acccctaaac cctaaacccc taaaccctaa accctaaacc ctaaacccta accctaaac      480 cctaaaccct aaaccctaaa ccctaaaccc taaacccct aaccctaaac cctaaaccct      540
aaaccctaaa ccctaaaccc taaaccctaa accctaaccc taacccta ac cctaaccccta    600 acctagcctt cattgacgtc tatccccaat cttagaaaaa tcttcaaatc gattctagaa     660
taactggaaa caattatcag aaattgtata actgcttatt agcttattag cttattagtt     720
aggatgtatg cacattgatg acaactagat gcagcaccac aatcactacc acgtaccaat     780
catataccaa taatgtacta ataatgtacc aataactatg gtttataaag atggtgtcat      840
ttaaatcaat attagttcct tatattcac tctttttaat gagcggtgct gtctttgcaa       900
gtgataccga tcccgaagct ggtgggccta gtgaagctgg tgggcctagt ggaactgttg     960
ggcccagtga agctggtggg cctagtgaag ctggtgggcc tagtgaact gttgggccca      1020 gtgaagctgg tgggcctagt gaagctggtg ggcctagtgg aactggttgg cctagtgaag     1080
ctggtgggcc tagtgaagct ggtgggccta gtgaactgt tgggcccagt gaagctggtg     1140
ggcctagtga agctggtggg cctagtggaa ctggttggcc tagtgaagct ggtgggccta    1200
gtgaagctgg tgggcctagt gaagctggtg ggcctagtga agctggtggg cctagtggaa    1260
ctggttggcc tagtggaact ggttggccta gtgaagctgg ttggtctagt gaacgatttg    1320
gatatcagct tcttccgtat tctagaagaa tagttatatt taatgaagtt tgtttatctt    1380
```

```
atatatacaa acatagtgtt atgatattgg aacgagatag ggtgaacgat ggtcataaag    1440
actacattga agaaaaaacc aaggagaaga ataaattgaa aaaagaattg gaaaaatgtt    1500
ttcctgaaca atattccctt atgaagaaag aagaattggc tagaatattt gataatgcat    1560
ccactatctc ttcaaaatat aagttattgg ttgatgaaat atcaaacaag gcctatggta    1620
cattggaagg tccagctgct gataattttg accatttccg taatatatgg aagtctattg    1680
tacttaaaga tatgtttata tattgtgact tattattaca acatttaatc tataaattct    1740
attatgacaa taccgttaat gatatcaaga aaaattttga cgaatcctgg acacagacat    1800
taaaagaata agcctgcttg ggggtttctg ggcatctctt catgagtgcc agtcacacaa    1860
ctcttctgtg agccttctac aataaggact ttgtgtgctt cgatattttt ttagactaaa    1920
gtgaactctc tcctccacct ttggcttcag ttagttattt caaatggcaa agttattaa    1980 aaattccagt gtggaaactg gcttaaccaa caggaaaggg ttttgaggt cgcatcacta    2040 agcatcaagt ttaacaccaa catgcctgga ggattggctt agccggttgc tagggcaggc    2100
ctgtggcagg gttcttatcc cagctattaa cgctcccttc ccactcctcc aagtcctgca    2160
agtcctggat acagtgaaat gtaattgcat atcccatatc ctttgctagt atcaaatgga    2220
taaaacccaa aatggagtca taccaaatga tctcatgtat acaatacctg aatagtcttg    2280
aactgatgca ctgttagata gtatgcactt actcttcagc tattcatagt gtgcctctgc    2340
acagtgatgg aaaagaggag cactgggggga gctcggtttt caaggacaa aggagaataa    2400 gacacacaaa gaaatccaag gtagagcaga gaaaggatgg agacacagaa ggtttgcagg    2460
aacaggaagc gaaggatgct ccagtctgag ggggaggggga aagagagcct cttgagtagc    2520
cagcacctga acttggcctg gaagcttggt ggataaggca ggataaagga ggtgtggcct    2580 cttttggtatc ctcccattga taaggagct ccctgaccct tcactagacc atcatcagtc    2640
ctatggttct tagaccaata gaacacaatg gaattgattt gttccacttt ccaggttaag    2700
acttacagtc agggaagttt gtttttcttg cc                                 2732
```

<210> SEQ ID NO 3
<211> LENGTH: 2430
<212> TYPE: DNA
<213> ORGANISM: Babesia microti

<400> SEQUENCE: 3

```
aactagatgc agcaccacaa tcactaccac gtaccaatca tataccaata atgtactaat      60
aatgtaccaa taactatggt ttataaagat ggtgtcattt aaatcaatat tagttcctta     120 tattcacactc ttttttaatga gcggtgctgt ctttgcaagt gataccgatc ccgaagctgg    180
tgggcctagt gaagctggtg ggcctagtgg aactgttggg cccagtgaag ctggtgggcc     240
tagtgaagct ggtgggccta gtggaactgg ttggcctagt gaagctggtg ggcctagtga     300
agctggtggg cctagtgaag ctggtgggcc tagtgaagct ggtgggccta gtggaactgg     360
ttggcctagt ggaactggtt ggcctagtga agctggttgg tctagtgaac gatttggata     420
tcagcttctt ccgtattcta gaagaatagt tatatttaat gaagtttgtt atcttatat      480 atacaaacat agtgttatga tattggaacg agataggtg aacgatggtc ataagacta      540 cattgaagaa aaaccaagg agaagaataa attgaaaaaa gaattggaaa atgttttcc      600 tgaacaatat tcccttatga agaagaaga attggctaga atatttgata atgcatccac     660
tatctcttca aaatataagt tattggttga tgaaatatca acaaggcct atggtacatt     720
```

```
ggaaggtcca gctgctgata attttgacca tttccgtaat atatggaagt ctattgtact      780
taaagatatg tttatatatt gtgacttatt attacaacat ttaatctata aattctatta      840
tgacaatacc gttaatgata tcaagaaaaa ttttgacgaa tccaaatcta aagctttagt      900
tttgagggat aagatcacta aaaggatgg agattataac actcattttg aggacatgat      960
taaggagttg aatagtgcag cagaagaatt taataaaatt gttgacatca tgatttccaa     1020
cattggggat tatgatgagt atgacagtat tgcaagtttc aaaccatttc tttcaatgat     1080
caccgaaatc actaaaatca ccaaagtttc taatgtaata attcctggaa ttaaggcact     1140
aactttaacc gtttttttaa tatttattac aaaatagatg taataccaga tgtatacatt     1200
attatatatt acaaaattta cacattattt atgtatgaac gaacgaacat ctcagtctta     1260
aatgaagaaa ttgggataaa tatggaaata gattaaagta acatgagaaa gatgaatata     1320
atattagaat atgaaattta acagaaataa aatgaagtaa aagagtgtat tttgtaataa     1380
tttataataa attagtatac aatgattata ttacagatga ctattgatta ttgtatcaat     1440
taaatattga ttattaatga tatcatatat gtatatgtta atgattgatt tgttatacgt     1500
tgtgaatatg ttatataatg acatactata ataattaata taatgtagag gatatttttt     1560
ttaatagtat ttaatgaata ttatagttat aattataata atgtagataa aaatgacatt     1620
aatttgaatg tttaaattga aatgtatgta aaaatatgta tttataatct gaattgatta     1680 ataaatataat attctacaat taattatttt tgtaattata ataattgatt atattaatct     1740
ttgaattatt ataaataata ttatacttca ttaaattatt tcacataaat ttccaaatta     1800
ttatccttta tcttaatgtt atccaatttt acacatcttt cttcattaca atatttttt      1860 actaatcctg tatgctcata ttcatattct ttagaaatat aacgaaaatt agatgtaact     1920
tcgccactta caagtaaact accatcaata taataataat gaataccatt catgtccgta     1980
tattctttat attttttatc atattttatt ttgtgattat tccattcatt tgtatcatta     2040
ttcaatgaga gaaataatag cagaaagatc cttctataga aacataaaat tcaattaata     2100
ctggattatt atgtttgcaa gtagagatgt ttaaatcaat aacactacca gttggtaatt     2160
tagcattgtc atcaaattca attatataat cagaaatttt gattttatca atttttattcg    2220 gatgtgataa tttattttgt tctgattcat cgatcatgta tacaaatact attgttaaag     2280
gttccctatc cttataatta aagtggccaa taagattggc attaattaca ttagtagtgt     2340
gtgtatttgt aatagtatca ttagtggtac tgacagttgt tataggtttt gatttccata     2400
atgaaacatc attttatct acacaataca                                       2430
```

<210> SEQ ID NO 4
<211> LENGTH: 1991
<212> TYPE: DNA
<213> ORGANISM: Babesia microti
<400> SEQUENCE: 4

```
aatgtacaag atcaaaattt ctgattatat aattgaattt gatgacaatg ctaaattacc       60
aactgataat gttattggta tatccatcta tacttgtgaa cacaataatc cagtattaat      120
tgaattttat gtttctaaaa aaggatcaat ctgctattat ttctactcaa tgaataatga      180
tacaaataaa tggaataatc acaaaataaa atatgacaaa agatttaatg aacatactga      240
catgaatggt attcattatt attatattga tggtagttta cttgcgagtg gcgaagttac      300 atctaattt cgttatattt ctaaagaata tgaatatgag catacagaat tagcaaaaga      360
gcattgcaag aaagaaaaat gtgtaaatgt ggataacatt gaggataata atttgaaaat      420
```

-continued

```
atatgcgaaa cagtttaaat ctgtagttac tactccagct gatgtagcgg gtgtgtcaga      480
tggatttttt atacgtggcc aaaatcttgg tgctgtgggc agtgtaaatg aacaacctaa      540
tactgttggt atgagtttag aacaattcat caagaacgag ctttattctt ttagtaatga      600
aatttatcat acaatatcta gtcaaatcag taattctttc ttaataatga tgtctgatgc      660
aattgttaaa catgataact atattttaaa aaaagaaggt gaaggctgtg aacaaatcta      720
caattatgag gaatttatag aaagttgag gggtgctaga agtgagggga ataatatgtt       780
tcaggaagct ctgataaggt ttaggaatgc tagtagtgaa gaaatggtta atgctgcaag      840
ttatctatcc gccgcccttt tcagatataa ggaatttgat gatgaattat caaaaaggc      900 caacgataat tttggacgcg atgatggata tgattttgat tatataaata caagaaaga     960 gttagttata cttgccagtg tgttggatgg tttggattta ataatggaac gtttgatcga     1020
aaatttcagt gatgtcaata atacagatga tattaagaag gcatttgacg aatgcaaatc    1080
taatgctatt atattgaaga aaagatact tgacaatgat gaagattata agattaattt      1140
tagggaaatg tgaatgaag taacatgtgc aaacacaaaa tttgaagccc taatgatttt    1200
gataatttcc gactgtgaga aaaaggtat taagataaac agagatgtga tttcaagcta     1260
caaattgctt ctttccacaa tcacctatat tgttggagct ggagttgaag ctgtaactgt     1320
tagtgtgtct gctacatcta atggaactga atctggtgga gctggtagtg aactggaac     1380 tagtgtgtct gctacatcta ctttaactgg taatggtgga actgaatctg gtggaacagc    1440
tggaactact acgtctagtg gaacttggtt tggaaaatga aaaattagct ctagaaacac     1500
tttattgtta attttttaaaa acctattgaa aaatcagatt gtaaaacata attccacttc    1560
taaccatgct atgatttaac taatcaggac aaaaagaaag cataatcaac attattcatt    1620
cagtgatggt gacataattc agagaatgtg gcaattgcct cttgaagacc agagttccat    1680
ccacaggacc cacatggtta aggagagag ctaactcctg aaagttgtcc tctgactaac     1740
acattcaact tttgagtgtc tcatttatgt gttggcttct gtctaatgtg ggaaaatcat    1800
taagggctct taaatcagat cctcattctc tctattaata aactatgtga taacatcctt    1860
cagctatgaa aatgtcagga gagagtcagg aaaatggaag atattgttca ggacttaact    1920
aggtggtggc acacagttcc tttacacaga ttcctcagga caagttttag gtgaggtttt    1980
gatctatcct g                                                         1991

<210> SEQ ID NO 5
<211> LENGTH: 1271
<212> TYPE: DNA
<213> ORGANISM: Babesia microti

<400> SEQUENCE: 5
ttcactaggc caaccagctt cactaggcca accagcttca ctaggccaac cagcttcact      60
aggccaacca gcttcactag gccaaccagc ttcactaggc caaccagttc cactaggccc     120
accagcttca ctaggcccac cagcttcact aggcccacca gcttcactag gccaaccagt     180
tccactaggc ccaccagctt ctaggccca accagcttca ctaggcccac cagcttcact      240
aggcccacca gcttcactag gcccaccagc ttcactaggc ccaccagctt cactaggccc     300
accagcttca ctaggcccac cagcttcact aggcccaaca gttccactag gcccaccagc     360
ttcgcgatcg gtatcacctg caaagacagc accgctcatt aaaaagagtg taatataagg     420
aactaatatt gatttaaatg acaccatctt tataaaccat agtattggt acattattag      480
```

-continued

| | |
|---|---|
| tacattattg gtatatgatt ggtacgtggt agtgattgtg gtgctgcatc tagttgtcat | 540 |
| caatgtgcat acatcctaac taataagcta ataagctaat aagcagttat acaatttctg | 600 |
| ataattgctt ccagttattc tagaatcgat ttgaagattt ttctaagatt ggggatagac | 660 |
| gtcaatgaag gctaggttag ggttagggtt agggttaggg ttagggttta gggtttaggg | 720 |
| tttagggttt agggtttagg gttagggttt agggtttagg gttagggtt taggctccca | 780 |
| agttgtcccg tgaaagggcc gtgtctttga taaattttgc cgtcctgtac gtttcctttc | 840 |
| tagaatgcac aaaaacaaga atttggcagc tagaaacatc gttaatcacc tcttggtaga | 900 |
| gaatttcgtt gattgcgttg aaacgtttga tagccttctt ctccttcacg ccataataca | 960 |
| cctgctccaa gggcacaggc ctaaagtggc tgccaaagta gaaaagccct cggtctagat | 1020 |
| taacagtgag aaatctagcc acgtcttcgt agtttggaag cgtggccgat agaccaacta | 1080 |
| gccttacgcg ttcgggcctc tgactcaggc gggccacaat agcctccagc actgaccccc | 1140 |
| tagtgtcatg gagtaggtgt atttcatcaa ttataaccaa tctaagccgc tcaagcaggg | 1200 |
| gctcattgcc tgttttacgt gtaactacgt caaacttctc tggcgtagtt acaattatat | 1260 |
| gcgttttctc a | 1271 |

<210> SEQ ID NO 6
<211> LENGTH: 1821
<212> TYPE: DNA
<213> ORGANISM: Babesia microti

<400> SEQUENCE: 6

| | |
|---|---|
| taaaccctaa accctaaac cctaaaccct aaacccctaaa ccctaaaccc taaaccccta | 60 |
| aaccctaaac cctaaaccct aaaccctaaa ccctaacccc aaacctaaaa ccctaaaccc | 120 |
| taaaccctaa accctaaccc taaccctaac cctaacccta acctagcctt cattgacgtc | 180 |
| tatccccaat cttagaaaaa tcttcaaatc gattctagaa taactggaag caattatcag | 240 |
| aaattgtata actgcttatt agcttattag cttattagtt aggatgtatg cacattgatg | 300 |
| acaactagat gcagcaccac aatcactacc acgtaccaat catataccaa taatgtacta | 360 |
| ataatgtacc aataactatg gtttataaag atggtgtcat ttaaatcaat attagttcct | 420 |
| tatattacac tcttttaat gagcggtgct gtctttgcag gtgataccga tcgcgaagct | 480 |
| ggtgggccta gtggaactgt tgggcctagt gaagctggtg ggcctagtga agctggtggg | 540 |
| cctagtgaag ctggtgggcc tagtgaagct ggtgggccta gtgaagctgg tgggcctagt | 600 |
| gaagctggtg ggcctagtga agctggtggg cctagtgaag ctggtgggcc tagtggaact | 660 |
| ggttggccta gtgaagctgg ttggcctagt gaagctggtt ggcctagtga agctggttgg | 720 |
| cctagtgaag ctggttggcc tagtgaagct ggttggccta gtgaacgatt tggatatcag | 780 |
| cttcttggt attctagaag aatagttata tttaatgaaa tttatttatc tcatatatac | 840 |
| gaacatagtg ttatgatatt ggaacgagat agggtgaacg atggtcataa agactacatt | 900 |
| gaagaaaaaa ccaaggagaa gaataaattg aaaaagaat tggaaaaatg ttttcctgaa | 960 |
| caatattccc ttatgaagaa agaagaattg gctagaataa ttgataatgc atccactatc | 1020 |
| tcttcaaaat ataagttatt ggttgatgaa atatccaaca aagcctatgg tacattggaa | 1080 |
| ggtccagctg ctgatgattt tgaccatttc cgtaatatat ggaagtctat tgtacctaaa | 1140 |
| aatatgtttc tatattgtga cttattatta aaacatttaa tccgtaaatt ctattgtgac | 1200 |
| aataccatta atgatatcaa gaaaattttt gacgacatag agaaattggg ctgttttcaa | 1260 |
| gctagaagct tcctccctgt taactaatgt attcatggtg ccagaaggtg ctatgcaggt | 1320 |

-continued

```
tgctagggaa tcaaattcat caatagtcct gcccaagagt agtgtgttaa ctggcggtgc    1380
aagatgtgcc cttttgatgca gtagtggcat gcttgtttgt ggggtaaccc agtgctttct   1440
gattgaggtc tactccacag gaggaataga tacctgcttc tgtaaacttg gtcaaaactt    1500
atgactgcac atgaagacag agtggaaaag acctgaaaac acacgcggg tcaggactga    1560 ggaagacagg gttagtatta gagagatttg gggaaaaaaa gagttagcaa atatagagtg   1620
tgatagtcta atgggggat gaatggtatc aaaatgaatt atttatatgt ataaaactga    1680 caattttta attgtgaaaa ggaatgcaat ccgacccatc tgggggaatt ctagctagca    1740
tcagtgagag aagaggcaag gtgttaggaa atcgtgcaga acatgctcat ccaggcttta    1800
tttctccatt tacatctaga g                                              1821

<210> SEQ ID NO 7
<211> LENGTH: 4223
<212> TYPE: DNA
<213> ORGANISM: Babesia microti

<400> SEQUENCE: 7
catcacaatt attggctgtt acatcactat agtgctgtat gtaaaaaatt ataaagtgtg     60
acatcattat aatgcaatat gacatcacaa ttatatactg tgacttcact atcttgcact   120
ttaacatcac aattatacat tgtgacatca atatactgca ctatgacatc acgattattg   180
actgtgacat caatacattc tctatgaaca cagttataca ctctgacatc actagcttgc   240
actgtgacat gacaattaaa aactgtgaca tcaatataat ggactgtgac ctacaattat   300
tcactgtgaa accacaacac tgcaattgtg tataattggg atgggtactg atctgctgcc   360
cgaggctcaa tagattacct aggcctcctc actgacaccc acattcaggg ggtcttgatc    420
agtcccatga tggattccca ggctgatgcc tgggattcaa gagttaacct ttgtctggtc    480
agctctttct gggggttaaa cggattaaat gttttaataa taagtcacaa tatagaaaca    540
tatttttagg tacaatagac ttccatatat tacggaaatg gtcaaaatca tcagcagctg    600
gaccttccaa tgtaccatag gctttgttgg atatttcatc aaccaataac ttatattttg    660
aagagatagt ggatgcatta tcaattattc tagccaattc ttctttcttc ataagggaat   720
attgttcagg aaaacatttt tccaattctt ttttcaattt attcttctcc ttggttttt    780 cttcaatgta gtctttatga ccatcgttca ccctatctcg ttccaatatc ataacactat    840
gttcgtatat atgagataaa taaatttcat taaatataac tattcttcta gaataccaaa    900
gaagctgata tccaaatcgt tcactaggcc aaccagcttc actaggccaa ccagcttcac    960
taggccaacc agcttcacta ggccaaccag cttcactagg ccaaccagct tcactaggcc   1020
aaccagcttc actaggccca ccagcttcac taggcccacc agcttcacta ggcccaccag   1080
cttcactagg cccaacagtt ccactaggcc accagcttc actaggccca ccagcttcac    1140
taggcccacc agcttcacta ggccaccag cttcactagg cccaccagct tcactaggcc    1200
caccagcttc actaggccca ccagcttcac taggcccaac agttccacta ggcccaccag   1260
cttcgcgatc ggtatcacct gcaaagacag caccgctcat taaaaagagt gtaatataag    1320
gaactaatat tgatttaaat gacaccatct ttataaacca tagttattgg tacattatta   1380
gtacattatt ggtatatgat tggtacgtgg tagtgattgt ggtgctgcat ctagttgtca   1440
tcaatgtgca tacatcctaa ctaataagct aataagctaa taagcagtta tacaatttct   1500
gataattgct tccagttatt ctagaatcga tttgaagatt tttctaagat tgggataga    1560
```

-continued

```
cgtcaatgaa ggctaggtta gggttagggt tagggttagg gttagggttt agggtttagg    1620
gtttagggtt tagggtttag ggttagggtt tagggtttag ggtttagggt ttagggttta    1680
ggggtttagg gtttagggtt tagggtttag ggtttagggt ttagggttta gggaaggctg    1740
agaaccactg acttagactt tccaagactt tgtcatctta tgacttgccg gttgcctcgt    1800
ttctccacac agcaacctat gttctctctt attacagttt ctgtgggaca tgtcatgctt    1860
ccagcttcga gaatggaagc ctattgtctt aatgggtgag caaagtgggc ccattcatta    1920
atcacagact aatccaaaag gaaatgtgac acctgaccta agtccgacca ataggagcca    1980
ggaaagctca cttctggaat tgtgacttag atatcacgga tgcatacaga ctcttttttcc   2040
tgctgaaaca aatggtgagg acctgtccac ccttgtggga agcttgcagt gtaagattct    2100
aatccatatt ggggaaataa ggctgagaag agagagttcc aggccttgtg acagaatcta    2160
atccctggat aaagtctctc tttttacaaa gaacatcagt gttgcaagct ccaaattcct    2220
gttcttactt tcttgagtct gtttttcttta tgtataaccc aaagcacttt aactgacaca    2280
gctgtgaagt gagaatattt catagaaatc ctattgtttt gatgtcttct aaaaaagaaa    2340
aaaagcaatg atctgtaaca tttttttaact taaataatta gattgattta agtgacatca    2400
aaacatctgg aaaatggtgt ggacacaaat tcactagaga gccatatttt ttgctaacta    2460
attgagaaat taatcactgg caagtctttg gtaaaagtat cacctcagtc atgatctctc    2520
ctgccttcat gacattttcc tcattggtgt gaggatgcta ttctgctttc tatgtgacca    2580
ggaaatagtg ctgtcttctg tctagttatg atttaggttg tacaccaggt tttcacatat    2640
gttccctaac gtctgtagta ggaccaggga ctggttggct tcaagttgtt ggatatggtt    2700
accttaagtc attcatgtac aggaactcat ttgagatgat aggaaatgaa gtgaaagatt    2760
ttcttgcccc tgttaagtaa gataaaaagg attgttatga tggggcagga gcagatctat    2820
ttccaataaa cagaatttga agtgtttgtg tgatattcag atacctcatt gtcatttgaa    2880
tgaattactc ctgctctcag tgaagatgtc taagctgcaa ataagaaatg gagagcgctg    2940
tcagaagtca gatggaattg agaatagggg cctggctgca atctgtggag actgcctaaa    3000
gcagctagat aagaaactag cagctgggga gagaaagatc gaatttagtc ggcctgtttt    3060
atattttctt ataaaaaata actgcttcga aatgtttgag aagatagagg caatgagcag    3120
aaagttgttc cttaaatcag ttatagaatg aacacataca cgggcactca gatcaagcca    3180
tgctgagctt gagacaccgg gtgacgcgtg acttgtttat tcccaggctg caaggagag    3240
taaatgaagt aacgggaagg cccggtgtgg taggcacact cctgcctggc accatctgct    3300
gcttttgtcc ctgttactcc ttgttccttt ccctcctttt ctccctccct tcctccctcc    3360
ctctctccct ccttcacact tctgtcttta tttcctcctg ggagttaatt ggtggtagcc    3420
cctctgtgct gttctttcgg gggtgccttt aatttcgaca atacaatgcc atccatgggg    3480
gcatttata tacagtaata attgtcattg atgtggccat aaggtacttt tttgtggtac     3540
ccttcttgaa cagaacagac acagaagggc gtgcgtgcgt gcgtgcgtgc gtgcgtgcgt    3600
gcgtgtgtgc gtgtgtgcgt gcgtgtgtgc gtgtgtgcgt gcgtgcgtgt gtgcgtgcgt    3660
gcgtgtgtgc gtgtgtgtgt gtgtgtgtgt gtgtgtgtgt gtgtgtgtgt gtgtgttggg    3720
atggggtggg gagcgctagc ttcctacttg ttgtagggtg atgaggtttt atatagtctg    3780
tttctgagac agttaccaaa tccagctggg ttactttttt tttggttttt tatgagacag    3840
ggtttctctg tattgttttg gaggctgtcg gtccagcctg gtctcgaact cacagagatc    3900
cgcctgcctc tgcctcccga gtgctgggat taaaggtgtg cgccaccacc gcccggcccc    3960
```

```
agctgggtta cttatcactc agtggatctt tctcttttct ttgtaagaag aactttgcat    4020
tgtgggtcgt catggaagaa cacttggaaa ggtacccttt ctgccccacc cgtttattga    4080
atgagtcttt ttttttttta attaaatagc agaactttgg ggaaagattt agaaaaggcc    4140
cttttcatat tataatacga ggtataggat ggtttaagat aagagactt ttgttagctg     4200 ttatcagttg agaaaggcac gag                                            4223

<210> SEQ ID NO 8
<211> LENGTH: 2287
<212> TYPE: DNA
<213> ORGANISM: Babesia microti

<400> SEQUENCE: 8
ttataaacat atctaaatat tttaataata atgatgaaat ttaacataga taagataata     60
ttaatcaatt taatagtatt attgaatcga aatgtagtgt attgtgtgga tacaaataat    120
agttcattaa ttgaatcaca accagtaaca actaacattg acactgataa tacaattaca    180
acaaataaat acactggtac tataattaat gccaatattg ttgagtaccg tgaatttgag    240
gatgaacctt taacaatagg gtttagatac actatagata aatcacaaca aaataaatta    300
tcacatccaa ataaaattga taaaatcaaa ttttctgatt atataattga atttgatgac    360
aatgctaaat taccaactga taatgttatt tgtatatcca tctatacttg caagcataat    420
aatccagtat taattagatt ctcatgttct atagaaaaat attactacca ttacttctac    480
tcaatgaata atgatacaaa taaatggaat aatcacaaat taaaatatga taaaacatac    540
aatgaatata ctgacaataa tggtgttaat tattataaaa tctattatag tgataaacag    600 aattcccta ctaatggaaa tgaatatgag gatgtagcat tagcaagaat acattgtaat     660
gaagaaagat gtgcaaatgt aaaggtagat aaaattaaat ataagaattt ggaaattat     720 gtgaaacagt taggtactat aattaatgcc aatattgttg agtaccttgt atttgaggat    780
gaacctttaa caatagggtt tagatacact atagataaat cacaacaaaa tgaattatca    840
catccaaata aaatttataa aatcaaattt tctgattata taattgaatt tgatgatgat    900
gctaaattaa caacaattgg tactgttgaa gatataacca tctatacttg caagcataat    960
aatccagtat taattagatt ctcatgttct atagaaaaat attactacta ttacttctac   1020
tcaatgaata ataatacaaa taaatggaat aatcacaact aaaatatga taatagattc    1080 aaagaacata gtgacaagaa tggtattaat tattatgaaa tctcagcttt caaatggagt    1140
ttctcttgtt ttttcgttaa taaatatgag cataaagaat tagcaagaat acattgtaat    1200
gaagaaagat gtgcaaatgt aaaggtagat aaaattaaat ataagaattt ggaaatttat    1260
gtgaaacagt taggtactat aattaatgcc aatattgttg agtaccttgt atttgaggat    1320
gaacctttaa caatagggtt tagatacact atagataaat cacaacaaaa tgaattatca    1380
catccaaata aaatttataa aatcaaattt tctgattata taattgaatt tgatgatgat    1440
gctaaattaa caacaattgg tactgttgaa gatataacca tctatacttg caagcataat    1500
aatccagtat taattagatt ctcatgttct atagaaaaat attactacta ttacttctac   1560
tcaatgaata ataatacaaa taaatggaat aatcacaact aaaatatga taatagattc    1620 aaagaacata gtgacaagaa tggtattaat tattatgaaa tctcagcttt caaatggagt    1680
ttctcttgtt ttttcgttaa taaatatgag cataaagaat tagcaagaat acattgtaat    1740
gaagaaaaat gtgtaaatgt aaaggtagat aacattggga ataaaaattt ggaaatttat    1800
```

```
gtgaaataat ttaatgaagt ataatattat ttataataat tcaaagatta atataattaa    1860
ttattataat tacaaaaata attaattgta gaatattata ttattaatca attcagatta    1920
taaatacata ttttttacata catttcaatt taaacattca aattaatgtc attttttatct  1980 acattattat aattataact ataatattca ttaaatacta tttaaaaaaa tatcctctac    2040
attatatcaa tcaatataat atacaattat ataatatatt cacaatgtat aacaatcaac    2100
cctaacatgt acatacataa tatcattact aatcaatatt taattaataa aatatttaat    2160
agtcatctgt aatataatca ttgtatacta atttattata aattattaca aaatacactc    2220
ttttacttca ttttatttct gttaaatttc atattctaat attatattca tctttctcat    2280
gttactt                                                              2287
```

<210> SEQ ID NO 9
<211> LENGTH: 2784
<212> TYPE: DNA
<213> ORGANISM: Babesia microti

<400> SEQUENCE: 9

```
cactgctttc gcagcgtttc ttgcttttgg gaatatctca cctgtacttt ctgctggtgg     60
tagtggtggt aatggtggta atggtggtgg tcatcaagag caaaataatg ctaatgatag    120
tagtaatccc accggagccg gtggacaacc caataacgaa agtaagaaaa aggcagtaaa    180
acttgacttg gacctcatga agaaacaaa gaatgtttgc accactgtta atactaaact    240
agtcggaaaa gcaaagagca aattaaacaa attagaaggt gaatcccata aggagtatgt    300
agctgagaaa acgaaggaga tagatgagaa aaataagaaa tttaacgaga atcttgttaa    360
aatagagaaa aagaagaaaa ttaaggttcc tgccgatact ggtgctgaag tggatgctgt    420
tgatgatggt gttgcgggtg cactatccga tttatcctcc gatatctccg ctattaagac    480
tctcaccgac gatgtatccg agaaggtttc tgaaaacttg aaagatgatg aggccagtgc    540
aacagaacac actgatataa agaaaaagc caccctgctt caagagtctt gcaacggaat    600
tggcactatc ctagataagt tggccgaata tttaaataat gatacaactc aaaatatcaa    660
gaaagaattt gatgaacgca agaagaatct caccctttg aagacaaagg tagaaaataa    720
ggatgaagat tatgttgatg ttaccatgac atcaaaaca gatctgataa tacactgttt    780
aacttgcaca aacgatgcac acggactgtt tgatttcgaa tcgaagagct tgataaaaca    840 aaccttttaaa ttgaggtcca aagatgaagg tgaactctgc taatttagat tttagatggg    900
ccatgtatat gttaaacagc aagattcatc ttatagaaag cagtttgatc gataacttca    960
ccttggataa tccatccgca tacgaaattt tacgcgttc ttataactca aatgaatttc    1020
aagtacaatc accgcagaac attaacaatg aaatggaatc ttcaacgccc gaatccaata    1080
tcatttgggt tgtacatagt gatgttataa tgaaaaggtt caactgtaaa aatcgcaaat    1140
ctctcagtac tcattcactc actgaaaatg atattctcaa gtttggccgt atagaactct    1200
ctgttaaatg tataattatg ggcgcaggta tcactgcatc tgatcttaat ctaaagggat    1260
tggggtttat tagtccagat aaacaatcaa ctaatgtatg taactatttt gaagatatgc    1320
atgaatctta tcatattctt gatacacaaa gggcctcgga ttgtgtatca gatgatggcg    1380
ctgatattga tatatccaac ttcgacatgg tccaagacgg taacataaat tctgttgacg    1440
ctgattctga aacatgtatg gcaaactctg gcgtaacggt caataatact gaaaatgtta    1500
gtaatagtga gaattttgga aaattaaaat cattggtaag caccaccact cctttgtgcc    1560
gtatttgcct gtgtggtgaa tcagaccctg ggccactagt aaccccttgc aattgcaagg    1620
```

-continued

```
ggtccctaaa ttatgtccat cttgaatgcc taaggacttg gattaaaggg cggttgtcaa      1680
ttgtgaagga tgatgatgct tccttttcct ggaaagagct atcatgtgag ctatgcggga      1740
agccgtatcc atcggtccta caagtagatg atacagagac taatttgatg gatataaaaa      1800
aaccggatgc accatatgtg gtattggaaa tgagatcaaa ttctggtgat gggtgtttcg      1860
ttgtttctgt agctaaaaat aaggcgatta ttggacgggg gcatgaaagt gacgttaggt      1920
tgagtgatat ttcagtgtca cgaatgcatg cttctttgga attggatggt ggaaaagtag      1980
tgatacatga ccagcaatct aagtttggta cactcgttag ggccaaagcg cctttttcaa      2040
tgcctataaa gggtcccatc tgtctacagg taagcatttt ctttttgaac ttgaaaatat      2100
ctactcatag tctaaccatg gagagggca tggaacatgt ccttctctaa tatttccaaa       2160
aaggatctat gcctgataac cttggtattg aaggtggctt tctcaaagtg agacattcca      2220
tttctgttgt tggagctatc ctatctgagg ttagtgttct ggtaaacatt cctagaaaac      2280
tcataaagca gaaatctgtg tgtatactaa attgcacaga gaactccacg tgtgtgctag      2340
acttcacaga gaactctgtg tgtgtgctaa actgcataga gaagaacatg ttgagtgcat      2400
catggttgag ggaaattgct ttatataaaa gatttatttt cctaaggtaa cttaggatta      2460 attttttctga aagcttagtt ttggtgagca caattgtgat ctttgtttct cagatggtcg      2520
ggaaggcact cccagaaagc aggtggatac acactacact gcatgctaca ctctgtagac      2580
taggagtatc gttttcacac ttatgaaata gtcaccatgc tgggcacaaa tatcttttta      2640
tacaccatat attgttcatg ttcaggtcca catttcaatt tgtatgtgaa aagcatccgg      2700
ggctgtctga taaacacata gaaatgaagg aaacagtgta tgtaactgaa gccttcagtc      2760
ctttgcaatt tctttgattc ttag                                             2784
```

<210> SEQ ID NO 10
<211> LENGTH: 3701
<212> TYPE: DNA
<213> ORGANISM: Babesia microti

<400> SEQUENCE: 10

```
acctatttat aatatagtat attactggtt tgttttaaat cgaaaaaatg tattgtattg       60
aagaatgaaa ttatttattt atcatgatta tcatatttct aaatattaaa atctagtaac      120
ggttgcttga atttatttt aaattatatg tagtagtatt aaaatgtgtt atatataagt       180
agtgttctaa atcatcatta gtaatattgt ataaattaat tgtaaaaatt gcgatactac      240
aattaatcaa caattaaaat atatcagtat agataattta ataaataat tagataagat       300 cttaaggatt aaatgacgaa tttagaatga taaataatca tcataggcat ttgttataat      360
atcattaatt atattcatgt ggttataatt ataaagtat atatagtttt gtaattgtaa       420
tgatataaaa ttagaacaga tataattaat aattcaaata ttatattaat tttattatat     480
atgattatta ttgatattta tataattaca tattgttatt gtatcattta atgattatat     540
atcaatatcc atatatatat ataataattg aattataatt aaattaattg gcatattaca     600
tttataataa tatattatta gtcaatatga catcatatta tattatccat catgattgtg     660
aatgtaacta gaacattgat tattatatta atcacatat taatactgat tataataata     720
tcattgataa tctaataata tagtattatc tctaataata ttgtattatc tctaatatta    780
tggtataata gatactgtga aaataaattc aactggagat aaggaaacca ttttgtatag    840
atattttata caaattatta tgaaataatc taaataaatg acaaaaaatc gattatacaa     900
```

```
atcacattaa tgacaaacaa acttgtatac atatattgat taacattaca aaactaaatt        960
ataatattta gattgataat tgttataata cttaacaata ttctactttt taatataatt       1020
ttttattcaa taatatactc tttcatattt tgtactattt tatataatca tatatattat       1080
ataattatat atatttgata attgaatata tcaataatga tgatatacat gaatatgcat       1140
atataccoca tataatgtta ttatatttag tgcttacatt attaattata aatatattta       1200
aataattaaa taataatgaa aattaacata gacaatataa tattaatcaa tttgataata       1260
ttattgaatc gtaatgtagt atattgtgtg gataaaaatg atgtttcatt atggaaatca       1320
aaacctataa caactgtcag taccactaat gatactatta caaataaata cactagtact       1380
gtaattaatg ccaattttgc tagctaccgt gaatttgagg atagggaacc tttaacaata       1440
ggatttgaat acatgatcga taaatcacaa caagataaat tatcacatcc aaataaaatt       1500
gataaaatca aaatttctga ttatataatt gaatttgatg acaatgctaa attaccaact       1560
ggtagtgtta atgatatatc catcattact tgcaagcata ataatccagt attaattaga       1620
ttctcatgtt aatagaaagg atctatctgc tattatttct acttattgaa taatgataca       1680
aataaatgga ataatcacaa attaaaatat gataaaacat acaatgaaca tactgacaat       1740
aatggtatta attattataa aatcgattat agtgaatcta cagaacctac taccgaatct       1800
actacctgtt tttgttttcg caaaaaaaat cataaatctg agcgtaaaga attagaaaat       1860
tataaatatg agggtacaga attagcaaga atacattgta ataaagggaa atgtgtaaaa       1920
ttgggtgaca ttaagataaa ggataagaat ttggaaattt atgtgaaaca gttaatgtct       1980
gtaaatactc cagtaaattt tgacaaccct acatcgatta atctaccaac tgtcagtact       2040
accaatgata ctattacaaa taaatacact ggtactataa ttaatgccaa tattgttgag       2100
tactgtgaat ttgaggatga acctttaaca ataggtttta gatacactat agataaatca       2160
caacaaaata aattatcaca tccaaataaa attgataaaa tcaaattttt tgattatata       2220
attgaatttg atgatgatgt taaattacca acaattggta ctgtcaatat tatatatatc       2280
tatacttgcg agcataataa tccagtatta gttgaattta tagtttctat agaagaatct       2340
tactactttt acttctactc aatgaataat aatacaaata aatggaataa tcacaaatta       2400
aaatatgata aagattcaa aaaatatact aagaatggta ttaattgtta tgaatatgta       2460
cttcgtaaat gcagttctta tactcgtaaa aatgaatatg agcataaaga attagcaaga       2520
atacattgta atgaagaaaa atgtgtaaat gtaaaggtag ataacattga gaaaagaat       2580
ttggaaattt atgtaaaata atttaacgaa gtgtaatatg taaaatagtt taatgaagta       2640
taatattatt taaaataatt caaaatttca gaaattaata taattaatta ttataaaatac       2700
aaaataatta attacaaatg tgtattgtta gttatttcag attgtaaata catattttac       2760
atacattttt attaaaactt tcaaattaat atttcatttt ttataagcat tattataatt       2820
atatactata attatcagtc atcaaataat atccaaagtt atcctctaca ttatatcaat       2880
catacagtat acaattatat aaaatattaa caacatataa caaccaacat taatatatac       2940
ataatatctt tattaatcaa tatttaatca atacaataat taatagttaa ctaactatac       3000
acatagtgta tactaaatta ttataaatta tatgttataa ttacaaaaac gtcatttact       3060
tattttattt cagttatgtt tcatagtcta atttagattt ggtgaaacgc atctggctga       3120
tgtgctggtg agcaagcagt tccacgaagc aaacaatatg actgatgcgc tggcggcgct       3180
ttctgcggcg gttgccgcac agctgccttg ccgtgacgcg ctgatgcagg agtacgacga       3240
caagtggcat cagaacggtc tggtgatgga taaatggttt atcctgcaag ccaccagccc       3300
```

-continued

```
ggcggcgaat gtgctggaga cggtgcgcgg cctgttgcag catcgctcat ttaccatgag   3360
caaccccgaa ccgtattcgt tcgttgattg gcgcgtttgc gggcagcaat ccggcagcgt   3420
tccatgccga agatggcagc ggttacctgt tcctggtgga aatgcttacc gacctcaaca   3480
gccgtaaccc gcaggtggct tcacgtctga ttgaaccgct gattcgcctg aaacgttacg   3540
atgccaaacg tcaggagaaa atgcgcgcgg cgctggaaca gttgaaaggg ctggaaaatc   3600
tctctggcga tctgtacgag aagataacta aagcactggc ttgataaata accgaatggc   3660
ggcaatagcg ccgccattcg gggaatttac ccctgttttc t                        3701
```

<210> SEQ ID NO 11
<211> LENGTH: 1287
<212> TYPE: DNA
<213> ORGANISM: Babesia microti

<400> SEQUENCE: 11

```
ctcgtgccgc tcgtgccgat tattataaat atttagttga tgaatatagt tctcccaggg     60
aggaaagaga attagcaaga gtacattgta atgaagaaaa atgtgtaaaa ttggatggca    120
ttaagtttaa ggataagaat ttggaaattt atgtgaaaca gttaatgtct gtaaatactc    180
cagttgtatt tgacaacaat acattgatta atccaactag cagcagtggt gccactgatg    240
acataacata tgaattatcg gtggaatcac aacctgtacc aactaacatt gacacaggta    300
ataatattac aacaaataca tcaaataata atctaattaa agctaaattt ctttataatt    360
ttaatcttcc tggtaaacct tcaacaggac tatttgaata cactatagat aaatcagaac    420
aaaataaatt atcacatcca aataaaattg ataaaatcaa attttctgat tatataattg    480
aatttgatga tgatgctaaa ttaccaacaa ttggtactgt caatattata tccatcatta    540
cttgcaagca taataatcca gtattagttg aatttatagt ttctacagaa atatattgct    600
actacaatta cttctactca atgaataata atacaaataa atggaataat cacaaattaa    660
aatatgataa aagatataaa gaagaatata cagatgataa tggtattaat tattataaat    720
taaatgatag tgaacctact gaatctacag aatctactac ctgtttttgt tttcgcaaaa    780
aaaatcataa atatgaaaat gagcgtacag cattagcaaa agaacattgc aatgaagaaa    840
gatgtgtaaa ggtagataac attaaggata ataatttgga aatttatcta aaataattta    900
acgaagtata atattattta taataattca aaatttcaga aattaatata attaattatt    960
ataaatacaa aataattaat tacaaatgtg tattgttagt tatttcagat tgtaaataca   1020
tattttacat acatttttat taaaactttc aaattaatat tttcattttt ataagcatta   1080
ttataattat atactataat tatcagtcat caaataatat ccaaagttat cctctacatt   1140
atatcaatca tacagtatac aattatataa aatattaaca acatataaca accaacatta   1200
atatatacat aatatcttta ttaatcaata tttaatcaat acaataatta atagttaact   1260
aactatacac atagtgtata ctaaatt                                        1287
```

<210> SEQ ID NO 12
<211> LENGTH: 572
<212> TYPE: DNA
<213> ORGANISM: Babesia microti

<400> SEQUENCE: 12

```
cttcattgac gtctatcccc aatcttagaa aaatcttcaa atcgattcta gaataactgg     60
aaacaattat cagaaattgt ataactgctt attagcttat tagcttatta gttaggatgt    120
```

-continued

| | |
|---|---|
| atgcacattg atgacaacta gatgcagcac cacaatcact accacgtacc aatcatatac | 180 |
| caataatgta ctaataatgt accaataact atggtttata agatggtgt catttaaatc | 240 |
| aatattagtt ccttatatta cactcttttt aatgagcggt gctgtctttg caagtgatac | 300 |
| cgatcccgaa gctggtgggc ctagtgaagc tggtgggcct agtgaagctg gtgggcctag | 360 |
| tggaactgtt gggcccagtg aagctggtgg gcctagtgaa gctggtgggc tagtggaac | 420 |
| tggttggcct agtgaagctg gtgggcctag tgaagctggt gggcctagtg aactggttg | 480 |
| gcctagtgaa gctggttggt ctagtgaacg atttggatat cagcttcttc cgtattctag | 540 |
| aagaatagtt acatttaatg aagtttgttt at | 572 |

<210> SEQ ID NO 13
<211> LENGTH: 2338
<212> TYPE: DNA
<213> ORGANISM: Babesia microti

<400> SEQUENCE: 13

| | |
|---|---|
| ctcgtgccga atcttagaaa aatcttcaaa tcgattctag aataactgga aacaattatc | 60 |
| agaaattgta taactgctta ttagcttatt agcttattag ttaggatgta tgcacattga | 120 |
| tgacaactag atgcagcacc acaatcacta ccacgtacca atcatatacc aataatgtac | 180 |
| taataatgta ccaataacta tggtttataa agatggtgtc atttaaatca atattagttc | 240 |
| cttatattac actcttttta atgagcggtg ctgtctttgc aagtgatacc gatcccgaag | 300 |
| ctggtgggcc tagtggaact gttgggccca gtgaagctgg tgggcctagt gaagctggtg | 360 |
| ggcctagtgg aactggttgg cctagtgaag ctggtgggcc tagtgaagct ggtgggccta | 420 |
| gtggaactgg ttggcctagt gaagctggtt ggtctagtga acgatttgga tatcagcttc | 480 |
| ttccgtattc tagaagaata gttacattta tgaagtttg tttatcttat atatacaaac | 540 |
| atagtgttat gatattggaa cgagataggg tgaacgatgg tcataaagac tacattgaag | 600 |
| aaaaaaccaa ggagaagaat aaattgaaaa agaattgga aaatgttttt cctgaacaat | 660 |
| attcccttat gaagaaagaa gaattggcta gaatatttga taatgcatcc actatctctt | 720 |
| caaaatataa gttattggtt gatgaaatat caaacaaggc ctatggtaca ttggaaggtc | 780 |
| cagctgctga taattttgac catttccgta atatatggaa gtctattgta cttaaagata | 840 |
| tgtttatata ttgtgactta ttattacaac atttaatcta taaattctat tatgacaata | 900 |
| ccattaatga tatcaagaaa aattttgacg aatccaaatc taaagcttta gttttgaggg | 960 |
| ataagatcac taaaaaggac gtgtatgtaa atgatcacta acgggctcc acatatctat | 1020 |
| tactggggta gatattataa gttatggata agtaaattta tggcgataga ttccaacaaa | 1080 |
| tttgtggtta gtagcgacaa tgattatggc tagtgtgtgg agtacttatg agtgaatgat | 1140 |
| tgtagtggtg gctagcagtg agtatagtta ggtaatccct acacacccat ttaaataaga | 1200 |
| tgcaaatagc atttaaattg acatatattg tgtgtatgtc cacgtttatt gcgtttccat | 1260 |
| gacgtatctg ctgaggtgtg tcttgtgtat ctaagtacca gacacagcac ttaaattgtt | 1320 |
| atgggcatga cgatggatgt taaaggttta tacactccaa aggcacgttc ttctgctagg | 1380 |
| gaaacgaggg acaagttcga ttttgctata caaagcaagt ttcactcccct ggactttaca | 1440 |
| ctggatgact ttgatatagg tgcattcgtg gtaaacctca aaatttactc agggcgatgg | 1500 |
| tgccccatggg caggtttttt tggcaaggga acgacgtacc ggtttttatt gcgtgttaaa | 1560 |
| atgcatttt aaatcacaac ttgtgaagta attgcctaat aatcacacag aaatggacag | 1620 |
| gaagctattt tcaagcggga aatcgaattg cacgggcatc tgagacatcc aaacatagca | 1680 |

```
tggtatgtac atatttatcc agcttgtata cctggttcac tagccctact atgatattca    1740
tagtgatgga atattgttac aatggcgatc tatttaatta tatgtcaaaa catggccaac    1800
tgagtgaaga aagggtatca gagtatacag atatttacat agaattttgt tcgaagtcat    1860
ttgggccatt agaagctgcc acgacaaacg catagcgcac ttggatatta aaccagtaag    1920
gttctatgtt acagaggaga atatattatt ggaccatgaa aacaggtgta aattggcgga    1980
ctttggattc tctgcacaca tagggcattt gtaccgctca acggagtgc tcatcatcgt      2040 ggcacgcatg gtaacacgca attwatggca gattattggt ctccggagca gtgtgccaaa    2100
catttgggtc tggggttgaa gtatggggag tatgatgaac aaagcgacat atgggcgttg    2160
ggcatattgg cagttgaatt gtttattgga taccctccat ttggatctac tactgaagag    2220
cccaacaatg tgattatgaa cagaatccac acttaccact ggaccaaaca tgtacttta     2280 tctattacgc agatttttga aatgaagagg gaaaaacatc tactctcgtc gacgcctg      2338

<210> SEQ ID NO 14
<211> LENGTH: 729
<212> TYPE: DNA
<213> ORGANISM: Babesia microti

<400> SEQUENCE: 14
ttgcctggac cttctctgtc ctagaattac aggaattctc ttatactgtt aatacaaaa      60 cacttggaag aatttcacca attgcatatg aaacatggaa tccaagagac caaaatttaa    120
aaccttgaaa tagaagcact tatgccaata ttggaaatta cttagtgaag tgatccaaag    180
tactgatttg gtcagaagac atcaccaggg cactagctgg cctagtgacc tgagtatttg    240
tgaaagctga tttaatgtt gagaacatga aggaagcagt attgaggtaa tggaatcttg    300
tagattatag tagaagccaa ctgagaccaa gaaatgtacg gtaggaatga ataaggtct     360 tgggtggtca ttgcatggag ctgtgaaagt gaagcgttgt tggggtatag attcgcaagt    420 cttgggcat gactatgtgg ggttaccaag gttaggttaa ctgaggtgga aagatccact     480
ctaaatgggg gagttaccat ttcatgtgct gggatcccag agatgtcaaa ggagaaaata    540
agctattgaa taagagcatc tatatcccttt gcttcttggc tatggatgtt atgtgactag    600
tcatctctta gtcttacctt caccattata acaagatttt ctagaacttt gggttaaatt    660
aaatccttta ttcctcacgt tgctgtctta gttactttcc tgttgctttg ataaagcatt    720
ctggccaag                                                             729

<210> SEQ ID NO 15
<211> LENGTH: 1448
<212> TYPE: DNA
<213> ORGANISM: Babesia microti

<400> SEQUENCE: 15
acatgttgac ttttggaaat atacgttttc ataatataaa tctcccacca ttttcattgg     60
gcataattca ctcgattacg gtagaaaagg cgattaactc tgaagatttt gacggaatac    120
aaacactttt acaagtgtct atcattgcta gttacggtcc atctggcgat tacagtagtt    180
ttgtgttcac tccagttgta acagcagaca ccaacgtttt ttacaaatta gagacggatt    240
tcaaacttga tgttgatgtt attactaaga catcactaga attgcccaca agtgttcctg    300
gctttcacta caccgaaact atttaccaag gcacagaatt gtcaaaattt agcaagcctc    360
agtgcaaact taacgatcct cctattacaa caggatcggg gttgcaaata atacatgatg    420
```

-continued

| | |
|---|---|
| gtttgaataa ttcgacaatt ataaccaaca aagaagttaa tgtggatgga acagatttag | 480 |
| ttttttttga attgctccct ccatcggatg gcattccac cttgcgatca aaattatttc | 540 |
| ccgtcctgaa atcaattcca atgatatcta ccggggttaa tgaattactg ttggaagtac | 600 |
| tcgagaaccc ctctttccct agtgcaatta gcaattacac cggactgaca ggccgactta | 660 |
| acaaattact tacagtttta gacggtattg ttgatagcgc cattagtgtc aagactacag | 720 |
| aaactgtccc tgacgacgca gaaacttcta tttcttcatt gaaatcattg ataaaggcaa | 780 |
| tacgagataa tattactacc actcgaaacg aagttaccaa agatgatgtt tatgcattga | 840 |
| agaaggccct cacttgtcta acgacacacc taatatatca ttcaaaagta gatggtatat | 900 |
| cattcgacat gctgggaaca caaaaaaata atctagccc actaggcaag atcggaacgt | 960 |
| ctatggacga tattatagcc atgttttcga atcccaatat gtatcttgtg aaggtggcgt | 1020 |
| acttgcaagc cattgaacac attttttctca tatcaaccaa atacaatgat atatttgatt | 1080 |
| acaccattga ttttagtaag cgtgaagcta ctgattctgg atcatttacc gatatattgc | 1140 |
| tcggaaacaa ggtgaaggaa tctttgtcat ttattgaggg tttgatttct gacataaaat | 1200 |
| ctcactcatt gaaagctggg gttacaggag gtatatcaag ttcatcatta tttgatgaaa | 1260 |
| tcttcgacga gttaaatttg gatcaagcaa caattgaaac ccttgttgca ccattagatt | 1320 |
| ggccacttat ctcagacaaa agcctccacc cttcactgaa gatggttgtg gtcctgccag | 1380 |
| gatttttcat agttccttaa taacatgaca tttcatagtc ccttcagtcc tgatgacaag | 1440 |
| acggtgaa | 1448 |

<210> SEQ ID NO 16
<211> LENGTH: 1350
<212> TYPE: DNA
<213> ORGANISM: Babesia microti

<400> SEQUENCE: 16

| | |
|---|---|
| gcctaagccc aaatgggatt taagcaggag gggataaaac agatgacctc caccatgccc | 60 |
| tactaactct aagctaagga aatccagcct gctggctatt tacctgcttt cctcgaagtg | 120 |
| aaaggccaga gtcaccccca atctttccca aaagattgaa gtcactctct ccatgccggc | 180 |
| aaaggtagat ggtgcgaggc tggacatgga tattcataag gtagtagaca attttactct | 240 |
| ggatgtagtc ctggactctg ttgaccagaa atctctggcc tacattaatc accttgatga | 300 |
| agacagatcc ctaggacaga gtagaaagag caattttatg gtcagaaaat ctgaaactag | 360 |
| gagtgtggca agcaaggggg caaggctatc agcacctagt gacaatccca gcacttagaa | 420 |
| ggcttagctg gaagggcttt aggtttgacc ctgactcaag acaaatgaac atatgaaaag | 480 |
| tatggggaga atgatctgtg tattgactgg tagggcctca tcagctattc cttctctccc | 540 |
| tgtcactgcc atccgtgcc gaattcggca cgagctcgtg ccgaaaccct aaaccctaaa | 600 |
| cccctaaacc ctaaacccta aaccctaaac cctaaaccct aaaccctaaa ccctaaaccc | 660 |
| taaaccccta aaccctaaa ccctaaaccc taaaccctaa accctaaacc ctaaaccct a | 720 |
| aaccctaacc ctaaccccta a ccctaaccct aacctagcct tcattgacgt ctatccccaa | 780 |
| tcttagaaga atcttcaaat cgattctaga ataactggaa acaattatca gaaattgtat | 840 |
| aactgcttat tagcttatta gcttattagt taggatgtat gcacattgat gacaactaga | 900 |
| tgcagcacca caatcactac cacgtaccaa tcatatacca ataatgtact aataatgtac | 960 |
| caataactat ggtttataaa gatggtgtca tttaaatcaa tattagttcc ttatattaca | 1020 |
| ctcttttttaa tgagcggtgc tgtctttgca agtgataccg atcccgaagc tggtgggcct | 1080 |

```
agtgaagctg gtgggcctag tggaactgtt gggcccagtg aagctggtgg gcctagtgaa    1140
gctggtgggc ctagtggaac tggttggcct agtgaagctg gtgggcctag tgaagctggt    1200
gggcctagtg aagctggtgg gcctagtgaa gctggtgggc ctagtggaac tggttggcct    1260
agtggaactg gttggcctag tgaagctggt tggtctagtg aacgatttgg atatcagctt    1320
cttccgtatt ctagaagaat agttatattt                                      1350

<210> SEQ ID NO 17
<211> LENGTH: 1820
<212> TYPE: DNA
<213> ORGANISM: Babesia microti

<400> SEQUENCE: 17
ggaaagcctt aaacatgcat gggaataatg aaatagtaaa aattgcagcc atggcaatgt     60
aataatgagt ggatgtttca gtcttgaggc tctttaacaa gagtgttgtc ttgtagtcaa    120
agacaaagtg attcgtcatg ccgcattcgc agccaccatc atcatcaggc gacgacgggt    180
ctctttcatt atcctcgggc ttattattgc aaccatgaca cccttcttta caaagtcttt    240 ttttttttcag cggtgtctga gtattatgcg attttattcc agccttccca cttttattct    300
tattgagatt gccatgctct tcttcatgag cgtcacttgt ttcctgcggt gtctgagtat    360
catacgattt tattccagca tttccacttt tattcttatt gattttgtca tgcccttctt    420
cacactcttc acatatttct tgcgttgtct gagtatcatg cgattttctt tcagccttct    480 cactttatt cgtattgatt ttgtcatgcc cttcttcatg agcgtcactt gtttcctgcg    540
gtgtctgagt atcatacgat tttattccag catttccact tttattctta ttgattttgt    600 catgccttc ttcacactct tcacatattt cttgcgttgt ctgagtatca tacgattta    660 ttccagcatt tccactttta ttcttattga ttttgtcatg cccttcttca cactcttcac    720
atatttcttg cgttgtctga gtatcatgcg attttctttc agccttctca cttttattcg    780
tattgggttt gccatgccct tctttacgct cttcatatat ttcttgtgcc gttagtctca    840
gtaagttgtc aagctcttca tatatttctt gcggtgtctg agtatcatgc gattttcttt    900
cagtcttctc acttttattc gtattgagtt tgccattccc ttcttcatga tcgtcacttg    960
tttcttgcgc cgttagtctc attaagttgt caagctcttc atcatctatt gaatggtatg   1020
gagctgtatc ttcccagggt ggttgaatta tgtcattctc gccgatttta aatgatggtt   1080
cttcatcatt tatatcagat gccatgtctg agtggtgccc taatctagag aattggtgtg   1140
gtaccccctc atccaaactt tcgggcaaca ccctggtatc agaatccatt tgttcgagcg   1200
gctcactatc gcaagcgtct tgtggattga tgttatcatg ttcctggatt tcaacatgta   1260
cagattctga atccgcattg ggttctggaa tatagttggt aactacattt gtttctagag   1320
aagtatcatt cttatattaa ttcatctaag atctgtgctt ctttgtttct acacatacag   1380
ggtgtctctt ttcccaacat aatatctgta aattcttccc agaagcagaa ccttgttggt   1440
accagacagc atcgggtctc tgtgagtttc tattcaggca acaggtgtat tctgtttgcc   1500
agtccaagtg catcctgtat tctagtactg gcttactacc ccaagcaaat cactggcatc   1560
aacatctagc actgagtgaa gcatgatctc ttctacaagg tgtttttcca ttgtgttgta   1620
agcccgtata caaggctgtt cccactcaac aatgaagaga cctcttagca tgaatggcca   1680
gatgtctgtt ctttaaatta aatcaatatg ttttgctcaa tatgtcagac ttgtttgtgg   1740
tggagccaaa attggaggtc ccatcgagat ttggagaaac ttgaaatgaa tgcaaaagat   1800
```

-continued ggtgggggct actcgtgccg 1820

<210> SEQ ID NO 18
<211> LENGTH: 263
<212> TYPE: PRT
<213> ORGANISM: Babesia microti

<400> SEQUENCE: 18

```
Leu Phe Leu Met Ser Gly Ala Val Phe Ala Ser Asp Thr Asp Pro Glu
 1               5                  10                  15

Ala Gly Gly Pro Ser Glu Ala Gly Gly Pro Ser Gly Thr Val Gly Pro
            20                  25                  30

Ser Glu Ala Gly Gly Pro Ser Glu Ala Gly Gly Pro Ser Gly Thr Gly
        35                  40                  45

Trp Pro Ser Glu Ala Gly Gly Pro Ser Glu Ala Gly Gly Pro Ser Glu
    50                  55                  60

Ala Gly Gly Pro Ser Glu Ala Gly Gly Pro Ser Gly Thr Gly Trp Pro
65                  70                  75                  80

Ser Gly Thr Gly Trp Pro Ser Glu Ala Gly Trp Ser Ser Glu Arg Phe
                85                  90                  95

Gly Tyr Gln Leu Leu Pro Tyr Ser Arg Arg Ile Val Ile Phe Asn Glu
            100                 105                 110
Val Cys Leu Ser Tyr Ile Tyr Lys His Ser Val Met Ile Leu Glu Arg
        115                 120                 125
Asp Arg Val Asn Asp Gly His Lys Asp Tyr Ile Glu Glu Lys Thr Lys
    130                 135                 140
Glu Lys Asn Lys Leu Lys Lys Glu Leu Glu Lys Cys Phe Pro Glu Gln
145                 150                 155                 160
Tyr Ser Leu Met Lys Lys Glu Glu Leu Ala Arg Ile Phe Asp Asn Ala
                165                 170                 175
Ser Thr Ile Ser Ser Lys Tyr Lys Leu Leu Val Asp Glu Ile Ser Asn
            180                 185                 190
Lys Ala Tyr Gly Thr Leu Glu Gly Pro Ala Ala Asp Asn Phe Asp His
        195                 200                 205
Phe Arg Asn Ile Trp Lys Ser Ile Val Leu Lys Asp Met Phe Ile Tyr
    210                 215                 220
Cys Asp Leu Leu Leu Gln His Leu Ile Tyr Lys Phe Tyr Tyr Asp Asn
225                 230                 235                 240
Thr Val Asn Asp Ile Lys Lys Asn Phe Asp Glu Ser Lys Ser Lys Ala
                245                 250                 255
Leu Val Leu Arg Asp Lys Ile
            260
```

<210> SEQ ID NO 19
<211> LENGTH: 310
<212> TYPE: PRT
<213> ORGANISM: Babesia microti

<400> SEQUENCE: 19

```
Met Ser Gly Ala Val Phe Ala Ser Asp Thr Asp Pro Glu Ala Gly Gly
 1               5                  10                  15

Pro Ser Glu Ala Gly Gly Pro Ser Gly Thr Val Gly Pro Ser Glu Ala
            20                  25                  30

Gly Gly Pro Ser Glu Ala Gly Gly Pro Ser Gly Thr Val Gly Pro Ser
        35                  40                  45

Glu Ala Gly Gly Pro Ser Glu Ala Gly Gly Pro Ser Gly Thr Gly Trp
```

```
                50                  55                  60
Pro Ser Glu Ala Gly Gly Pro Ser Glu Ala Gly Gly Pro Ser Gly Thr
 65                  70                  75                  80

Val Gly Pro Ser Glu Ala Gly Gly Pro Ser Glu Ala Gly Gly Pro Ser
                 85                  90                  95

Gly Thr Gly Trp Pro Ser Glu Ala Gly Gly Pro Ser Glu Ala Gly Gly
                100                 105                 110

Pro Ser Glu Ala Gly Gly Pro Ser Glu Ala Gly Gly Pro Ser Gly Thr
                115                 120                 125

Gly Trp Pro Ser Gly Thr Gly Trp Pro Ser Glu Ala Gly Trp Ser Ser
130                 135                 140

Glu Arg Phe Gly Tyr Gln Leu Leu Pro Tyr Ser Arg Arg Ile Val Ile
145                 150                 155                 160

Phe Asn Glu Val Cys Leu Ser Tyr Ile Tyr Lys His Ser Val Met Ile
                165                 170                 175

Leu Glu Arg Asp Arg Val Asn Asp Gly His Lys Asp Tyr Ile Glu Glu
                180                 185                 190

Lys Thr Lys Glu Lys Asn Lys Leu Lys Lys Glu Leu Glu Lys Cys Phe
                195                 200                 205

Pro Glu Gln Tyr Ser Leu Met Lys Lys Glu Leu Ala Arg Ile Phe
210                 215                 220

Asp Asn Ala Ser Thr Ile Ser Ser Lys Tyr Lys Leu Leu Val Asp Glu
225                 230                 235                 240

Ile Ser Asn Lys Ala Tyr Gly Thr Leu Glu Gly Pro Ala Ala Asp Asn
                245                 250                 255

Phe Asp His Phe Arg Asn Ile Trp Lys Ser Ile Val Leu Lys Asp Met
                260                 265                 270

Phe Ile Tyr Cys Asp Leu Leu Leu Gln His Leu Ile Tyr Lys Phe Tyr
                275                 280                 285

Tyr Asp Asn Thr Val Asn Asp Ile Lys Lys Asn Phe Asp Glu Ser Trp
                290                 295                 300

Thr Gln Thr Leu Lys Glu
305                 310

<210> SEQ ID NO 20
<211> LENGTH: 367
<212> TYPE: PRT
<213> ORGANISM: Babesia microti

<400> SEQUENCE: 20

Leu Trp Phe Ile Lys Met Val Ser Phe Lys Ser Ile Leu Val Pro Tyr
 1                   5                  10                  15

Ile Thr Leu Phe Leu Met Ser Gly Ala Val Phe Ala Ser Asp Thr Asp
                 20                  25                  30

Pro Glu Ala Gly Gly Pro Ser Glu Ala Gly Gly Pro Ser Gly Thr Val
                 35                  40                  45

Gly Pro Ser Glu Ala Gly Gly Pro Ser Glu Ala Gly Gly Pro Ser Gly
 50                  55                  60

Thr Gly Trp Pro Ser Glu Ala Gly Gly Pro Ser Glu Ala Gly Gly Pro
 65                  70                  75                  80

Ser Glu Ala Gly Gly Pro Ser Glu Ala Gly Gly Pro Ser Gly Thr Gly
                 85                  90                  95

Trp Pro Ser Gly Thr Gly Trp Pro Ser Glu Ala Gly Trp Ser Ser Glu
                100                 105                 110
```

-continued

```
Arg Phe Gly Tyr Gln Leu Leu Pro Tyr Ser Arg Arg Ile Val Ile Phe
            115                 120                 125

Asn Glu Val Cys Leu Ser Tyr Ile Tyr Lys His Ser Val Met Ile Leu
        130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Leu Ala Arg Ile Phe Asp
            180                 185                 190

Asn Ala Ser Thr Ile Ser Ser Lys Tyr Lys Leu Leu Val Asp Glu Ile
        195                 200                 205

Ser Asn Lys Ala Tyr Gly Thr Leu Glu Gly Pro Ala Ala Asp Asn Phe
    210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
            260                 265                 270

Lys Ala Leu Val Leu Arg Asp Lys Ile Thr Lys Asp Gly Asp Tyr
        275                 280                 285

Asn Thr His Phe Glu Asp Met Ile Lys Glu Leu Asn Ser Ala Ala Glu
    290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335

Thr Glu Ile Thr Lys Ile Thr Lys Val Ser Asn Val Ile Ile Pro Gly
            340                 345                 350

Ile Lys Ala Leu Thr Leu Thr Val Phe Leu Ile Phe Ile Thr Lys
        355                 360                 365
```

<210> SEQ ID NO 21
<211> LENGTH: 492
<212> TYPE: PRT
<213> ORGANISM: Babesia microti

<400> SEQUENCE: 21

```
Met Tyr Lys Ile Lys Ile Ser Asp Tyr Ile Ile Glu Phe Asp Asp Asn
1               5                  10                  15

Ala Lys Leu Pro Thr Asp Asn Val Ile Gly Ile Ser Ile Tyr Thr Cys
            20                  25                  30

Glu His Asn Asn Pro Val Leu Ile Glu Phe Tyr Val Ser Lys Lys Gly
        35                  40                  45

Ser Ile Cys Tyr Tyr Phe Tyr Ser Met Asn Asn Asp Thr Asn Lys Trp
    50                  55                  60

Asn Asn His Lys Ile Lys Tyr Asp Lys Arg Phe Asn Glu His Thr Asp
65                  70                  75                  80

Met Asn Gly Ile His Tyr Tyr Ile Asp Gly Ser Leu Leu Ala Ser
                85                  90                  95

Gly Glu Val Thr Ser Asn Phe Arg Tyr Ile Ser Lys Glu Tyr Glu Tyr
            100                 105                 110

Glu His Thr Glu Leu Ala Lys Glu His Cys Lys Lys Glu Lys Cys Val
        115                 120                 125
```

Asn Val Asp Asn Ile Glu Asp Asn Asn Leu Lys Ile Tyr Ala Lys Gln
    130                 135                 140

Phe Lys Ser Val Val Thr Thr Pro Ala Asp Val Ala Gly Val Ser Asp
145                 150                 155                 160

Gly Phe Phe Ile Arg Gly Gln Asn Leu Gly Ala Val Gly Ser Val Asn
                165                 170                 175

Glu Gln Pro Asn Thr Val Gly Met Ser Leu Glu Gln Phe Ile Lys Asn
            180                 185                 190

Glu Leu Tyr Ser Phe Ser Asn Glu Ile Tyr His Thr Ile Ser Ser Gln
        195                 200                 205

Ile Ser Asn Ser Phe Leu Ile Met Met Ser Asp Ala Ile Val Lys His
    210                 215                 220

Asp Asn Tyr Ile Leu Lys Lys Glu Gly Glu Gly Cys Glu Gln Ile Tyr
225                 230                 235                 240

Asn Tyr Glu Glu Phe Ile Glu Lys Leu Arg Gly Ala Arg Ser Glu Gly
                245                 250                 255

Asn Asn Met Phe Gln Glu Ala Leu Ile Arg Phe Arg Asn Ala Ser Ser
            260                 265                 270

Glu Glu Met Val Asn Ala Ala Ser Tyr Leu Ser Ala Ala Leu Phe Arg
        275                 280                 285

Tyr Lys Glu Phe Asp Asp Glu Leu Phe Lys Lys Ala Asn Asp Asn Phe
    290                 295                 300

Gly Arg Asp Asp Gly Tyr Asp Phe Asp Tyr Ile Asn Thr Lys Lys Glu
305                 310                 315                 320

Leu Val Ile Leu Ala Ser Val Leu Asp Gly Leu Asp Leu Ile Met Glu
                325                 330                 335

Arg Leu Ile Glu Asn Phe Ser Asp Val Asn Asn Thr Asp Asp Ile Lys
            340                 345                 350

Lys Ala Phe Asp Glu Cys Lys Ser Asn Ala Ile Ile Leu Lys Lys Lys
        355                 360                 365

Ile Leu Asp Asn Asp Glu Asp Tyr Lys Ile Asn Phe Arg Glu Met Val
    370                 375                 380

Asn Glu Val Thr Cys Ala Asn Thr Lys Phe Glu Ala Leu Asn Asp Leu
385                 390                 395                 400

Ile Ile Ser Asp Cys Glu Lys Lys Gly Ile Lys Ile Asn Arg Asp Val
                405                 410                 415

Ile Ser Ser Tyr Lys Leu Leu Leu Ser Thr Ile Thr Tyr Ile Val Gly
            420                 425                 430

Ala Gly Val Glu Ala Val Thr Val Ser Val Ser Ala Thr Ser Asn Gly
        435                 440                 445

Thr Glu Ser Gly Gly Ala Gly Ser Gly Thr Gly Thr Ser Val Ser Ala
    450                 455                 460

Thr Ser Thr Leu Thr Gly Asn Gly Gly Thr Glu Ser Gly Gly Thr Ala
465                 470                 475                 480

Gly Thr Thr Thr Ser Ser Gly Thr Trp Phe Gly Lys
                485                 490

<210> SEQ ID NO 22
<211> LENGTH: 138
<212> TYPE: PRT
<213> ORGANISM: Babesia microti

<400> SEQUENCE: 22

Ser Leu Gly Gln Pro Ala Ser Leu Gly Gln Pro Ala Ser Leu Gly Gln

```
           1               5                   10                  15
         Pro Ala Ser Leu Gly Gln Pro Ala Ser Leu Gly Gln Pro Ala Ser Leu
                         20                  25                  30

Gly Gln Pro Val Pro Leu Gly Pro Pro Ala Ser Leu Gly Pro Pro Ala
                         35                  40                  45

Ser Leu Gly Pro Pro Ala Ser Leu Gly Gln Pro Val Pro Leu Gly Pro
                 50                  55                  60

Pro Ala Ser Leu Gly Pro Pro Ala Ser Leu Gly Pro Pro Ala Ser Leu
         65                  70                  75                  80

Gly Pro Pro Ala Ser Leu Gly Pro Pro Ala Ser Leu Gly Pro Pro Ala
                         85                  90                  95

Ser Leu Gly Pro Pro Ala Ser Leu Gly Pro Pro Ala Ser Leu Gly Pro
                         100                 105                 110

Thr Val Pro Leu Gly Pro Pro Ala Ser Arg Ser Val Ser Pro Ala Lys
                         115                 120                 125

Thr Ala Pro Leu Ile Lys Lys Ser Val Ile
                         130                 135

<210> SEQ ID NO 23
         <211> LENGTH: 303
         <212> TYPE: PRT
         <213> ORGANISM: Babesia microti

<400> SEQUENCE: 23

Leu Trp Phe Ile Lys Met Val Ser Phe Lys Ser Ile Leu Val Pro Tyr
         1               5                   10                  15

Ile Thr Leu Phe Leu Met Ser Gly Ala Val Phe Ala Gly Asp Thr Asp
                         20                  25                  30

Arg Glu Ala Gly Gly Pro Ser Gly Thr Val Gly Pro Ser Glu Ala Gly
                         35                  40                  45

Gly Pro Ser Glu Ala Gly Gly Pro Ser Glu Ala Gly Gly Pro Ser Glu
                 50                  55                  60

Ala Gly Gly Pro Ser Glu Ala Gly Gly Pro Ser Glu Ala Gly Gly Pro
         65                  70                  75                  80

Ser Glu Ala Gly Gly Pro Ser Glu Ala Gly Gly Pro Ser Gly Thr Gly
                         85                  90                  95

Trp Pro Ser Glu Ala Gly Trp Pro Ser Glu Ala Gly Trp Pro Ser Glu
                         100                 105                 110

Ala Gly Trp Pro Ser Glu Ala Gly Trp Pro Ser Glu Ala Gly Trp Pro
                         115                 120                 125

Ser Glu Arg Phe Gly Tyr Gln Leu Leu Trp Tyr Ser Arg Arg Ile Val
                 130                 135                 140

Ile Phe Asn Glu Ile Tyr Leu Ser His Ile Tyr Glu His Ser Val Met
         145                 150                 155                 160

Ile Leu Glu Arg Asp Arg Val Asn Asp Gly His Lys Asp Tyr Ile Glu
                         165                 170                 175

Glu Lys Thr Lys Glu Lys Asn Lys Leu Lys Lys Glu Leu Glu Lys Cys
                         180                 185                 190

Phe Pro Glu Gln Tyr Ser Leu Met Lys Lys Glu Glu Leu Ala Arg Ile
                         195                 200                 205

Ile Asp Asn Ala Ser Thr Ile Ser Ser Lys Tyr Lys Leu Leu Val Asp
                 210                 215                 220

Glu Ile Ser Asn Lys Ala Tyr Gly Thr Leu Glu Gly Pro Ala Ala Asp
         225                 230                 235                 240
```

```
Asp Phe Asp His Phe Arg Asn Ile Trp Lys Ser Ile Val Pro Lys Asn
                245                 250                 255

Met Phe Leu Tyr Cys Asp Leu Leu Lys His Leu Ile Arg Lys Phe
            260                 265                 270

Tyr Cys Asp Asn Thr Ile Asn Asp Ile Lys Lys Asn Phe Asp Asp Ile
        275                 280                 285

Glu Lys Leu Gly Cys Phe Gln Ala Arg Ser Phe Leu Pro Val Asn
    290                 295                 300
```

<210> SEQ ID NO 24
<211> LENGTH: 592
<212> TYPE: PRT
<213> ORGANISM: Babesia microti

<400> SEQUENCE: 24

```
Met Met Lys Phe Asn Ile Asp Lys Ile Ile Leu Ile Asn Leu Ile Val
 1               5                  10                  15

Leu Leu Asn Arg Asn Val Val Tyr Cys Val Asp Thr Asn Asn Ser Ser
                20                  25                  30

Leu Ile Glu Ser Gln Pro Val Thr Thr Asn Ile Asp Thr Asp Asn Thr
            35                  40                  45

Ile Thr Thr Asn Lys Tyr Thr Gly Thr Ile Ile Asn Ala Asn Ile Val
        50                  55                  60

Glu Tyr Arg Glu Phe Glu Asp Glu Pro Leu Thr Ile Gly Phe Arg Tyr
65                  70                  75                  80

Thr Ile Asp Lys Ser Gln Gln Asn Lys Leu Ser His Pro Asn Lys Ile
                85                  90                  95

Asp Lys Ile Lys Phe Ser Asp Tyr Ile Ile Glu Phe Asp Asp Asn Ala
            100                 105                 110

Lys Leu Pro Thr Asp Asn Val Ile Cys Ile Ser Ile Tyr Thr Cys Lys
        115                 120                 125

His Asn Asn Pro Val Leu Ile Arg Phe Ser Cys Ser Ile Glu Lys Tyr
    130                 135                 140

Tyr Tyr His Tyr Phe Tyr Ser Met Asn Asn Asp Thr Asn Lys Trp Asn
145                 150                 155                 160

Asn His Lys Leu Lys Tyr Asp Lys Thr Tyr Asn Glu Tyr Thr Asp Asn
                165                 170                 175

Asn Gly Val Asn Tyr Tyr Lys Ile Tyr Tyr Ser Asp Lys Gln Asn Ser
            180                 185                 190

Pro Thr Asn Gly Asn Glu Tyr Glu Asp Val Ala Leu Ala Arg Ile His
        195                 200                 205

Cys Asn Glu Glu Arg Cys Ala Asn Val Lys Val Asp Lys Ile Lys Tyr
    210                 215                 220

Lys Asn Leu Glu Ile Tyr Val Lys Gln Leu Gly Thr Ile Ile Asn Ala
225                 230                 235                 240

Asn Ile Val Glu Tyr Leu Val Phe Glu Asp Glu Pro Leu Thr Ile Gly
                245                 250                 255

Phe Arg Tyr Thr Ile Asp Lys Ser Gln Gln Asn Glu Leu Ser His Pro
            260                 265                 270

Asn Lys Ile Tyr Lys Ile Lys Phe Ser Asp Tyr Ile Ile Glu Phe Asp
        275                 280                 285

Asp Asp Ala Lys Leu Thr Thr Ile Gly Thr Val Glu Asp Ile Thr Ile
    290                 295                 300

Tyr Thr Cys Lys His Asn Asn Pro Val Leu Ile Arg Phe Ser Cys Ser
305                 310                 315                 320
```

-continued

```
Ile Glu Lys Tyr Tyr Tyr Tyr Phe Tyr Ser Met Asn Asn Asn Thr
                325                 330                 335

Asn Lys Trp Asn Asn His Asn Leu Lys Tyr Asp Asn Arg Phe Lys Glu
            340                 345                 350

His Ser Asp Lys Asn Gly Ile Asn Tyr Glu Ile Ser Ala Phe Lys
        355                 360                 365

Trp Ser Phe Ser Cys Phe Phe Val Asn Lys Tyr Glu His Lys Glu Leu
    370                 375                 380

Ala Arg Ile His Cys Asn Glu Glu Arg Cys Ala Asn Val Lys Val Asp
385                 390                 395                 400

Lys Ile Lys Tyr Lys Asn Leu Glu Ile Tyr Val Lys Gln Leu Gly Thr
                405                 410                 415

Ile Ile Asn Ala Asn Ile Val Glu Tyr Leu Val Phe Glu Asp Glu Pro
            420                 425                 430

Leu Thr Ile Gly Phe Arg Tyr Thr Ile Asp Lys Ser Gln Gln Asn Glu
        435                 440                 445

Leu Ser His Pro Asn Lys Ile Tyr Lys Ile Lys Phe Ser Asp Tyr Ile
    450                 455                 460

Ile Glu Phe Asp Asp Ala Lys Leu Thr Thr Ile Gly Thr Val Glu
465                 470                 475                 480

Asp Ile Thr Ile Tyr Thr Cys Lys His Asn Asn Pro Val Leu Ile Arg
                485                 490                 495

Phe Ser Cys Ser Ile Glu Lys Tyr Tyr Tyr Tyr Phe Tyr Ser Met
            500                 505                 510

Asn Asn Asn Thr Asn Lys Trp Asn Asn His Asn Leu Lys Tyr Asp Asn
        515                 520                 525

Arg Phe Lys Glu His Ser Asp Lys Asn Gly Ile Asn Tyr Tyr Glu Ile
    530                 535                 540

Ser Ala Phe Lys Trp Ser Phe Ser Cys Phe Phe Val Asn Lys Tyr Glu
545                 550                 555                 560

His Lys Glu Leu Ala Arg Ile His Cys Asn Glu Glu Lys Cys Val Asn
                565                 570                 575

Val Lys Val Asp Asn Ile Gly Asn Lys Asn Leu Glu Ile Tyr Val Lys
            580                 585                 590
```

<210> SEQ ID NO 25
<211> LENGTH: 463
<212> TYPE: PRT
<213> ORGANISM: Babesia microti

<400> SEQUENCE: 25

```
Ile Ile Met Lys Ile Asn Ile Asp Asn Ile Leu Ile Asn Leu Ile
1               5                   10                  15

Ile Leu Leu Asn Arg Asn Val Val Tyr Cys Val Asp Lys Asn Asp Val
            20                  25                  30

Ser Leu Trp Lys Ser Lys Pro Ile Thr Thr Val Ser Thr Thr Asn Asp
        35                  40                  45

Thr Ile Thr Asn Lys Tyr Thr Ser Thr Val Ile Asn Ala Asn Phe Ala
    50                  55                  60

Ser Tyr Arg Glu Phe Glu Asp Arg Glu Pro Leu Thr Ile Gly Phe Glu
65                  70                  75                  80

Tyr Met Ile Asp Lys Ser Gln Gln Asp Lys Leu Ser His Pro Asn Lys
                85                  90                  95

Ile Asp Lys Ile Lys Ile Ser Asp Tyr Ile Ile Glu Phe Asp Asp Asn
```

-continued

```
                100                 105                 110
Ala Lys Leu Pro Thr Gly Ser Val Asn Asp Ile Ser Ile Thr Cys
            115                 120                 125

Lys His Asn Asn Pro Val Leu Ile Arg Phe Ser Cys Leu Ile Glu Gly
130                 135                 140

Ser Ile Cys Tyr Tyr Phe Tyr Leu Leu Asn Asn Asp Thr Asn Lys Trp
145                 150                 155                 160

Asn Asn His Lys Leu Lys Tyr Asp Lys Thr Tyr Asn Glu His Thr Asp
            165                 170                 175

Asn Asn Gly Ile Asn Tyr Tyr Lys Ile Asp Tyr Ser Glu Ser Thr Glu
            180                 185                 190

Pro Thr Thr Glu Ser Thr Thr Cys Phe Cys Phe Arg Lys Lys Asn His
            195                 200                 205

Lys Ser Glu Arg Lys Glu Leu Glu Asn Tyr Lys Tyr Glu Gly Thr Glu
210                 215                 220

Leu Ala Arg Ile His Cys Asn Lys Gly Lys Cys Val Lys Leu Gly Asp
225                 230                 235                 240

Ile Lys Ile Lys Asp Lys Asn Leu Glu Ile Tyr Val Lys Gln Leu Met
            245                 250                 255

Ser Val Asn Thr Pro Val Asn Phe Asp Asn Pro Thr Ser Ile Asn Leu
            260                 265                 270

Pro Thr Val Ser Thr Thr Asn Asp Thr Ile Thr Asn Lys Tyr Thr Gly
            275                 280                 285

Thr Ile Ile Asn Ala Asn Ile Val Glu Tyr Cys Glu Phe Glu Asp Glu
            290                 295                 300

Pro Leu Thr Ile Gly Phe Arg Tyr Thr Ile Asp Lys Ser Gln Gln Asn
305                 310                 315                 320

Lys Leu Ser His Pro Asn Lys Ile Asp Lys Ile Lys Phe Phe Asp Tyr
            325                 330                 335

Ile Ile Glu Phe Asp Asp Val Lys Leu Pro Thr Ile Gly Thr Val
            340                 345                 350

Asn Ile Ile Tyr Ile Tyr Thr Cys Glu His Asn Asn Pro Val Leu Val
            355                 360                 365

Glu Phe Ile Val Ser Ile Glu Glu Ser Tyr Tyr Phe Tyr Phe Tyr Ser
370                 375                 380

Met Asn Asn Asn Thr Asn Lys Trp Asn Asn His Lys Leu Lys Tyr Asp
385                 390                 395                 400

Lys Arg Phe Lys Lys Tyr Thr Lys Asn Gly Ile Asn Cys Tyr Glu Tyr
            405                 410                 415

Val Leu Arg Lys Cys Ser Ser Tyr Thr Arg Lys Asn Glu Tyr Glu His
            420                 425                 430

Lys Glu Leu Ala Arg Ile His Cys Asn Glu Glu Lys Cys Val Asn Val
            435                 440                 445

Lys Val Asp Asn Ile Glu Lys Lys Asn Leu Glu Ile Tyr Val Lys
            450                 455                 460

<210> SEQ ID NO 26
<211> LENGTH: 297
<212> TYPE: PRT
<213> ORGANISM: Babesia microti

<400> SEQUENCE: 26

Arg Ala Ala Arg Ala Asp Tyr Tyr Lys Tyr Leu Val Asp Glu Tyr Ser
1               5                   10                  15
```

```
Ser Pro Arg Glu Glu Arg Glu Leu Ala Arg Val His Cys Asn Glu Glu
            20                  25                  30

Lys Cys Val Lys Leu Asp Gly Ile Lys Phe Lys Asp Lys Asn Leu Glu
            35                  40                  45

Ile Tyr Val Lys Gln Leu Met Ser Val Asn Thr Pro Val Phe Asp
 50                  55                  60

Asn Asn Thr Leu Ile Asn Pro Thr Ser Ser Gly Ala Thr Asp Asp
 65                  70                  75                  80

Ile Thr Tyr Glu Leu Ser Val Glu Ser Gln Pro Val Pro Thr Asn Ile
                     85                  90                  95

Asp Thr Gly Asn Asn Ile Thr Thr Asn Thr Ser Asn Asn Asn Leu Ile
                100                 105                 110

Lys Ala Lys Phe Leu Tyr Asn Phe Asn Leu Pro Gly Lys Pro Ser Thr
                115                 120                 125

Gly Leu Phe Glu Tyr Thr Ile Asp Lys Ser Glu Gln Asn Lys Leu Ser
    130                 135                 140

His Pro Asn Lys Ile Asp Lys Ile Lys Phe Ser Asp Tyr Ile Ile Glu
145                 150                 155                 160

Phe Asp Asp Asp Ala Lys Leu Pro Thr Ile Gly Thr Val Asn Ile Ile
                165                 170                 175

Ser Ile Ile Thr Cys Lys His Asn Asn Pro Val Leu Val Glu Phe Ile
                180                 185                 190

Val Ser Thr Glu Ile Tyr Cys Tyr Tyr Asn Tyr Phe Tyr Ser Met Asn
            195                 200                 205

Asn Asn Thr Asn Lys Trp Asn Asn His Lys Leu Lys Tyr Asp Lys Arg
            210                 215                 220

Tyr Lys Glu Glu Tyr Thr Asp Asp Asn Gly Ile Asn Tyr Tyr Lys Leu
225                 230                 235                 240

Asn Asp Ser Glu Pro Thr Glu Ser Thr Glu Ser Thr Thr Cys Phe Cys
                245                 250                 255

Phe Arg Lys Lys Asn His Lys Tyr Glu Asn Glu Arg Thr Ala Leu Ala
            260                 265                 270

Lys Glu His Cys Asn Glu Glu Arg Cys Val Lys Val Asp Asn Ile Lys
            275                 280                 285

Asp Asn Asn Leu Glu Ile Tyr Leu Lys
            290                 295

<210> SEQ ID NO 27
<211> LENGTH: 121
<212> TYPE: PRT
<213> ORGANISM: Babesia microti

<400> SEQUENCE: 27

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Glu Ala Gly
            35                  40                  45

Gly Pro Ser Gly Thr Val Gly Pro Ser Glu Ala Gly Gly Pro Ser Glu
    50                  55                  60

Ala Gly Gly Pro Ser Gly Thr Gly Trp Pro Ser Glu Ala Gly Gly Pro
65                  70                  75                  80

Ser Glu Ala Gly Gly Pro Ser Gly Thr Gly Trp Pro Ser Glu Ala Gly
                85                  90                  95
```

-continued

```
Trp Ser Ser Glu Arg Phe Gly Tyr Gln Leu Leu Pro Tyr Ser Arg Arg
            100                 105                 110

Ile Val Thr Phe Asn Glu Val Cys Leu
        115                 120

<210> SEQ ID NO 28
<211> LENGTH: 267
<212> TYPE: PRT
<213> ORGANISM: Babesia microti

<400> SEQUENCE: 28

Leu Trp Phe Ile Lys Met Val Ser Phe Lys Ser Ile Leu Val Pro Tyr
  1               5                  10                  15

Ile Thr Leu Phe Leu Met Ser Gly Ala Val Phe Ala Ser Asp Thr Asp
             20                  25                  30

Pro Glu Ala Gly Gly Pro Ser Gly Thr Val Gly Pro Ser Glu Ala Gly
         35                  40                  45

Gly Pro Ser Glu Ala Gly Gly Pro Ser Gly Thr Gly Trp Pro Ser Glu
 50                  55                  60

Ala Gly Gly Pro Ser Glu Ala Gly Gly Pro Ser Gly Thr Gly Trp Pro
 65                  70                  75                  80

Ser Glu Ala Gly Trp Ser Ser Glu Arg Phe Gly Tyr Gln Leu Leu Pro
                 85                  90                  95

Tyr Ser Arg Arg Ile Val Thr Phe Asn Glu Val Cys Leu Ser Tyr Ile
            100                 105                 110

Tyr Lys His Ser Val Met Ile Leu Glu Arg Asp Arg Val Asn Asp Gly
            115                 120                 125

His Lys Asp Tyr Ile Glu Glu Lys Thr Lys Glu Lys Asn Lys Leu Lys
        130                 135                 140

Lys Glu Leu Glu Lys Cys Phe Pro Glu Gln Tyr Ser Leu Met Lys Lys
145                 150                 155                 160

Glu Glu Leu Ala Arg Ile Phe Asp Asn Ala Ser Thr Ile Ser Ser Lys
                165                 170                 175

Tyr Lys Leu Leu Val Asp Glu Ile Ser Asn Lys Ala Tyr Gly Thr Leu
            180                 185                 190

Glu Gly Pro Ala Ala Asp Asn Phe Asp His Phe Arg Asn Ile Trp Lys
        195                 200                 205

Ser Ile Val Leu Lys Asp Met Phe Ile Tyr Cys Asp Leu Leu Leu Gln
210                 215                 220

His Leu Ile Tyr Lys Phe Tyr Tyr Asp Asn Thr Ile Asn Asp Ile Lys
225                 230                 235                 240

Lys Asn Phe Asp Glu Ser Lys Ser Lys Ala Leu Val Leu Arg Asp Lys
                245                 250                 255

Ile Thr Lys Lys Asp Val Tyr Val Asn Asp His
            260                 265

<210> SEQ ID NO 29
<211> LENGTH: 16
<212> TYPE: PRT
<213> ORGANISM: Babesia microti

<400> SEQUENCE: 29

Ala Trp Thr Phe Ser Val Leu Glu Leu Gln Glu Phe Ser Tyr Thr Val
  1               5                  10                  15

<210> SEQ ID NO 30
```

```
<211> LENGTH: 465
<212> TYPE: PRT
<213> ORGANISM: Babesia microti

<400> SEQUENCE: 30
```

| | | | | | | | | | | | | | | |
|---|---|---|---|---|---|---|---|---|---|---|---|---|---|---|
| Met | Leu | Thr | Phe | Gly | Asn | Ile | Arg | Phe | His | Asn | Ile | Asn | Leu | Pro | Pro |
| 1 | | | | 5 | | | | | 10 | | | | | 15 | |
| Phe | Ser | Leu | Gly | Ile | Ile | His | Ser | Ile | Thr | Val | Glu | Lys | Ala | Ile | Asn |
| | | | 20 | | | | | 25 | | | | | 30 | | |
| Ser | Glu | Asp | Phe | Asp | Gly | Ile | Gln | Thr | Leu | Leu | Gln | Val | Ser | Ile | Ile |
| | | 35 | | | | | 40 | | | | | 45 | | | |
| Ala | Ser | Tyr | Gly | Pro | Ser | Gly | Asp | Tyr | Ser | Ser | Phe | Val | Phe | Thr | Pro |
| | 50 | | | | | 55 | | | | | 60 | | | | |
| Val | Val | Thr | Ala | Asp | Thr | Asn | Val | Phe | Tyr | Lys | Leu | Glu | Thr | Asp | Phe |
| 65 | | | | | 70 | | | | | 75 | | | | | 80 |
| Lys | Leu | Asp | Val | Asp | Val | Ile | Thr | Lys | Thr | Ser | Leu | Glu | Leu | Pro | Thr |
| | | | | 85 | | | | | 90 | | | | | 95 | |
| Ser | Val | Pro | Gly | Phe | His | Tyr | Thr | Glu | Thr | Ile | Tyr | Gln | Gly | Thr | Glu |
| | | | 100 | | | | | 105 | | | | | 110 | | |
| Leu | Ser | Lys | Phe | Ser | Lys | Pro | Gln | Cys | Lys | Leu | Asn | Asp | Pro | Pro | Ile |
| | | 115 | | | | | 120 | | | | | 125 | | | |
| Thr | Thr | Gly | Ser | Gly | Leu | Gln | Ile | Ile | His | Asp | Gly | Leu | Asn | Asn | Ser |
| | 130 | | | | | 135 | | | | | 140 | | | | |
| Thr | Ile | Ile | Thr | Asn | Lys | Glu | Val | Asn | Val | Asp | Gly | Thr | Asp | Leu | Val |
| 145 | | | | | 150 | | | | | 155 | | | | | 160 |
| Phe | Phe | Glu | Leu | Leu | Pro | Pro | Ser | Asp | Gly | Ile | Pro | Thr | Leu | Arg | Ser |
| | | | | 165 | | | | | 170 | | | | | 175 | |
| Lys | Leu | Phe | Pro | Val | Leu | Lys | Ser | Ile | Pro | Met | Ile | Ser | Thr | Gly | Val |
| | | | 180 | | | | | 185 | | | | | 190 | | |
| Asn | Glu | Leu | Leu | Leu | Glu | Val | Leu | Glu | Asn | Pro | Ser | Phe | Pro | Ser | Ala |
| | | 195 | | | | | 200 | | | | | 205 | | | |
| Ile | Ser | Asn | Tyr | Thr | Gly | Leu | Thr | Gly | Arg | Leu | Asn | Lys | Leu | Leu | Thr |
| | 210 | | | | | 215 | | | | | 220 | | | | |
| Val | Leu | Asp | Gly | Ile | Val | Asp | Ser | Ala | Ile | Ser | Val | Lys | Thr | Thr | Glu |
| 225 | | | | | 230 | | | | | 235 | | | | | 240 |
| Thr | Val | Pro | Asp | Asp | Ala | Glu | Thr | Ser | Ile | Ser | Ser | Leu | Lys | Ser | Leu |
| | | | | 245 | | | | | 250 | | | | | 255 | |
| Ile | Lys | Ala | Ile | Arg | Asp | Asn | Ile | Thr | Thr | Thr | Arg | Asn | Glu | Val | Thr |
| | | | 260 | | | | | 265 | | | | | 270 | | |
| Lys | Asp | Asp | Val | Tyr | Ala | Leu | Lys | Lys | Ala | Leu | Thr | Cys | Leu | Thr | Thr |
| | | 275 | | | | | 280 | | | | | 285 | | | |
| His | Leu | Ile | Tyr | His | Ser | Lys | Val | Asp | Gly | Ile | Ser | Phe | Asp | Met | Leu |
| | 290 | | | | | 295 | | | | | 300 | | | | |
| Gly | Thr | Gln | Lys | Asn | Lys | Ser | Ser | Pro | Leu | Gly | Lys | Ile | Gly | Thr | Ser |
| 305 | | | | | 310 | | | | | 315 | | | | | 320 |
| Met | Asp | Asp | Ile | Ile | Ala | Met | Phe | Ser | Asn | Pro | Asn | Met | Tyr | Leu | Val |
| | | | | 325 | | | | | 330 | | | | | 335 | |
| Lys | Val | Ala | Tyr | Leu | Gln | Ala | Ile | Glu | His | Ile | Phe | Leu | Ile | Ser | Thr |
| | | | 340 | | | | | 345 | | | | | 350 | | |
| Lys | Tyr | Asn | Asp | Ile | Phe | Asp | Tyr | Thr | Ile | Asp | Phe | Ser | Lys | Arg | Glu |
| | | 355 | | | | | 360 | | | | | 365 | | | |
| Ala | Thr | Asp | Ser | Gly | Ser | Phe | Thr | Asp | Ile | Leu | Leu | Gly | Asn | Lys | Val |
| | 370 | | | | | 375 | | | | | 380 | | | | |
| Lys | Glu | Ser | Leu | Ser | Phe | Ile | Glu | Gly | Leu | Ile | Ser | Asp | Ile | Lys | Ser |

-continued

```
385                 390                 395                 400

His Ser Leu Lys Ala Gly Val Thr Gly Gly Ile Ser Ser Ser Ser Leu
                405                 410                 415

Phe Asp Glu Ile Phe Asp Glu Leu Asn Leu Asp Gln Ala Thr Ile Arg
            420                 425                 430

Thr Leu Val Ala Pro Leu Asp Trp Pro Leu Ile Ser Asp Lys Ser Leu
        435                 440                 445

His Pro Ser Leu Lys Met Val Val Val Leu Pro Gly Phe Phe Ile Val
    450                 455                 460

Pro
465

<210> SEQ ID NO 31
<211> LENGTH: 128
<212> TYPE: PRT
<213> ORGANISM: Babesia microti

<400> SEQUENCE: 31

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Gly Thr Val
        35                  40                  45

Gly Pro Ser Glu Ala Gly Gly Pro Ser Glu Ala Gly Gly Pro Ser Gly
    50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Gly Thr Gly Trp Pro Ser Glu Ala Gly Trp Ser Ser Glu
            100                 105                 110

Arg Phe Gly Tyr Gln Leu Leu Pro Tyr Ser Arg Arg Ile Val Ile Phe
        115                 120                 125

<210> SEQ ID NO 32
<211> LENGTH: 245
<212> TYPE: PRT
<213> ORGANISM: Babesia microti

<400> SEQUENCE: 32

Gln Glu Cys Cys Leu Val Val Lys Asp Lys Val Ile Arg His Ala Ala
 1               5                  10                  15

Phe Ala Ala Thr Ile Ile Ile Arg Arg Arg Val Ser Phe Ile Ile
            20                  25                  30

Leu Gly Leu Ile Ile Ala Thr Met Thr Pro Phe Phe Thr Lys Val Phe
        35                  40                  45

Phe Phe Gln Arg Cys Leu Ser Ile Met Arg Phe Tyr Ser Ser Leu Pro
    50                  55                  60

Thr Phe Ile Leu Ile Glu Ile Ala Met Leu Phe Phe Met Ser Val Thr
65                  70                  75                  80

Cys Phe Leu Arg Cys Leu Ser Ile Ile Arg Phe Tyr Ser Ser Ile Ser
                85                  90                  95

Thr Phe Ile Leu Ile Asp Phe Val Met Pro Phe Phe Thr Leu Phe Thr
            100                 105                 110

Tyr Phe Leu Arg Cys Leu Ser Ile Met Arg Phe Ser Phe Ser Leu Leu
```

```
              115                 120                 125
Thr Phe Ile Arg Ile Asp Phe Val Met Pro Phe Phe Met Ser Val Thr
    130                 135                 140
Cys Phe Leu Arg Cys Leu Ser Ile Ile Arg Phe Tyr Ser Ser Ile Ser
145                 150                 155                 160
Thr Phe Ile Leu Ile Asp Phe Val Met Pro Phe Phe Thr Leu Phe Thr
                165                 170                 175
Tyr Phe Leu Arg Cys Leu Ser Ile Ile Arg Phe Tyr Ser Ser Ile Ser
                180                 185                 190
Thr Phe Ile Leu Ile Asp Phe Val Met Pro Phe Phe Thr Leu Phe Thr
            195                 200                 205
Tyr Phe Leu Arg Cys Leu Ser Ile Met Arg Phe Ser Phe Ser Leu Leu
        210                 215                 220
Thr Phe Ile Arg Ile Gly Phe Ala Met Pro Phe Phe Thr Leu Phe Ile
225                 230                 235                 240
Tyr Phe Leu Cys Arg
                245

<210> SEQ ID NO 33
<211> LENGTH: 293
<212> TYPE: PRT
<213> ORGANISM: Babesia microti

<400> SEQUENCE: 33

Thr Ala Phe Ala Ala Phe Leu Ala Phe Gly Asn Ile Ser Pro Val Leu
1               5                   10                  15
Ser Ala Gly Gly Ser Gly Gly Asn Gly Gly Asn Gly Gly His Gln
            20                  25                  30
Glu Gln Asn Asn Ala Asn Asp Ser Ser Asn Pro Thr Gly Ala Gly Gly
        35                  40                  45
Gln Pro Asn Asn Glu Ser Lys Lys Ala Val Lys Leu Asp Leu Asp
    50                  55                  60
Leu Met Lys Glu Thr Lys Asn Val Cys Thr Thr Val Asn Thr Lys Leu
65                  70                  75                  80
Val Gly Lys Ala Lys Ser Lys Leu Asn Lys Leu Glu Gly Glu Ser His
                85                  90                  95
Lys Glu Tyr Val Ala Glu Lys Thr Lys Glu Ile Asp Glu Lys Asn Lys
            100                 105                 110
Lys Phe Asn Glu Asn Leu Val Lys Ile Glu Lys Lys Lys Ile Lys
        115                 120                 125
Val Pro Ala Asp Thr Gly Ala Glu Val Asp Ala Val Asp Asp Gly Val
    130                 135                 140
Ala Gly Ala Leu Ser Asp Leu Ser Ser Asp Ile Ser Ala Ile Lys Thr
145                 150                 155                 160
Leu Thr Asp Asp Val Ser Glu Lys Val Ser Glu Asn Leu Lys Asp Asp
                165                 170                 175
Glu Ala Ser Ala Thr Glu His Thr Asp Ile Lys Glu Lys Ala Thr Leu
            180                 185                 190
Leu Gln Glu Ser Cys Asn Gly Ile Gly Thr Ile Leu Asp Lys Leu Ala
        195                 200                 205
Glu Tyr Leu Asn Asn Asp Thr Thr Gln Asn Ile Lys Lys Glu Phe Asp
    210                 215                 220
Glu Arg Lys Lys Asn Leu Thr Ser Leu Lys Thr Lys Val Glu Asn Lys
225                 230                 235                 240
```

-continued

```
Asp Glu Asp Tyr Val Asp Val Thr Met Thr Ser Lys Thr Asp Leu Ile
            245                 250                 255

Ile His Cys Leu Thr Cys Thr Asn Asp Ala His Gly Leu Phe Asp Phe
            260                 265                 270

Glu Ser Lys Ser Leu Ile Lys Gln Thr Phe Lys Leu Arg Ser Lys Asp
            275                 280                 285

Glu Gly Glu Leu Cys
            290

<210> SEQ ID NO 34
<211> LENGTH: 431
<212> TYPE: PRT
<213> ORGANISM: Babesia microti

<400> SEQUENCE: 34

Gly Pro Lys Met Lys Val Asn Ser Ala Asn Leu Asp Phe Arg Trp Ala
  1               5                  10                  15

Met Tyr Met Leu Asn Ser Lys Ile His Leu Ile Glu Ser Ser Leu Ile
             20                  25                  30

Asp Asn Phe Thr Leu Asp Asn Pro Ser Ala Tyr Glu Ile Leu Arg Val
         35                  40                  45

Ser Tyr Asn Ser Asn Glu Phe Gln Val Gln Ser Pro Gln Asn Ile Asn
     50                  55                  60

Asn Glu Met Glu Ser Ser Thr Pro Glu Ser Asn Ile Ile Trp Val Val
 65                  70                  75                  80

His Ser Asp Val Ile Met Lys Arg Phe Asn Cys Lys Asn Arg Lys Ser
                 85                  90                  95

Leu Ser Thr His Ser Leu Thr Glu Asn Asp Ile Leu Lys Phe Gly Arg
            100                 105                 110

Ile Glu Leu Ser Val Lys Cys Ile Ile Met Gly Ala Gly Ile Thr Ala
        115                 120                 125

Ser Asp Leu Asn Leu Lys Gly Leu Gly Phe Ile Ser Pro Asp Lys Gln
    130                 135                 140

Ser Thr Asn Val Cys Asn Tyr Phe Glu Asp Met His Glu Ser Tyr His
145                 150                 155                 160

Ile Leu Asp Thr Gln Arg Ala Ser Asp Cys Val Ser Asp Asp Gly Ala
                165                 170                 175

Asp Ile Asp Ile Ser Asn Phe Asp Met Val Gln Asp Gly Asn Ile Asn
            180                 185                 190

Ser Val Asp Ala Asp Ser Glu Thr Cys Met Ala Asn Ser Gly Val Thr
        195                 200                 205

Val Asn Asn Thr Glu Asn Val Ser Asn Ser Glu Asn Phe Gly Lys Leu
    210                 215                 220

Lys Ser Leu Val Ser Thr Thr Pro Leu Cys Arg Ile Cys Leu Cys
225                 230                 235                 240

Gly Glu Ser Asp Pro Gly Pro Leu Val Thr Pro Cys Asn Cys Lys Gly
                245                 250                 255

Ser Leu Asn Tyr Val His Leu Glu Cys Leu Arg Thr Trp Ile Lys Gly
            260                 265                 270

Arg Leu Ser Ile Val Lys Asp Asp Ala Ser Phe Phe Trp Lys Glu
        275                 280                 285

Leu Ser Cys Glu Leu Cys Gly Lys Pro Tyr Pro Ser Val Leu Gln Val
    290                 295                 300

Asp Asp Thr Glu Thr Asn Leu Met Asp Ile Lys Lys Pro Asp Ala Pro
305                 310                 315                 320
```

```
Tyr Val Val Leu Glu Met Arg Ser Asn Ser Gly Asp Gly Cys Phe Val
                325                 330                 335

Val Ser Val Ala Lys Asn Lys Ala Ile Ile Gly Arg Gly His Glu Ser
            340                 345                 350

Asp Val Arg Leu Ser Asp Ile Ser Val Ser Arg Met His Ala Ser Leu
        355                 360                 365

Glu Leu Asp Gly Gly Lys Val Val Ile His Asp Gln Gln Ser Lys Phe
    370                 375                 380

Gly Thr Leu Val Arg Ala Lys Ala Pro Phe Ser Met Pro Ile Lys Gly
385                 390                 395                 400

Pro Ile Cys Leu Gln Val Ser Ile Phe Phe Leu Asn Leu Lys Ile Ser
                405                 410                 415

Thr His Ser Leu Thr Met Glu Arg Gly Met Glu His Val Leu Leu
                420                 425                 430

<210> SEQ ID NO 35
<211> LENGTH: 6
<212> TYPE: PRT
<213> ORGANISM: Babesia microti
<220> FEATURE:
<221> NAME/KEY: VARIANT
<222> LOCATION: (1)...(1)
<223> OTHER INFORMATION: Xaa = Glutamic Acid or Glycine
<221> NAME/KEY: VARIANT
<222> LOCATION: (2)...(2)
<223> OTHER INFORMATION: Xaa = Alanine or Threonine
<221> NAME/KEY: VARIANT
<222> LOCATION: (3)...(3)
<223> OTHER INFORMATION: Xaa = Glycine or Valine
<221> NAME/KEY: VARIANT
<222> LOCATION: (4)...(4)
<223> OTHER INFORMATION: Xaa = Tryptophan or Glycine
<221> NAME/KEY: VARIANT
<222> LOCATION: (5)...(5)
<223> OTHER INFORMATION: Xaa = Proline or Serine

<400> SEQUENCE: 35

Xaa Xaa Xaa Xaa Xaa Ser
 1               5

<210> SEQ ID NO 36
<211> LENGTH: 32
<212> TYPE: PRT
<213> ORGANISM: Babesia microti
<220> FEATURE:
<221> NAME/KEY: VARIANT
<222> LOCATION: (6)...(6)
<223> OTHER INFORMATION: Xaa = Methionine or Isoleucine
<221> NAME/KEY: VARIANT
<222> LOCATION: (9)...(9)
<223> OTHER INFORMATION: Xaa = Tyrosine or Serine
<221> NAME/KEY: VARIANT
<222> LOCATION: (10)...(10)
<223> OTHER INFORMATION: Xaa = Serine or Phenylalanine
<221> NAME/KEY: VARIANT
<222> LOCATION: (12)...(12)
<223> OTHER INFORMATION: Xaa = Leucine or Isoleucine
<221> NAME/KEY: VARIANT
<222> LOCATION: (13)...(13)
<223> OTHER INFORMATION: Xaa = Proline, Serine or Leucine
<221> NAME/KEY: VARIANT
<222> LOCATION: (17)...(17)
<223> OTHER INFORMATION: Xaa = Leucine or Arginine
<221> NAME/KEY: VARIANT
<222> LOCATION: (19)...(19)
<223> OTHER INFORMATION: Xaa = Glutamic Acid, Aspartic Acid or Glycine
<221> NAME/KEY: VARIANT
<222> LOCATION: (20)...(20)
<223> OTHER INFORMATION: Xaa = Isoleucine or Phenylalanine
```

```
<221> NAME/KEY: VARIANT
<222> LOCATION: (21)...(21)
<223> OTHER INFORMATION: Xaa = Alanine or Valine
<221> NAME/KEY: VARIANT
<222> LOCATION: (23)...(23)
<223> OTHER INFORMATION: Xaa = Leucine or Proline
<221> NAME/KEY: VARIANT
<222> LOCATION: (26)...(26)
<223> OTHER INFORMATION: Xaa = Methionine or Threonine
<221> NAME/KEY: VARIANT
<222> LOCATION: (27)...(27)
<223> OTHER INFORMATION: Xaa = Serine or Leucine
<221> NAME/KEY: VARIANT
<222> LOCATION: (28)...(28)
<223> OTHER INFORMATION: Xaa = Valine or Phenylalanine
<221> NAME/KEY: VARIANT
<222> LOCATION: (29)...(29)
<223> OTHER INFORMATION: Xaa = Threonine or Isoleucine
<221> NAME/KEY: VARIANT
<222> LOCATION: (30)...(30)
<223> OTHER INFORMATION: Xaa = Cysteine ro Tyrosine

<400> SEQUENCE: 36

Arg Cys Leu Ser Ile Xaa Arg Phe Xaa Xaa Ser Xaa Xaa Thr Phe Ile
 1               5                  10                  15

Xaa Ile Xaa Xaa Xaa Met Xaa Phe Phe Xaa Xaa Xaa Xaa Xaa Phe Leu
            20                  25                  30

<210> SEQ ID NO 37
<211> LENGTH: 1820
<212> TYPE: DNA
<213> ORGANISM: Babesia microti

<400> SEQUENCE: 37
cggcacgagt agcccccacc atcttttgca ttcatttcaa gtttctccaa atctcgatgg     60
gacctccaat tttggctcca ccacaaacaa gtctgacata ttgagcaaaa catattgatt    120
taatttaaag aacagacatc tggccattca tgctaagagg tctcttcatt gttgagtggg    180
aacagccttg tatacgggct acaacacaca tggaaaaaca ccttgtagaa gagatcatgc    240
ttcactcagt gctagatgtt gatgccagtg atttgcttgg ggtagtaagc cagtactaga    300
atacaggatg cacttggact ggcaaacaga atacacctgt tgcctgaata gaaactcaca    360
gagacccgat gctgtctggt accaacaagg ttctgcttct gggaagaatt tacagatatt    420
atgttgggaa aagagacacc ctgtatgtgt agaaacaaag aagcacagat cttagatgaa    480
ttaatataag aatgatactt ctctagaaac aaatgtagtt accaactata ttccagaacc    540
caatgcggat tcagaatctg tacatgttga atccaggaa catgataaca tcaatccaca     600
agacgcttgc gatagtgagc cgctcgaaca atggattct gataccaggg tgttgcccga      660
aagtttggat gaggggtac cacaccaatt ctctagatta gggcaccact cagacatggc     720
atctgatata aatgatgaag aaccatcatt taaaatcggc gagaatgaca taattcaacc    780
accctgggaa gatacagctc cataccattc aatagatgat gaagagcttg caacttaat     840 gagactaacg gcgcaagaaa caagtgcga tcatgaagaa gggaatggca aactcaatac     900
gaataaaagt gagaagactg aaagaaaatc gcatgatact cagacaccgc aagaaatata    960
tgaagagctt gacaacttac tgagactaac ggcacaagaa atatatgaag agcgtaaaga   1020
agggcatggc aaacccaata cgaataaaag tgagaaggct gaaagaaaat cgcatgatac   1080
tcagacaacg caagaaatat gtgaagagtg tgaagaaggg catgacaaaa tcaataagaa   1140
taaaagtgga aatgctggaa taaaatcgta tgatactcag acaacgcaag aaatatgtga   1200
agagtgtgaa gaagggcatg acaaaatcaa taagaataaa agtggaaatg ctggaataaa   1260
```

-continued atcgtatgat actcagacac cgcaggaaac aagtgacgct catgaagaag ggcatgacaa 1320
aatcaatacg aataaaagtg agaaggctga aagaaaatcg catgatactc agacaacgca 1380
agaaatatgt gaagagtgtg aagaagggca tgacaaaatc aataagaata aaagtggaaa 1440
tgctggaata aaatcgtatg atactcagac accgcaggaa acaagtgacg ctcatgaaga 1500
agagcatggc aatctcaata agaataaaag tgggaaggct ggaataaaat cgcataatac 1560
tcagacaccg ctgaaaaaaa aagacttttg taaagaaggg tgtcatggtt gcaataataa 1620
gcccgaggat aatgaaagag acccgtcgtc gcctgatgat gatggtggct gcgaatgcgg 1680
catgacgaat cactttgtct ttgactacaa gacaacactc ttgttaaaga gcctcaagac 1740
tgaaacatcc actcattatt acattgccat ggctgcaatt tttactattt cattattccc 1800
atgcatgttt aaggctttcc 1820

<210> SEQ ID NO 38
<211> LENGTH: 445
<212> TYPE: PRT
<213> ORGANISM: Babesia microti

<400> SEQUENCE: 38

Tyr Lys Asn Asp Thr Ser Leu Glu Thr Asn Val Val Thr Asn Tyr Ile
1 5 10 15

Pro Glu Pro Asn Ala Asp Ser Glu Ser Val His Val Glu Ile Gln Glu
20 25 30

His Asp Asn Ile Asn Pro Gln Asp Ala Cys Asp Ser Glu Pro Leu Glu
35 40 45

Gln Met Asp Ser Asp Thr Arg Val Leu Pro Glu Ser Leu Asp Glu Gly
50 55 60

Val Pro His Gln Phe Ser Arg Leu Gly His His Ser Asp Met Ala Ser
65 70 75 80

Asp Ile Asn Asp Glu Glu Pro Ser Phe Lys Ile Gly Glu Asn Asp Ile
85 90 95

Ile Gln Pro Pro Trp Glu Asp Thr Ala Pro Tyr His Ser Ile Asp Asp
100 105 110

Glu Glu Leu Asp Asn Leu Met Arg Leu Thr Ala Gln Glu Thr Ser Asp
115 120 125

Asp His Glu Glu Gly Asn Gly Lys Leu Asn Thr Asn Lys Ser Glu Lys
130 135 140

Thr Glu Arg Lys Ser His Asp Thr Gln Thr Pro Gln Glu Ile Tyr Glu
145 150 155 160

Glu Leu Asp Asn Leu Leu Arg Leu Thr Ala Gln Glu Ile Tyr Glu Glu
165 170 175

Arg Lys Glu Gly His Gly Lys Pro Asn Thr Asn Lys Ser Glu Lys Ala
180 185 190

Glu Arg Lys Ser His Asp Thr Gln Thr Thr Gln Glu Ile Cys Glu Glu
195 200 205

Cys Glu Glu Gly His Asp Lys Ile Asn Lys Asn Lys Ser Gly Asn Ala
210 215 220

Gly Ile Lys Ser Tyr Asp Thr Gln Thr Thr Gln Glu Ile Cys Glu Glu
225 230 235 240

Cys Glu Glu Gly His Asp Lys Ile Asn Lys Asn Lys Ser Gly Asn Ala
245 250 255

Gly Ile Lys Ser Tyr Asp Thr Gln Thr Pro Gln Glu Thr Ser Asp Ala
260 265 270

-continued

```
His Glu Glu Gly His Asp Lys Ile Asn Thr Asn Lys Ser Glu Lys Ala
            275                 280                 285

Glu Arg Lys Ser His Asp Thr Gln Thr Thr Gln Glu Ile Cys Glu Glu
        290                 295                 300

Cys Glu Glu Gly His Asp Lys Ile Asn Lys Asn Lys Ser Gly Asn Ala
305                 310                 315                 320

Gly Ile Lys Ser Tyr Asp Thr Gln Thr Pro Gln Glu Thr Ser Asp Ala
                325                 330                 335

His Glu Glu Glu His Gly Asn Leu Asn Lys Asn Lys Ser Gly Lys Ala
            340                 345                 350

Gly Ile Lys Ser His Asn Thr Gln Thr Pro Leu Lys Lys Lys Asp Phe
        355                 360                 365

Cys Lys Glu Gly Cys His Gly Cys Asn Asn Lys Pro Glu Asp Asn Glu
    370                 375                 380

Arg Asp Pro Ser Ser Pro Asp Asp Asp Gly Gly Cys Glu Cys Gly Met
385                 390                 395                 400

Thr Asn His Phe Val Phe Asp Tyr Lys Thr Thr Leu Leu Leu Lys Ser
                405                 410                 415

Leu Lys Thr Glu Thr Ser Thr His Tyr Tyr Ile Ala Met Ala Ala Ile
            420                 425                 430

Phe Thr Ile Ser Leu Phe Pro Cys Met Phe Lys Ala Phe
        435                 440                 445
```

<210> SEQ ID NO 39
<211> LENGTH: 32
<212> TYPE: PRT
<213> ORGANISM: Babesia microti
<220> FEATURE:
<221> NAME/KEY: VARIANT
<222> LOCATION: (3)...(3)
<223> OTHER INFORMATION: Xaa = Glycine or Aspartic Acid
<221> NAME/KEY: VARIANT
<222> LOCATION: (5)...(5)
<223> OTHER INFORMATION: Xaa = Proline or Isoleucine
<221> NAME/KEY: VARIANT
<222> LOCATION: (7)...(7)
<223> OTHER INFORMATION: Xaa = Lysine or Threonine
<221> NAME/KEY: VARIANT
<222> LOCATION: (11)...(11)
<223> OTHER INFORMATION: Xaa = Glutamic Acid or Glycine
<221> NAME/KEY: VARIANT
<222> LOCATION: (12)...(12)
<223> OTHER INFORMATION: Xaa = Lysine or Asparagine
<221> NAME/KEY: VARIANT
<222> LOCATION: (14)...(14)
<223> OTHER INFORMATION: Xaa = Glutamic Acid or Glycine
<221> NAME/KEY: VARIANT
<222> LOCATION: (15)...(15)
<223> OTHER INFORMATION: Xaa = Isoleucine or Arginine
<221> NAME/KEY: VARIANT
<222> LOCATION: (18)...(18)
<223> OTHER INFORMATION: Xaa = Histidine or Tyrosine
<221> NAME/KEY: VARIANT
<222> LOCATION: (23)...(23)
<223> OTHER INFORMATION: Xaa = Threonine or Proline
<221> NAME/KEY: VARIANT
<222> LOCATION: (26)...(26)
<223> OTHER INFORMATION: Xaa = Isoleucine or Threonine
<221> NAME/KEY: VARIANT
<222> LOCATION: (27)...(27)
<223> OTHER INFORMATION: Xaa = Cysteine or Serine
<221> NAME/KEY: VARIANT
<222> LOCATION: (28)...(28)
<223> OTHER INFORMATION: Xaa = Aspartic Acid or Glutamic Acid
<221> NAME/KEY: VARIANT
<222> LOCATION: (29)...(29)
<223> OTHER INFORMATION: Xaa = Glutamic Acid or Alanine

```
<221> NAME/KEY: VARIANT
<222> LOCATION: (30)...(30)
<223> OTHER INFORMATION: Xaa = Cysteine or Histidine

<400> SEQUENCE: 39

Gly His Xaa Lys Xaa Asn Xaa Asn Lys Ser Xaa Xaa Ala Xaa Xaa Lys
 1               5                  10                  15
Ser Xaa Asp Thr Gln Thr Xaa Gln Glu Xaa Xaa Xaa Xaa Xaa Glu Glu
         20                  25                  30

<210> SEQ ID NO 40
<211> LENGTH: 2430
<212> TYPE: DNA
<213> ORGANISM: Babesia microti

<400> SEQUENCE: 40
```

| | | | | |
|---|---|---|---|---|
| tgtattgtgt | agataaaaat | gatgtttcat | tatggaaatc | aaaacctata acaactgtca | 60 |
| gtaccactaa | tgatactatt | acaaatacac | acactactaa | tgtaattaat gccaatctta | 120 |
| ttggccactt | taattataag | gatagggaac | ctttaacaat | agtatttgta tacatgatcg | 180 |
| atgaatcaga | acaaaataaa | ttatcacatc | cgaataaaat | tgataaaatc aaaatttctg | 240 |
| attatataat | tgaatttgat | gacaatgcta | aattaccaac | tggtagtgtt attgatttaa | 300 |
| acatctatac | ttgcaaacat | aataatccag | tattaattga | atttatgtt ctatagaag | 360 |
| gatctttctg | ctattatttc | tctcattgaa | taatgataca | aatgaatgga ataatcacaa | 420 |
| aataaaatat | gataaaaaat | ataagaata | tacggacatg | aatggtattc attattatta | 480 |
| tattgatggt | agtttacttg | taagtggcga | agttacatct | aattttcgtt atatttctaa | 540 |
| agaatatgaa | tatgagcata | caggattagt | aaaaaaatat | tgtaatgaag aaagatgtgt | 600 |
| aaaattggat | aacattaaga | taaggataa | taatttggaa | atttatgtga ataatttaa | 660 |
| tgaagtataa | tattatttat | aataattcaa | agattaatat | aatcaattat tataattaca | 720 |
| aaaataatta | attgtagaat | attatattat | taatcaattc | agattataaa tacatatttt | 780 |
| tacatacatt | tcaattaaa | cattcaaatt | aatgtcattt | ttatctacat tattataatt | 840 |
| ataactataa | tattcattaa | atactattaa | aaaaaatatc | ctctacatta tattaattat | 900 |
| tatagtatgt | cattatataa | catattcaca | acgtataaca | aatcaatcat taacatatac | 960 |
| atatatgata | tcattaataa | tcaatattta | attgatacaa | taatcaatag tcatctgtaa | 1020 |
| tataatcatt | gtatactaat | ttattataaa | ttattacaaa | atacactctt ttacttcatt | 1080 |
| ttatttctgt | taaatttcat | attctaatat | tatattcatc | tttctcatgt tactttaatc | 1140 |
| tatttccata | tttatcccaa | tttcttcatt | taagactgag | atgttcgttc gttcatacat | 1200 |
| aaataatgtg | taaattttgt | aatatataat | aatgtataca | tctggtatta catctatttt | 1260 |
| gtaataaata | ttaaaaaaac | ggttaaagtt | agtgccttaa | ttccaggaat tattacatta | 1320 |
| gaaactttgg | tgattttagt | gatttcggtg | atcattgaaa | gaaatggttt gaaacttgca | 1380 |
| atactgtcat | actcatcata | atccccaatg | ttggaaatca | tgatgtcaac aattttatta | 1440 |
| aattcttctg | ctgcactatt | caactcctta | atcatgtcct | caaaatgagt gttataatct | 1500 |
| ccatcctttt | tagtgatctt | atccctcaaa | actaaagctt | tagatttgga ttcgtcaaaa | 1560 |
| tttttcttga | tatcattaac | ggtattgtca | taatagaatt | tatagattaa atgttgtaat | 1620 |
| aataagtcac | aatatataaa | catatcttta | agtacaatag | acttccatat attacggaaa | 1680 |
| tggtcaaaat | tatcagcagc | tggaccttcc | aatgtaccat | aggccttgtt tgatatttca | 1740 |
| tcaaccaata | acttatatttt | tgaagagata | gtggatgcat | tatcaaatat tctagccaat | 1800 |

-continued

```
tcttctttct tcataaggga atattgttca ggaaaacatt tttccaattc ttttttcaat      1860
ttattcttct ccttggtttt ttcttcaatg tagtctttat gaccatcgtt caccctatct      1920
cgttccaata tcataacact atgtttgtat atataagata aacaaacttc attaaatata      1980
actattcttc tagaatacgg aagaagctga tatccaaatc gttcactaga ccaaccagct      2040
tcactaggcc aaccagttcc actaggccaa ccagttccac taggcccacc agcttcacta      2100
ggcccaccag cttcactagg cccaccagct tcactaggcc accagcttc actaggccaa      2160 ccagttccac taggcccacc agcttcacta ggcccaccag cttcactggg cccaacagtt      2220
ccactaggcc accagcttc actaggccca ccagcttcgg gatcggtatc acttgcaaag      2280
acagcaccgc tcattaaaaa gagtgtaata taaggaacta atattgattt aaatgacacc      2340
atctttataa accatagtta ttggtacatt attagtacat tattggtata tgattggtac      2400
gtggtagtga ttgtggtgct gcatctagtt                                       2430
```

<210> SEQ ID NO 41
<211> LENGTH: 128
<212> TYPE: PRT
<213> ORGANISM: Babesia microti

<400> SEQUENCE: 41

```
Tyr Cys Val Asp Lys Asn Asp Val Ser Leu Trp Lys Ser Lys Pro Ile
 1               5                  10                  15

Thr Thr Val Ser Thr Thr Asn Asp Thr Ile Thr Asn Thr His Thr Thr
            20                  25                  30

Asn Val Ile Asn Ala Asn Leu Ile Gly His Phe Asn Tyr Lys Asp Arg
        35                  40                  45

Glu Pro Leu Thr Ile Val Phe Val Tyr Met Ile Asp Glu Ser Glu Gln
    50                  55                  60

Asn Lys Leu Ser His Pro Asn Lys Ile Asp Lys Ile Lys Ile Ser Asp
65                  70                  75                  80

Tyr Ile Ile Glu Phe Asp Asp Asn Ala Lys Leu Pro Thr Gly Ser Val
                85                  90                  95

Ile Asp Leu Asn Ile Tyr Thr Cys Lys His Asn Asn Pro Val Leu Ile
            100                 105                 110

Glu Phe Tyr Val Ser Ile Glu Gly Ser Phe Cys Tyr Tyr Phe Ser His
        115                 120                 125
```

<210> SEQ ID NO 42
<211> LENGTH: 1271
<212> TYPE: DNA
<213> ORGANISM: Babesia microti

<400> SEQUENCE: 42

```
tgagaaaacg catataattg taactacgcc agagaagttt gacgtagtta cacgtaaaac        60
aggcaatgag ccctgcttg agcggcttag attggttata attgatgaaa tacacctact       120
ccatgacact aggggtccag tgctggaggc tattgtggcc cgcctgagtc agaggcccga       180
acgcgtaagg ctagttggtc tatcggccac gcttccaaac tacgaagacg tggctagatt       240
tctcactgtt aatctagacc gagggctttt ctacttggc agccacttta ggcctgtgcc       300
cttggagcag gtgtattatg gcgtgaagga gaagaaggct atcaaacgtt caacgcaat       360 caacgaaatt ctctaccaag aggtgattaa cgatgtttct agctgccaaa ttcttgtttt       420
tgtgcattct agaaaggaaa cgtacaggac ggcaaaattt atcaaagaca cggccctttc       480
```

```
acgggacaac ttgggagcct aaaccctaaa ccctaaaccc taaaccctaa ccctaaaccc    540
taaaccctaa accctaaacc ctaaaccctaa accctaaccc taaccctaac cctaacctag    600
ccttcattga cgtctatccc caatcttaga aaaatcttca aatcgattct agaataactg    660
gaagcaatta tcagaaattg tataactgct tattagctta ttagcttatt agttaggatg    720
tatgcacatt gatgacaact agatgcagca ccacaatcac taccacgtac caatcatata    780
ccaataatgt actaataatg taccaataac tatggtttat aaagatggtg tcatttaaat    840
caatattagt tccttatatt acactctttt taatgagcgg tgctgtcttt gcaggtgata    900
ccgatcgcga agctggtggg cctagtggaa ctgttgggcc tagtgaagct ggtgggccta    960
gtgaagctgg tgggcctagt gaagctggtg ggcctagtga agctggtggg cctagtgaag   1020
ctggtgggcc tagtgaagct ggtgggccta gtgaagctgt gggcctagt gaagctggtg   1080 ggcctagtgg aactggttgg cctagtgaag ctggtgggcc tagtgaagct ggtgggccta   1140
gtgaagctgg tgggcctagt ggaactggtt ggcctagtga agctggttgg cctagtgaag   1200
ctggttggcc tagtgaagct ggttggccta gtgaagctgg ttggcctagt gaagctggtt   1260
ggcctagtga a                                                       1271
```

<210> SEQ ID NO 43
<211> LENGTH: 166
<212> TYPE: PRT
<213> ORGANISM: Babesia microti

<400> SEQUENCE: 43

```
Glu Lys Thr His Ile Ile Val Thr Thr Pro Glu Lys Phe Asp Val Val
 1               5                  10                  15

Thr Arg Lys Thr Gly Asn Glu Pro Leu Leu Glu Arg Leu Arg Leu Val
                20                  25                  30

Ile Ile Asp Glu Ile His Leu Leu His Asp Thr Arg Gly Pro Val Leu
            35                  40                  45

Glu Ala Ile Val Ala Arg Leu Ser Gln Arg Pro Glu Arg Val Arg Leu
        50                  55                  60

Val Gly Leu Ser Ala Thr Leu Pro Asn Tyr Glu Asp Val Ala Arg Phe
65                  70                  75                  80

Leu Thr Val Asn Leu Asp Arg Gly Leu Phe Tyr Phe Gly Ser His Phe
                85                  90                  95

Arg Pro Val Pro Leu Glu Gln Val Tyr Tyr Gly Val Lys Glu Lys
               100                 105                 110

Ala Ile Lys Arg Phe Asn Ala Ile Asn Glu Ile Leu Tyr Gln Glu Val
            115                 120                 125

Ile Asn Asp Val Ser Ser Cys Gln Ile Leu Val Phe Val His Ser Arg
        130                 135                 140

Lys Glu Thr Tyr Arg Thr Ala Lys Phe Ile Lys Asp Thr Ala Leu Ser
145                 150                 155                 160

Arg Asp Asn Leu Gly Ala
                165
```

<210> SEQ ID NO 44
<211> LENGTH: 154
<212> TYPE: PRT
<213> ORGANISM: Babesia microti

<400> SEQUENCE: 44

```
Leu Trp Phe Ile Lys Met Val Ser Phe Lys Ser Ile Leu Val Pro Tyr
 1               5                  10                  15
```

```
Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
    50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Glu Ala Gly Gly Pro Ser Glu Ala Gly Gly Pro Ser Glu
            100                 105                 110

Ala Gly Gly Pro Ser Gly Thr Gly Trp Pro Ser Glu Ala Gly Trp Pro
            115                 120                 125

Ser Glu Ala Gly Trp Pro Ser Glu Ala Gly Trp Pro Ser Glu Ala Gly
        130                 135                 140

Trp Pro Ser Glu Ala Gly Trp Pro Ser Glu
145                 150
```

<210> SEQ ID NO 45
<211> LENGTH: 4223
<212> TYPE: DNA
<213> ORGANISM: Babesia microti

<400> SEQUENCE: 45

```
ctcgtgcctt tctcaactga taacagctaa caaaaagtct cttatcttaa accatcctat      60
acctcgtatt ataatatgaa aagggccttt tctaaatctt tccccaaagt tctgctattt     120
aattaaaaaa aaaaaagact cattcaataa acgggtgggg cagaaagggt acctttccaa     180
gtgttcttcc atgacgaccc acaatgcaaa gttcttctta caaagaaaag agaaagatcc     240
actgagtgat aagtaaccca gctggggccg gcggtggtg cgcacacct ttaatcccag       300
cactcgggag gcagaggcag gcggatctct gtgagttcga gaccaggctg gaccgacagc     360
ctccaaaaca atacagagaa accctgtctc ataaaaaacc aaaaaaaaag taacccagct     420
ggatttggta actgtctcag aaacagacta tataaaccct catcaccccta caacaagtag    480
gaagctagcg ctccccaccc catcccaaca cacacacaca cacacacaca cacacacaca    540
cacacacaca cacgcacaca cgcacgcacg cacacacgca cgcacgcaca cacgcacaca    600
cgcacgcaca cacgcacaca cgcacgcacg cacgcacgca cgcacgcacg cacgcccttc    660
tgtgtctgtt ctgttcaaga agggtaccac aaaaaagtac cttatggcca catcaatgac    720
aattattact gtatataaaa tgccccccatg gatggcattg tattgtcgaa attaaaggca    780
ccccccgaaag aacagcacag agggctacc accaattaac tcccaggagg aaataaagac    840
agaagtgtga aggagggaga gagggaggga ggaagggagg gagaaaagga gggaaaggaa    900
caaggagtaa cagggacaaa agcagcagat ggtgccaggc aggagtgtgc ctaccacacc    960
gggccttccc gttacttcat ttactctcct ttgcagcctg gaataaaaca agtcacgcgt    1020
caccccggtgt ctcaagctca gcatggcttg atctgagtgc ccgtgtatgt gttcattcta   1080
taactgattt aaggaacaac tttctgctca ttgcctctat cttctcaaac atttcgaagc    1140
agttattttt tataagaaaa tataaaacag gccgactaaa ttcgatcttt ctctccccag    1200
ctgctagttt cttatctagc tgctttaggc agtctccaca gattgcagcc aggcccctat    1260
tctcaattcc atctgacttc tgacagcgct ctccatttct tatttgcagc ttagacatct    1320
```

-continued

```
tcactgagag caggagtaat tcattcaaat gacaatgagg tatctgaata tcacacaaac    1380
acttcaaatt ctgtttattg gaaatagatc tgctcctgcc ccatcataac aatccttttt    1440
atcttactta acagggcaa gaaaatcttt cacttcattt cctatcatct caaatgagtt     1500
cctgtacatg aatgacttaa ggtaaccata tccaacaact tgaagccaac cagtccctgg    1560
tcctactaca gacgttaggg aacatatgtg aaaacctggt gtacaaccta atcataact     1620 agacagaaga cagcactatt tcctggtcac atagaaagca gaatagcatc ctcacaccaa    1680
tgaggaaaat gtcatgaagg caggagagat catgactgag gtgatacttt taccaaagac    1740
ttgccagtga ttaatttctc aattagttag caaaaaatat ggctctctag tgaatttgtg    1800
tccacaccat tttccagatg ttttgatgtc acttaaatca atctaattat ttaagttaaa    1860
aaatgttaca gatcattgct ttttttcttt tttagaagac atcaaaacaa taggatttct    1920
atgaaatatt ctcacttcac agctgtgtca gttaaagtgc tttgggttat acataaagaa    1980
aacagactca agaaagtaag aacaggaatt tggagcttgc aacactgatg ttctttgtaa    2040
aaagagagac tttatccagg gattagattc tgtcacaagg cctggaactc tctcttctca    2100
gccttatttc cccaatatgg attagaatct tacactgcaa gcttcccaca agggtggaca    2160
ggtcctcacc atttgtttca gcaggaaaaa gagtctgtat gcatccgtga tatctaagtc    2220
acaattccag aagtgagctt tcctggctcc tattggtcgg acttaggtca ggtgtcacat    2280 ttcctttttgg attagtctgt gattaatgaa tgggcccact ttgctcaccc attaagacaa    2340
taggcttcca ttctcgaagc tggaagcatg acatgtccca cagaaactgt aataagagag    2400
aacataggtt gctgtgtgga gaaacgaggc aaccggcaag tcataagatg acaaagtctt    2460
ggaaagtcta agtcagtggt tctcagcctt ccctaaaccc taaaccctaa accctaaacc    2520
ctaaacccta aaccctaaac ccctaaaccc taaaccctaa accctaaacc ctaaacccta    2580
accctaaacc ctaaacccta aaccctaaac ctaaaccct aaccctaacc ctaacccta     2640 ccctaaccta gccttcattg acgtctatcc ccaatcttag aaaaatcttc aaatcgattc    2700
tagaataact ggaagcaatt atcagaaatt gtataactgc ttattagctt attagcttat    2760
tagttaggat gtatgcacat tgatgacaac tagatgcagc accacaatca ctaccacgta    2820
ccaatcatat accaataatg tactaataat gtaccaataa ctatggttta taagatggt     2880 gtcatttaaa tcaatattag ttccttatat tacactcttt ttaatgagcg gtgctgtctt    2940
tgcaggtgat accgatcgcg aagctggtgg gcctagtgga actgttgggc ctagtgaagc    3000
tggtgggcct agtgaagctg gtgggcctag tgaagctggt gggcctagtg aagctggtgg    3060
gcctagtgaa gctggtgggc ctagtgaagc tggtgggcct agtgaagctg gtgggcctag    3120
tggaactgtt gggcctagtg aagctggtgg gcctagtgaa gctggtgggc ctagtgaagc    3180
tggtgggcct agtgaagctg gttggcctag tgaagctggt tggcctagtg aagctggttg    3240
gcctagtgaa gctggttggc ctagtgaagc tggttggcct agtgaagctg gttggcctag    3300
tgaacgattt ggatatcagc ttctttggta ttctagaaga atagttatat ttaatgaaat    3360
ttatttatct catatatacg aacatagtgt tatgatattg aacgagata gggtgaacga     3420 tggtcataaa gactacattg aagaaaaaac caaggagaag aataaattga aaaagaatt     3480 ggaaaaatgt tttcctgaac aatattccct tatgaagaaa gaagaattgg ctagaataat    3540
tgataatgca tccactatct cttcaaaata taagttattg gttgatgaaa tatccaacaa    3600
agcctatggt acattggaag gtccagctgc tgatgatttt gaccatttcc gtaatatatg    3660
```

-continued

```
gaagtctatt gtacctaaaa atatgtttct atattgtgac ttattattaa aacatttaat    3720
ccgtttaacc cccagaaaga gctgaccaga caaaggttaa ctcttgaatc ccaggcatca    3780
gcctgggaat ccatcatggg actgatcaag accccctgaa tgtgggtgtc agtgaggagg    3840
cctaggtaat ctattgagcc tcgggcagca gatcagtacc catcccaatt atacacaatt    3900
gcagtgttgt ggtttcacag tgaataattg taggtcacag tccattatat tgatgtcaca    3960
gtttttaatt gtcatgtcac agtgcaagct agtgatgtca gagtgtataa ctgtgttcat    4020
agagaatgta ttgatgtcac agtcaataat cgtgatgtca tagtgcagta tattgatgtc    4080
acaatgtata attgtgatgt taaagtgcaa gatagtgaag tcacagtata taattgtgat    4140
gtcatattgc attataatga tgtcacactt tataattttt tacatacagc actatagtga    4200
tgtaacagcc aataattgtg atg                                            4223
```

<210> SEQ ID NO 46
<211> LENGTH: 294
<212> TYPE: PRT
<213> ORGANISM: Babesia microti

<400> SEQUENCE: 46

```
Leu Trp Phe Ile Lys Met Val Ser Phe Lys Ser Ile Leu Val Pro Tyr
  1               5                  10                  15

Ile Thr Leu Phe Leu Met Ser Gly Ala Val Phe Ala Gly Asp Thr Asp
             20                  25                  30

Arg Glu Ala Gly Gly Pro Ser Gly Thr Val Gly Pro Ser Glu Ala Gly
         35                  40                  45

Gly Pro Ser Glu Ala Gly Gly Pro Ser Glu Ala Gly Gly Pro Ser Glu
     50                  55                  60

Ala Gly Gly Pro Ser Glu Ala Gly Gly Pro Ser Glu Ala Gly Gly Pro
 65                  70                  75                  80

Ser Glu Ala Gly Gly Pro Ser Gly Thr Val Gly Pro Ser Glu Ala Gly
                 85                  90                  95

Gly Pro Ser Glu Ala Gly Gly Pro Ser Glu Ala Gly Gly Pro Ser Glu
            100                 105                 110

Ala Gly Trp Pro Ser Glu Ala Gly Trp Pro Ser Glu Ala Gly Trp Pro
        115                 120                 125

Ser Glu Ala Gly Trp Pro Ser Glu Ala Gly Trp Pro Ser Glu Ala Gly
    130                 135                 140

Trp Pro Ser Glu Arg Phe Gly Tyr Gln Leu Leu Trp Tyr Ser Arg Arg
145                 150                 155                 160

Ile Val Ile Phe Asn Glu Ile Tyr Leu Ser His Ile Tyr Glu His Ser
                165                 170                 175

Val Met Ile Leu Glu Arg Asp Arg Val Asn Asp Gly His Lys Asp Tyr
            180                 185                 190

Ile Glu Glu Lys Thr Lys Glu Lys Asn Lys Leu Lys Lys Glu Leu Glu
        195                 200                 205

Lys Cys Phe Pro Glu Gln Tyr Ser Leu Met Lys Lys Glu Glu Leu Ala
    210                 215                 220

Arg Ile Ile Asp Asn Ala Ser Thr Ile Ser Ser Lys Tyr Lys Leu Leu
225                 230                 235                 240

Val Asp Glu Ile Ser Asn Lys Ala Tyr Gly Thr Leu Glu Gly Pro Ala
                245                 250                 255

Ala Asp Asp Phe Asp His Phe Arg Asn Ile Trp Lys Ser Ile Val Pro
            260                 265                 270
```

Lys Asn Asn Phe Leu Tyr Cys Asp Leu Leu Lys His Leu Ile Arg
            275                 280                 285

Leu Thr Pro Arg Lys Ser
        290

<210> SEQ ID NO 47
<211> LENGTH: 30
<212> TYPE: PRT
<213> ORGANISM: Artificial Sequence
<220> FEATURE:
<223> OTHER INFORMATION: Synthetic peptide of repeat region of antigen
      BMNI-3 (SEQ ID NO:3)

<400> SEQUENCE: 47

Ser Glu Ala Gly Gly Pro Ser Glu Ala Gly Pro Ser Gly Thr Gly
  1               5                  10                  15

Trp Thr Ser Gly Thr Gly Trp Pro Ser Glu Ala Gly Trp Ser
                 20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic peptide of repeat region of antigen
      BMNI-3 (SEQ ID NO:3)

<400> SEQUENCE: 48

Glu Ala Gly Gly Pro Ser Gly Thr Val Gly Pro Ser Gly Thr Gly Trp
  1               5                  10                  15

Pro Ser Glu Ala Gly Trp Gly Ser Glu Ala Gly Trp Ser Ser
                 20                  25                  30

<210> SEQ ID NO 49
<211> LENGTH: 367
<212> TYPE: PRT
<213> ORGANISM: Babesia microti

<400> SEQUENCE: 49

Met Val Ser Phe Lys Ser Ile Leu Val Pro Tyr Ile Thr Leu Phe Leu
  1               5                  10                  15

Met Ser Gly Ala Val Phe Ala Ser Asp Thr Asp Pro Glu Ala Gly Gly
                 20                  25                  30

Pro Ser Glu Ala Gly Gly Pro Ser Gly Thr Val Gly Pro Ser Glu Ala
             35                  40                  45

Gly Gly Pro Ser Glu Ala Gly Gly Pro Ser Gly Thr Gly Trp Pro Ser
 50                  55                  60

Glu Ala Gly Gly Pro Ser Glu Ala Gly Gly Pro Ser Glu Ala Gly Gly
 65                  70                  75                  80

Pro Ser Glu Ala Gly Pro Ser Gly Thr Gly Ser Glu Ala Gly Gly
                 85                  90                  95

Trp Pro Ser Gly Thr Gly Trp Pro Ser Glu Ala Gly Trp Ser Ser Glu
                100                 105                 110

Arg Phe Gly Tyr Gln Leu Leu Pro Tyr Ser Arg Arg Ile Val Ile Phe
            115                 120                 125

Asn Glu Val Cys Leu Ser Tyr Ile Tyr Lys His Ser Val Met Ile Leu
        130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro

```
                165                 170                 175
Glu Gln Tyr Ser Leu Met Lys Lys Glu Leu Ala Arg Ile Phe Asp
                    180                 185                 190
Asn Ala Ser Thr Ile Ser Ser Lys Tyr Lys Leu Leu Val Asp Glu Ile
            195                 200                 205
Ser Asn Lys Ala Tyr Gly Thr Leu Glu Gly Pro Ala Ala Asp Asn Phe
    210                 215                 220
Asp His Phe Arg Asn Ile Trp Lys Ser Ile Val Leu Lys Asp Met Phe
225                 230                 235                 240
Ile Tyr Cys Asp Leu Leu Gln His Leu Ile Tyr Lys Phe Tyr Tyr
                245                 250                 255
Asp Asn Thr Val Asn Asp Ile Lys Lys Asn Phe Asp Glu Ser Lys Ser
            260                 265                 270
Lys Ala Leu Val Leu Arg Asp Lys Ile Thr Lys Lys Asp Gly Asp Tyr
                275                 280                 285
Asn Thr His Phe Glu Asp Met Ile Lys Glu Leu Asn Ser Ala Ala Glu
    290                 295                 300
Glu Phe Asn Lys Ile Val Asp Ile Met Ile Ser Asn Ile Gly Asp Tyr
305                 310                 315                 320
Asp Glu Tyr Asp Ser Ile Ala Ser Phe Lys Pro Phe Leu Ser Met Ile
                325                 330                 335
Thr Glu Ile Thr Lys Ile Thr Lys Val Ser Asn Val Ile Ile Pro Gly
            340                 345                 350
Ile Lys Ala Leu Thr Leu Thr Val Phe Leu Ile Phe Ile Thr Lys
        355                 360                 365

<210> SEQ ID NO 50
<211> LENGTH: 1908
<212> TYPE: DNA
<213> ORGANISM: Babesia microti

<400> SEQUENCE: 50
aaaagattta atgaacatac tgacatgaat ggtattcatt attattatat tgatggtagt      60
ttacttgcga gtggcgaagt tacatctaat tttcgttata tttctaaaga atatgaatat     120
gagcatacag aattagcaaa agagcattgc aagaaagaaa atgtgtaaa tgtggataac     180
attgaggata taatttgaa atatatgcg aaacagttta atctgtagt tactactcca       240
gctgatgtag cgggtgtgtc agatggattt tttatacgtg gccaaaatct tggtgctgtg    300
ggcagtgtaa atgaacaacc taatactgtt ggtatgagtt tagaacaatt catcaagaac    360
gagctttatt cttttagtaa tgaaatttat catacaatat ctagtcaaat cagtaattct    420
ttcttaataa tgatgtctga tgcaattgtt aaacatgata actatatttt aaaaaagaa    480
ggtgaaggct gtgaacaaat ctacaattat gaggaattta tagaaaagtt gagggggtgct  540
agaagtgagg ggaataatat gtttcaggaa gctctgataa ggtttaggaa tgctagtagt    600
gaagaaatgg ttaatgctgc aagttatcta tccgccgccc ttttcagata taggaatttt    660
gatgatgaat tattcaaaaa ggccaacgat aattttggac gcgatgatgg atatgatttt    720
gattatataa atacaaagaa agagttagtt atacttgcca gtgtgttgga tggtttggat    780
ttaataatgg aacgtttgat cgaaaatttc agtgatgtca ataatacaga tgatattaag    840
aaggcatttg acgaatgcaa atctaatgct attatattga agaaaaagat acttgacaat    900
gatgaagatt ataagattaa ttttagggaa atggtgaatg aagtaacatg tgcaaacaca    960
aaatttgaag ccctaaatga tttgataatt tccgactgtg agaaaaaagg tattaagata   1020
```

```
aacagagatg tgatttcaag ctacaaattg cttctttcca caatcaccta tattgttgga    1080
gctggagttg aagctgtaac tgttagtgtg tctgctacat ctaatggaac tgaatctggt    1140
ggagctggta gtggaactgg aactagtgtg tctgctacat ctactttaac tggtaatggt    1200
ggaactgaat ctggtggaac agctggaact actacgtcta gtggaactga agctggtgga    1260
actagtggaa ctactacgtc tagtggagct gctagtggta agctggaaac tggaacagct    1320
ggaactacta cgtctagtga aggtgctggt agtgataaag ctggaactgg aactagtgga    1380
actactacgt ctagtggaac tggtgctggt ggagctggta gtggtggacc tagtggacat    1440
gcttctaatg caaaaattcc tggaataatg acactaactc tatttgcatt attaacattt    1500
attgtaaatt gaatgaaaca catgatttat acattattat atattacaaa atttacacat    1560
tatttatgta tgaacgaacg aacatcttgc tcttaaataa agaaattgag atatatatgg    1620
aaatagatta aagtaacatg agaaagatga atataatatt agaatatgaa atttaacaga    1680
aataaaatga agtaaaagag tgtattttgt aataatttat aataaattag tatacaatga    1740
ttatattaca aatggctatt aaatatttta ttaattaaat attgattagt aatgatatta    1800
tgtatgtaca tgttagggtt gattgttata cattgtgaat atattatata attgtatatt    1860
atattgattg atataatgta gaggatattt ttttaaatag tatttaat                1908
```

<210> SEQ ID NO 51
<211> LENGTH: 1460
<212> TYPE: DNA
<213> ORGANISM: Babesia microti
<400> SEQUENCE: 51

```
aatccaacat ctagcctagt tagtatatat aggttaatat cacattatag attatctttg     60
gatgattggt tattatataa catgtcgctg aatgacgatt attttgctag ataatataac    120
taccggtgat tctgaggacc tactttaaag agaataatta acatatctac cagaatcagt    180 tccaattttat gtattttaaa gctaatcact actcgaaaac tacggtgaaa atggaaaaac    240
aagtggaagc tgtatgtcgt ggaaagtcac tacattttat gtgggcaaat ttaataattc    300
taaatactat gtttttgatg ttaaaaagcg aaaaacacac tttaatgcac attttaacat    360
catctgtata atatatatat cagcgttgaa atcatatggc aaaggtaata aagcgttaca    420
ttttgagcga ataaaggcac atatgcaaac gtatgaagcc ttgtatattt gtggaattat    480
attatgctag taatttgtga ttaataatgg caatatttat atacaaatat tcgagcgttc    540
tattatatgc atgcacataa ttaatcacaa actctcatat catggggcgg tttcgcccat    600
cataaacatt actgttagca ctctggtaga ttagcatggt gaatctctcg atacctgggc    660
tactgttgct ttccgcatat tccttaaatt ctgcaagtgc gggggatgta tatgagatat    720
cttctggtaa tccacccgac atagagccaa catctacttc tctagaaaca aatgtagtta    780
ccaactatat tccagaaccc aatgcggatt cagaatctgt acatgttgaa atccaggaac    840
atgataacat caatccacaa gacgcttgcg atagtgagcc gctcgaacaa atggattctg    900
ataccagggt gttgcccgaa gtttggatg aggggtacc acaccaattc tctagattag    960
ggcaccactc agacatggca tctgatataa atgatgaaga accatcattt aaaatcggcg   1020
agaatgacat aattcaacca ccctgggaag atacagctcc ataccattca atagatgatg   1080
aagagcttga caacttaatg agactaacgg cgcaagaaac aagtgacgat catgaagaag   1140
ggaatggcaa actcaatacg aataaaagtg agaagactga agaaaatcg catgatactc   1200
```

```
agacaccgca agaaatatat gaagagcttg acaacttact gagactaacg gcacaagaaa    1260
tatatgaaga gcgtaaagaa gggcatggca aacccaatac gaataaaagt gagaaggctg    1320
aaagaaaatc gcatgatact cagacaacgc aagaaatatg tgaagagtgt gaagaagggc    1380
atgacaaaat caataagaat aaaagtggaa atgctggaat aaaatcgtat gatactcaga    1440
caccgcagga aacaagtgac                                                1460

<210> SEQ ID NO 52
<211> LENGTH: 503
<212> TYPE: PRT
<213> ORGANISM: Babesia microti

<400> SEQUENCE: 52

Lys Arg Phe Asn Glu His Thr Asp Met Asn Gly Ile His Tyr Tyr Tyr
  1               5                  10                  15

Ile Asp Gly Ser Leu Leu Ala Ser Gly Glu Val Thr Ser Asn Phe Arg
             20                  25                  30

Tyr Ile Ser Lys Glu Tyr Glu Tyr Glu His Thr Glu Leu Ala Lys Glu
         35                  40                  45

His Cys Lys Lys Glu Lys Cys Val Asn Val Asp Asn Ile Glu Asp Asn
     50                  55                  60

Asn Leu Lys Ile Tyr Ala Lys Gln Phe Lys Ser Val Val Thr Thr Pro
 65                  70                  75                  80

Ala Asp Val Ala Gly Val Ser Asp Gly Phe Phe Ile Arg Gly Gln Asn
                 85                  90                  95

Leu Gly Ala Val Gly Ser Val Asn Glu Gln Pro Asn Thr Val Gly Met
            100                 105                 110

Ser Leu Glu Gln Phe Ile Lys Asn Glu Leu Tyr Ser Phe Ser Asn Glu
        115                 120                 125

Ile Tyr His Thr Ile Ser Ser Gln Ile Ser Asn Ser Phe Leu Ile Met
    130                 135                 140

Met Ser Asp Ala Ile Val Lys His Asp Asn Tyr Ile Leu Lys Lys Glu
145                 150                 155                 160

Gly Glu Gly Cys Glu Gln Ile Tyr Asn Tyr Glu Phe Ile Glu Lys
                165                 170                 175

Leu Arg Gly Ala Arg Ser Glu Gly Asn Asn Met Phe Gln Glu Ala Leu
            180                 185                 190

Ile Arg Phe Arg Asn Ala Ser Ser Glu Glu Met Val Asn Ala Ala Ser
        195                 200                 205

Tyr Leu Ser Ala Ala Leu Phe Arg Tyr Lys Glu Phe Asp Asp Glu Leu
    210                 215                 220

Phe Lys Lys Ala Asn Asp Asn Phe Gly Arg Asp Asp Gly Tyr Asp Phe
225                 230                 235                 240

Asp Tyr Ile Asn Thr Lys Lys Glu Leu Val Ile Leu Ala Ser Val Leu
                245                 250                 255

Asp Gly Leu Asp Leu Ile Met Glu Arg Leu Ile Glu Asn Phe Ser Asp
            260                 265                 270

Val Asn Asn Thr Asp Asp Ile Lys Lys Ala Phe Asp Glu Cys Lys Ser
        275                 280                 285

Asn Ala Ile Ile Leu Lys Lys Lys Ile Leu Asp Asn Asp Glu Asp Tyr
    290                 295                 300

Lys Ile Asn Phe Arg Glu Met Val Asn Glu Val Thr Cys Ala Asn Thr
305                 310                 315                 320

Lys Phe Glu Ala Leu Asn Asp Leu Ile Ile Ser Asp Cys Glu Lys Lys
```

```
                        325                 330                 335
Gly Ile Lys Ile Asn Arg Asp Val Ile Ser Ser Tyr Lys Leu Leu Leu
                340                 345                 350
Ser Thr Ile Thr Tyr Ile Val Gly Ala Gly Val Glu Ala Val Thr Val
                355                 360                 365
Ser Val Ser Ala Thr Ser Asn Gly Thr Glu Ser Gly Gly Ala Gly Ser
            370                 375                 380
Gly Thr Gly Thr Ser Val Ser Ala Thr Ser Thr Leu Thr Gly Asn Gly
385                 390                 395                 400
Gly Thr Glu Ser Gly Gly Thr Ala Gly Thr Thr Ser Ser Gly Thr
                405                 410                 415
Glu Ala Gly Gly Thr Ser Gly Thr Thr Thr Ser Ser Gly Ala Ala Ser
                420                 425                 430
Gly Lys Ala Gly Thr Gly Thr Ala Gly Thr Thr Thr Ser Ser Glu Gly
                435                 440                 445
Ala Gly Ser Asp Lys Ala Gly Thr Gly Thr Ser Gly Thr Thr Thr Ser
            450                 455                 460
Ser Gly Thr Gly Ala Gly Gly Ala Gly Ser Gly Gly Pro Ser Gly His
465                 470                 475                 480
Ala Ser Asn Ala Lys Ile Pro Gly Ile Met Thr Leu Thr Leu Phe Ala
                485                 490                 495
Leu Leu Thr Phe Ile Val Asn
                500

<210> SEQ ID NO 53
<211> LENGTH: 275
<212> TYPE: PRT
<213> ORGANISM: Babesia microti

<400> SEQUENCE: 53

Met Val Asn Leu Ser Ile Pro Gly Leu Leu Leu Ser Ala Tyr Ser
  1               5                  10                  15
Leu Asn Ser Ala Ser Ala Gly Asp Val Tyr Glu Ile Ser Ser Gly Asn
                20                  25                  30
Pro Pro Asp Ile Glu Pro Thr Ser Thr Ser Leu Glu Thr Asn Val Val
            35                  40                  45
Thr Asn Tyr Ile Pro Glu Pro Asn Ala Asp Ser Glu Ser Val His Val
 50                  55                  60
Glu Ile Gln Glu His Asp Asn Ile Asn Pro Gln Asp Ala Cys Asp Ser
 65                  70                  75                  80
Glu Pro Leu Glu Gln Met Asp Ser Asp Thr Arg Val Leu Pro Glu Ser
                85                  90                  95
Leu Asp Glu Gly Val Pro His Gln Phe Ser Arg Leu Gly His His Ser
                100                 105                 110
Asp Met Ala Ser Asp Ile Asn Asp Glu Glu Pro Ser Phe Lys Ile Gly
                115                 120                 125
Glu Asn Asp Ile Ile Gln Pro Arg Trp Glu Asp Thr Ala Pro Tyr His
                130                 135                 140
Ser Ile Asp Asp Glu Glu Leu Asp Asn Leu Met Arg Leu Thr Ala Gln
145                 150                 155                 160
Glu Thr Ser Asp Asp His Glu Glu Gly Asn Gly Lys Leu Asn Thr Asn
                165                 170                 175
Lys Ser Glu Lys Thr Glu Arg Lys Ser His Asp Thr Gln Thr Pro Gln
                180                 185                 190
```

Glu Ile Tyr Glu Glu Leu Asp Asn Leu Leu Arg Leu Thr Ala Gln Glu
            195                 200                 205

Ile Tyr Glu Glu Arg Lys Glu Gly His Gly Lys Pro Asn Thr Asn Lys
    210                 215                 220

Ser Glu Lys Ala Glu Arg Lys Ser His Asp Thr Gln Thr Thr Gln Glu
225                 230                 235                 240

Ile Cys Glu Glu Cys Glu Glu Gly His Asp Lys Ile Asn Lys Asn Lys
                245                 250                 255

Ser Gly Asn Ala Gly Ile Lys Ser Tyr Asp Thr Gln Thr Pro Gln Glu
            260                 265                 270

Thr Ser Asp
        275

<210> SEQ ID NO 54
<211> LENGTH: 22
<212> TYPE: DNA
<213> ORGANISM: Artificial Sequence
<220> FEATURE:
<223> OTHER INFORMATION: PCR Primer

<400> SEQUENCE: 54
tttgcaggtg ataccgatcg cg                                              22

<210> SEQ ID NO 55
<211> LENGTH: 24
<212> TYPE: DNA
<213> ORGANISM: Artificial Sequence
<220> FEATURE:
<223> OTHER INFORMATION: PCR Primer

<400> SEQUENCE: 55
tggtattcta gaagaatagt tata                                            24

<210> SEQ ID NO 56
<211> LENGTH: 306
<212> TYPE: DNA
<213> ORGANISM: Babesia microti

<400> SEQUENCE: 56
ttgcaggtga taccgatcgc gaagctggtg ggcctagtgg aactgttggg cccagtgaag      60
ctggtgggcc tagtgaagct ggtgggccta gtggaactgt tgggcccagt gaagctggtg     120
ggcctagtga agctggtggg cctagtggaa ctggttggcc tagtgaagct ggtgggccta     180
gtggaactgt tgggcccagt gaagctggtg ggcctagtga agctggtggg cctagtggaa     240
ctggttggcc tagtggaact ggttggccta gtgaagttgg ttggcccatt gaaccatttg     300
gatatc                                                               306

<210> SEQ ID NO 57
<211> LENGTH: 318
<212> TYPE: DNA
<213> ORGANISM: Babesia microti

<400> SEQUENCE: 57
ttgcaggtga taccgatcgc gaagctggtg ggcctagtgg aactgttggg cccagtgaag      60
ctggtgggcc tagtgaagct ggtgggccta gtggaactgt tgggcccagt gaagctggtg     120
ggcctagtga agctggtggg cctagtggaa ctggttggcc tagtgaagct ggtgggccta     180
gtggaactgt tgggcccagt gaagctggtg ggcctagtga agctggtggg cctagtggaa     240
ctggttggcc tagtggaact ggttggccta gtgaagttgg ttggcctaat gaaccatttg     300

```
gatatcacct tctttggt                                               318
```

<210> SEQ ID NO 58
<211> LENGTH: 358
<212> TYPE: DNA
<213> ORGANISM: Babesia microti

<400> SEQUENCE: 58

```
ttgcaggtga taccgatcgc gaagctggtg ggcctagtgg aactgttggg cctagtgaag    60
ctggtgggcc tagtgaagct ggtgggccta gtgaagctgt gggcctagt gaagctggtg   120
ggcctagtga agctggtggg cctagtgaag ctggtgggcc tagtgaagct ggtgggccta   180
gtgaagctgg tgggcctagt gaagctggtg ggcctagtga agctggttgg cctagtgaag   240
ctggttggcc tagtgaagct ggtgggccta gtggaactgg ttggcctagt gaagctggtt   300
ggcctagtga agctggttgg cctagtgaag ctggttggcc tagtgaagct ggttggcc     358
```

<210> SEQ ID NO 59
<211> LENGTH: 409
<212> TYPE: DNA
<213> ORGANISM: Babesia microti

<400> SEQUENCE: 59

```
tgcaggtgat accgatcgcg aagctggtgg gcctagtgga actgttgggc ctagtgaagc    60
tggtgggcct agtgaagctg gtgggcctag tgaagctggt gggcctagtg aagctggtgg   120
gcctagtgaa gctggtgggc ctagtgaagc tggtgggcct agtgaagctg gtgggcctag   180
tgaagctggt gggcctagtg aagctggtgg gcctagtgaa gctggttggc ctagtgaagc   240
tggttggcct agtgaagctg gtgggcctag tggaactggt tggcctagtg aagctggttg   300
gcctagtgaa gctggttggc ctagtgaagc tggttggcct agtgaagctg gttggcctag   360
tgaacgattt ggatatcagc ttctttggta ttctagaaga atagttata                409
```

<210> SEQ ID NO 60
<211> LENGTH: 351
<212> TYPE: DNA
<213> ORGANISM: Babesia microti

<400> SEQUENCE: 60

```
gtgaagctgg tgggcctagt ggaactgttg ggcctagtga agctggtggg cctagtgaag    60
ctggtgggcc tagtgaagct ggtgggccta gtgaagctgt gggcctagt gaagctggtg   120
ggcctagtga agctggtggg cctagtgaag ctggtgggcc tagtgaagct ggtgggccta   180
gtgaagctgg tgggcctagt gaagctggtt ggcctagtga agctggttgg cctagtgaag   240
ctggtgggcc tagtggaact ggttggccta gtgaagctgg ttggcctagt gaagctggtt   300
ggcctagtga agctggttgg cctagtgaag ctggttggcc tagtgaacga t             351
```

<210> SEQ ID NO 61
<211> LENGTH: 410
<212> TYPE: DNA
<213> ORGANISM: Babesia microti

<400> SEQUENCE: 61

```
aggtgatacc gatcgcgaag ctggtgggcc tagtggaact gttgggccta gtgaagctgg    60
tgggcctagt gaagctggtg ggcctagtga agctggtggg cctagtgaag ctggtgggcc   120
tagtgaagct ggtgggccta gtgaagctgg tgggcctagt gaagctggtg ggcctagtga   180
```

-continued

| | |
|---|---|
| agctggtggg cctagtgaag ctggtgggcc tagtgaagct ggtgggccta gtgaagctgg | 240 |
| ttggcctagt gaagctggtt ggcctagtga agctggtggg cctagtggaa ctggttggcc | 300 |
| tagtgaagct ggttggccta gtgaagctgg ttggcctagt gaagctggtt ggcctagtga | 360 |
| agctggttgg cctagtgaac gatttggata tcagcttctt tggtattcta | 410 |

<210> SEQ ID NO 62
<211> LENGTH: 416
<212> TYPE: DNA
<213> ORGANISM: Babesia microti

<400> SEQUENCE: 62

| | |
|---|---|
| ttgcaggtga taccgatcgc gaagctggtg ggcctagtgg aactgttggg cctagtgaag | 60 |
| ctggtgggcc tagtgaagct ggtgggccta gtgaagctgg tgggcctagt gaagctggtg | 120 |
| ggcctagtga agctggtggg cctagtgaag ctggtgggcc tagtgaagct ggtgggccta | 180 |
| gtgaagctgg tgggcctagt gaagctggtg ggcctagtga agctggtggg cctagtgaag | 240 |
| ctggtgggcc tagtgaagct ggttggccta gtgaagctgg ttggcctagt gaagctggtg | 300 |
| ggcctagtgg aactggttgg cctagtgaag ctggttggcc tagtgaagct ggttggccta | 360 |
| gtgaagctgg ttggcctagt gaagctggtt ggcctagtga acgatttgga tatcag | 416 |

<210> SEQ ID NO 63
<211> LENGTH: 356
<212> TYPE: DNA
<213> ORGANISM: Babesia microti

<400> SEQUENCE: 63

| | |
|---|---|
| ttgcaggtga taccgatcgc gaagctggtg ggcctagtgg aactgttggg cctagtgaag | 60 |
| ctggtgggcc tagtgaagct ggtgggccta gtgaagctgg tgggcctagt gaagctggtg | 120 |
| ggcctagtga agctggtggg cctagtgaag ctggtgggcc tagtgaagct ggtgggccta | 180 |
| gtgaagctgg tgggcctagt ggaactggtt ggcctagtga agctggttgg cctagtgaag | 240 |
| ctggttggcc tagtgaagct ggttggccta gtgaagctgg ttggcctagt gaagctggtt | 300 |
| ggcctagtga acgatttgga tatcagcttc tttggtattc tagaagaata gttata | 356 |

<210> SEQ ID NO 64
<211> LENGTH: 285
<212> TYPE: DNA
<213> ORGANISM: Babesia microti

<400> SEQUENCE: 64

| | |
|---|---|
| ttgcaggtga taccgatcgc gaagctggtg ggcctagtgg aactgttggg cctagtgaag | 60 |
| ctggtgggcc tagtgaagct ggtgggccta gtgaagctgg tgggcctagt gaagctggtg | 120 |
| ggcctagtga agctggtggg cctagtgaag ctggtgggcc tagtgaagct ggtgggccta | 180 |
| gtggaactgg ttggcctagt gaagctggtt ggcctagtga agctggttgg cctagtgaag | 240 |
| ctggttggcc tagtgaagct ggttggccta gtgaagctgg ttggc | 285 |

<210> SEQ ID NO 65
<211> LENGTH: 342
<212> TYPE: DNA
<213> ORGANISM: Babesia microti

<400> SEQUENCE: 65

| | |
|---|---|
| ttgcaggtga taccgatcgc gaagctggtg ggcctagtgg aactgttggg cctagtgaag | 60 |
| ctggtgggcc tagtgaagct ggtgggccta gtgaagctgg tgggcctagt gaagctggtg | 120 |

```
ggcctagtga agctggtggg cctagtgaag ctggtgggcc tagtgaagct ggtgggccta    180
gtgaagctgg tgggcctagt ggaactggtt ggcctagtga agctggttgg cctagtgaag    240
ctggttggcc tagtgaagct ggttggccta gtgaagctgg ttggcctagt gaagctggtt    300
ggcctagtga acgatttgga tatcagcttc tttggtattc ta                       342
```

<210> SEQ ID NO 66
<211> LENGTH: 363
<212> TYPE: DNA
<213> ORGANISM: Babesia microti

<400> SEQUENCE: 66

```
ttgcaggtga taccgatcgc gaagctggtg ggcctagtgg aactgttggg cctagtgaag     60
ctggtgggcc tagtgaagct ggtgggccta gtgaagctgg tgggcctagt gaagctggtg    120
ggcctagtga agctggtggg cctagtgaag ctggtgggcc tagtgaagct ggtgggccta    180
gtgaagctgg tgggcctagt gaagctggtg ggcctagtgg aactggttgg cctagtgaag    240
ctggttggcc tagtgaagct ggttggccta gtgaagctgg ttggcctagt gaagctggtt    300
ggcctagtga agctggttgg cctagtgaac gatttggata tcagcttctt tggtattcta    360
gaa                                                                  363
```

<210> SEQ ID NO 67
<211> LENGTH: 363
<212> TYPE: DNA
<213> ORGANISM: Babesia microti

<400> SEQUENCE: 67

```
ttgcaggtga taccgatcgc gaagctggtg ggcctagtgg aactgttggg cctagtgaag     60
ctggtgggcc tagtgaagct ggtgggccta gtgaagctgg tgggcctagt gaagctggtg    120
ggcctagtga agctggtggg cctagtgaag ctggtgggcc tagtgaagct ggtgggccta    180
gtgaagctgg tgggcctagt gaagctggtg ggcctagtgg aactggttgg cctagtgaag    240
ctggttggcc tagtgaagct ggttggccta gtgaagctgg ttggcctagt gaagctggtt    300
ggcctagtga agctggttgg cctagtgaac gatttggata tcagcttctt tggtattcta    360
gaa                                                                  363
```

<210> SEQ ID NO 68
<211> LENGTH: 101
<212> TYPE: PRT
<213> ORGANISM: Babesia microti

<400> SEQUENCE: 68

```
Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Gly Thr
                20                  25                  30

Val Gly Pro Ser Glu Ala Gly Gly Pro Ser Glu Ala Gly Gly Pro Ser
            35                  40                  45

Gly Thr Gly Trp Pro Ser Glu Ala Gly Gly Pro Ser Gly Thr Val Gly
        50                  55                  60

Pro Ser Glu Ala Gly Gly Pro Ser Glu Ala Gly Gly Pro Ser Gly Thr
65                  70                  75                  80

Gly Trp Pro Ser Gly Thr Gly Trp Pro Ser Glu Val Gly Trp Pro Ile
                85                  90                  95
```

-continued

```
Glu Pro Phe Gly Tyr
            100

<210> SEQ ID NO 69
<211> LENGTH: 105
<212> TYPE: PRT
<213> ORGANISM: Babesia microti

<400> SEQUENCE: 69

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Gly Thr
            20                  25                  30

Val Gly Pro Ser Glu Ala Gly Gly Pro Ser Glu Ala Gly Gly Pro Ser
        35                  40                  45

Gly Thr Gly Trp Pro Ser Glu Ala Gly Gly Pro Ser Gly Thr Val Gly
     50                  55                  60

Pro Ser Glu Ala Gly Gly Pro Ser Glu Ala Gly Gly Pro Ser Gly Thr
65                  70                  75                  80

Gly Trp Pro Ser Gly Thr Gly Trp Pro Ser Glu Val Gly Trp Pro Asn
                85                  90                  95

Glu Pro Phe Gly Tyr His Leu Leu Trp
            100                 105

<210> SEQ ID NO 70
<211> LENGTH: 118
<212> TYPE: PRT
<213> ORGANISM: Babesia microti

<400> SEQUENCE: 70

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
     50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
                85                  90                  95

Glu Ala Gly Trp Pro Ser Glu Ala Gly Trp Pro Ser Glu Ala Gly Trp
            100                 105                 110

Pro Ser Glu Ala Gly Trp
        115

<210> SEQ ID NO 71
<211> LENGTH: 136
<212> TYPE: PRT
<213> ORGANISM: Babesia microti

<400> SEQUENCE: 71

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
```

```
                35                  40                  45
Glu Ala Gly Gly Pro Ser Glu Ala Gly Gly Pro Ser Glu Ala Gly Gly
        50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
                85                  90                  95

Glu Ala Gly Trp Pro Ser Glu Ala Gly Trp Pro Ser Glu Ala Gly Trp
                100                 105                 110

Pro Ser Glu Ala Gly Trp Pro Ser Glu Arg Phe Gly Tyr Gln Leu Leu
                115                 120                 125

Trp Tyr Ser Arg Arg Ile Val Ile
                130                 135

<210> SEQ ID NO 72
<211> LENGTH: 116
<212> TYPE: PRT
<213> ORGANISM: Babesia microti

<400> SEQUENCE: 72

Glu Ala Gly Gly Pro Ser Gly Thr Val Gly Pro Ser Glu Ala Gly Gly
1               5                   10                  15

Pro Ser Glu Ala Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
                35                  40                  45

Glu Ala Gly Gly Pro Ser Glu Ala Gly Gly Pro Ser Glu Ala Gly Gly
        50                  55                  60

Pro Ser Glu Ala Gly Trp Pro Ser Glu Ala Gly Trp Pro Ser Glu Ala
65                  70                  75                  80

Gly Gly Pro Ser Gly Thr Gly Trp Pro Ser Glu Ala Gly Trp Pro Ser
                85                  90                  95

Glu Ala Gly Trp Pro Ser Glu Ala Gly Trp Pro Ser Glu Ala Gly Trp
                100                 105                 110

Pro Ser Glu Arg
        115

<210> SEQ ID NO 73
<211> LENGTH: 136
<212> TYPE: PRT
<213> ORGANISM: Babesia microti

<400> SEQUENCE: 73

Gly Asp Thr Asp Arg Glu Ala Gly Gly Pro Ser Gly Thr Val Gly Pro
1               5                   10                  15

Ser Glu Ala Gly Gly Pro Ser Glu Ala Gly Gly Pro Ser Glu Ala Gly
                20                  25                  30

Gly Pro Ser Glu Ala Gly Pro Ser Glu Ala Gly Gly Pro Ser Glu
                35                  40                  45

Ala Gly Gly Pro Ser Glu Ala Gly Pro Ser Glu Ala Gly Gly Pro
        50                  55                  60

Ser Glu Ala Gly Gly Pro Ser Glu Ala Gly Pro Ser Glu Ala Gly
65                  70                  75                  80

Trp Pro Ser Glu Ala Gly Trp Pro Ser Glu Ala Gly Gly Pro Ser Gly
                85                  90                  95

Thr Gly Trp Pro Ser Glu Ala Gly Trp Pro Ser Glu Ala Gly Trp Pro
```

```
                    100                 105                 110
Ser Glu Ala Gly Trp Pro Ser Glu Ala Gly Trp Pro Ser Glu Arg Phe
            115                 120                 125

Gly Tyr Gln Leu Leu Trp Tyr Ser
        130                 135

<210> SEQ ID NO 74
<211> LENGTH: 138
<212> TYPE: PRT
<213> ORGANISM: Babesia microti

<400> SEQUENCE: 74

Ala Gly Asp Thr Asp Arg Glu Ala Gly Gly Pro Ser Gly Thr Val Gly
  1               5                  10                  15

Pro Ser Glu Ala Gly Gly Pro Ser Glu Ala Gly Gly Pro Ser Glu Ala
             20                  25                  30

Gly Gly Pro Ser Glu Ala Gly Gly Pro Ser Glu Ala Gly Gly Pro Ser
         35                  40                  45

Glu Ala Gly Gly Pro Ser Glu Ala Gly Gly Pro Ser Glu Ala Gly Gly
     50                  55                  60

Pro Ser Glu Ala Gly Gly Pro Ser Glu Ala Gly Gly Pro Ser Glu Ala
 65                  70                  75                  80

Gly Gly Pro Ser Glu Ala Gly Trp Pro Ser Glu Ala Gly Trp Pro Ser
                 85                  90                  95

Glu Ala Gly Gly Pro Ser Gly Thr Gly Trp Pro Ser Glu Ala Gly Trp
                100                 105                 110

Pro Ser Glu Ala Gly Trp Pro Ser Glu Ala Gly Trp Pro Ser Glu Ala
            115                 120                 125

Gly Trp Pro Ser Glu Arg Phe Gly Tyr Gln
        130                 135

<210> SEQ ID NO 75
<211> LENGTH: 118
<212> TYPE: PRT
<213> ORGANISM: Babesia microti

<400> SEQUENCE: 75

Ala Gly Asp Thr Asp Arg Glu Ala Gly Gly Pro Ser Gly Thr Val Gly
  1               5                  10                  15

Pro Ser Glu Ala Gly Gly Pro Ser Glu Ala Gly Gly Pro Ser Glu Ala
             20                  25                  30

Gly Gly Pro Ser Glu Ala Gly Gly Pro Ser Glu Ala Gly Gly Pro Ser
         35                  40                  45

Glu Ala Gly Gly Pro Ser Glu Ala Gly Gly Pro Ser Glu Ala Gly Gly
     50                  55                  60

Pro Ser Gly Thr Gly Trp Pro Ser Glu Ala Gly Trp Pro Ser Glu Ala
 65                  70                  75                  80

Gly Trp Pro Ser Glu Ala Gly Trp Pro Ser Glu Ala Gly Trp Pro Ser
                 85                  90                  95

Glu Ala Gly Trp Pro Ser Glu Arg Phe Gly Tyr Gln Leu Leu Trp Tyr
                100                 105                 110

Ser Arg Arg Ile Val Ile
            115

<210> SEQ ID NO 76
<211> LENGTH: 94
<212> TYPE: PRT
```

-continued

<213> ORGANISM: Babesia microti

<400> SEQUENCE: 76

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Gly Thr Gly Trp
        50                  55                  60

Pro Ser Glu Ala Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp
                85                  90

<210> SEQ ID NO 77
<211> LENGTH: 113
<212> TYPE: PRT
<213> ORGANISM: Babesia microti

<400> SEQUENCE: 77

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Glu Ala Gly Gly
        50                  55                  60

Pro Ser Gly Thr Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Arg Phe Gly Tyr Gln Leu Leu Trp Tyr
            100                 105                 110

Ser

<210> SEQ ID NO 78
<211> LENGTH: 120
<212> TYPE: PRT
<213> ORGANISM: Babesia microti

<400> SEQUENCE: 78

Ala Gly Asp Thr Asp Arg Glu Ala Gly Gly Pro Ser Gly Thr Val Gly
1 5 10 15

Pro Ser Glu Ala Gly Gly Pro Ser Glu Ala Gly Gly Pro Ser Glu Ala
20 25 30

Gly Gly Pro Ser Glu Ala Gly Gly Pro Ser Glu Ala Gly Gly Pro Ser
35 40 45

Glu Ala Gly Gly Pro Ser Glu Ala Gly Gly Pro Ser Glu Ala Gly Gly
50 55 60

Pro Ser Glu Ala Gly Gly Pro Ser Gly Thr Gly Trp Pro Ser Glu Ala
65 70 75 80

Gly Trp Pro Ser Glu Ala Gly Trp Pro Ser Glu Ala Gly Trp Pro Ser
85 90 95

```
Glu Ala Gly Trp Pro Ser Glu Ala Gly Trp Pro Ser Glu Arg Phe Gly
            100                 105                 110
Tyr Gln Leu Leu Trp Tyr Ser Arg
        115                 120

<210> SEQ ID NO 79
<211> LENGTH: 120
<212> TYPE: PRT
<213> ORGANISM: Babesia microti

<400> SEQUENCE: 79

Ala Gly Asp Thr Asp Arg Glu Ala Gly Gly Pro Ser Gly Thr Val Gly
  1               5                  10                  15
Pro Ser Glu Ala Gly Gly Pro Ser Glu Ala Gly Gly Pro Ser Glu Ala
             20                  25                  30
Gly Gly Pro Ser Glu Ala Gly Gly Pro Ser Glu Ala Gly Gly Pro Ser
         35                  40                  45
Glu Ala Gly Gly Pro Ser Glu Ala Gly Gly Pro Ser Glu Ala Gly Gly
     50                  55                  60
Pro Ser Glu Ala Gly Gly Pro Ser Gly Thr Gly Trp Pro Ser Glu Ala
 65                  70                  75                  80
Gly Trp Pro Ser Glu Ala Gly Trp Pro Ser Glu Ala Gly Trp Pro Ser
                 85                  90                  95
Glu Ala Gly Trp Pro Ser Glu Ala Gly Trp Pro Ser Glu Arg Phe Gly
            100                 105                 110
Tyr Gln Leu Leu Trp Tyr Ser Arg
        115                 120

<210> SEQ ID NO 80
<211> LENGTH: 29
<212> TYPE: DNA
<213> ORGANISM: Artificial Sequence
<220> FEATURE:
<223> OTHER INFORMATION: PCR Primer

<400> SEQUENCE: 80
cagagcagta ctgatgatat taagaaggc                                    29

<210> SEQ ID NO 81
<211> LENGTH: 43
<212> TYPE: DNA
<213> ORGANISM: Artificial Sequence
<220> FEATURE:
<223> OTHER INFORMATION: PCR Primer

<400> SEQUENCE: 81
caatatgaat tcagtgaata tttacaataa atgttaataa tgc                    43

<210> SEQ ID NO 82
<211> LENGTH: 32
<212> TYPE: DNA
<213> ORGANISM: Artificial Sequence
<220> FEATURE:
<223> OTHER INFORMATION: PCR Primer

<400> SEQUENCE: 82
cataacaata ttccagaacc caatgcggat tc                                32

<210> SEQ ID NO 83
<211> LENGTH: 32
<212> TYPE: DNA
<213> ORGANISM: Artificial Sequence
```

```
<220> FEATURE:
<223> OTHER INFORMATION: PCR Primer

<400> SEQUENCE: 83
cgctagaatt cattagaaag ccttaaacat gc                                    32

<210> SEQ ID NO 84
<211> LENGTH: 2001
<212> TYPE: DNA
<213> ORGANISM: Babesia

<400> SEQUENCE: 84
atgcagcatc accaccatca ccacactgat gatattaaga aggcatttga cgaatgcaaa      60
tctaatgcta ttatattgaa gaaaagata cttgacaatg atgaagatta taagattaat     120
tttagggaaa tggtgaatga agtaacatgt gcaaacacaa aatttgaagc cctaaatgat     180
ttgataattt ccgactgtga gaaaaaggt attaagataa acagagatgt gatttcaagc     240
tacaaattgc ttctttccac aatcacctat attgttggag ctggagttga agctgtaact    300
gttagtgtgt ctgctacatc taatggaact gaatctggtg gagctggtag tggaactgga    360
actagtgtgt ctgctacatc tactttaact ggtaatggtg gaactgaatc tggtggaaca    420
gctggaacta ctacgtctag tggaactgaa gctggtggaa ctagtggaac tactacgtct    480
agtggagctg ctagtggtaa agctggaact ggaacagctg gaactactac gtctagtgaa    540
ggtgctggta gtgataaagc tggaactgga actagtggaa ctactacgtc tagtggaact    600
ggtgctggtg gagctggtag tggtggacct agtggacatg cttctaatgc aaaaattcct    660
ggaataatga cactaactct atttgcatta ttaacattta ttgtaaatat tccagaaccc    720
aatgcggatt cagaatctgt acatgttgaa atccaggaac atgataacat caatccacaa    780
gacgcttgcg atagtgagcc gctcgaacaa atggattctg ataccagggt gttgcccgaa    840
agtttggatg aggggtacc acaccaattc tctagattag ggcaccactc agacatggca    900
tctgatataa atgatgaaga accatcattt aaaatcggcg agaatgacat aattcaacca    960
ccctgggaag atacagctcc ataccattca atagatgatg aagagcttga caacttaatg   1020
agactaacgg cgcaagaaac aagtgacgat catgaagaag ggaatggcaa actcaatacg   1080
aataaaagtg agaagactga agaaaatcg catgatactc agacaccgca agaaatatat   1140
gaagagcttg acaacttact gagactaacg gcacaagaaa tatatgaaga gcgtaaagaa   1200
gggcatggca aacccaatac gaataaaagt gagaaggctg aaagaaaatc gcatgatact   1260
cagacaacgc aagaaatatg tgaagagtgt gaagaagggc atgacaaaat caataagaat   1320
aaaagtggaa atgctggaat aaaatcgtat gatactcaga caacgcaaga aatatgtgaa   1380
gagtgtgaag aagggcatga caaaatcaat aagaataaaa gtggaaatgc tggaataaaa   1440
tcgtatgata ctcagacacc gcaggaaaca agtgacgctc atgaagaagg gcatgacaaa   1500
atcaatacga ataaaagtga gaaggctgaa agaaatcgc atgatactca gacaacgcaa   1560
gaaatatgtg aagagtgtga agaagggcat gacaaaatca ataagaataa agtggaaat   1620
gctggaataa aatcgtatga tactcagaca ccgcaggaaa caagtgacgc tcatgaagaa   1680
gagcatggca atctcaataa gaataaaagt gggaaggctg aataaaatc gcataatact   1740
cagacaccgc tgaaaaaaaa agacttttgt aaagaagggt gtcatggttg caataataag   1800
cccgaggata atgaaagaga cccgtcgtcg cctgatgatg atggtggctg cgaatgcggc   1860
atgacgaatc actttgtctt tgactacaag acaacactct tgttaaagag cctcaagact   1920
```
gaaacatcca ctcattatta cattgccatg gctgcaattt ttactatttc attattccca  1980
tgcatgttta aggctttctg a  2001

<210> SEQ ID NO 85
<211> LENGTH: 666
<212> TYPE: PRT
<213> ORGANISM: Babesia

<400> SEQUENCE: 85

Met Gln His His His His His Thr Asp Asp Ile Lys Lys Ala Phe
              5                  10                  15

Asp Glu Cys Lys Ser Asn Ala Ile Ile Leu Lys Lys Ile Leu Asp
             20                  25                  30

Asn Asp Glu Asp Tyr Lys Ile Asn Phe Arg Glu Met Val Asn Glu Val
             35                  40                  45

Thr Cys Ala Asn Thr Lys Phe Glu Ala Leu Asn Asp Leu Ile Ile Ser
         50                  55                  60

Asp Cys Glu Lys Lys Gly Ile Lys Ile Asn Arg Asp Val Ile Ser Ser
65                  70                  75                  80

Tyr Lys Leu Leu Leu Ser Thr Ile Thr Tyr Ile Val Gly Ala Gly Val
                 85                  90                  95

Glu Ala Val Thr Val Ser Val Ser Ala Thr Ser Asn Gly Thr Glu Ser
            100                 105                 110

Gly Gly Ala Gly Ser Gly Thr Gly Thr Ser Val Ser Ala Thr Ser Thr
        115                 120                 125

Leu Thr Gly Asn Gly Gly Thr Glu Ser Gly Gly Thr Ala Gly Thr Thr
    130                 135                 140

Thr Ser Ser Gly Thr Glu Ala Gly Gly Thr Ser Gly Thr Thr Thr Ser
145                 150                 155                 160

Ser Gly Ala Ala Ser Gly Lys Ala Gly Thr Gly Thr Ala Gly Thr Thr
                165                 170                 175

Thr Ser Ser Glu Gly Ala Gly Ser Asp Lys Ala Gly Thr Gly Thr Ser
            180                 185                 190

Gly Thr Thr Thr Ser Ser Gly Thr Gly Ala Gly Gly Ala Gly Ser Gly
        195                 200                 205

Gly Pro Ser Gly His Ala Ser Asn Ala Lys Ile Pro Gly Ile Met Thr
    210                 215                 220

Leu Thr Leu Phe Ala Leu Leu Thr Phe Ile Val Asn Ile Pro Glu Pro
225                 230                 235                 240

Asn Ala Asp Ser Glu Ser Val His Val Glu Ile Gln Glu His Asp Asn
                245                 250                 255

Ile Asn Pro Gln Asp Ala Cys Asp Ser Glu Pro Leu Glu Gln Met Asp
            260                 265                 270

Ser Asp Thr Arg Val Leu Pro Glu Ser Leu Asp Glu Gly Val Pro His
        275                 280                 285

Gln Phe Ser Arg Leu Gly His His Ser Asp Met Ala Ser Asp Ile Asn
    290                 295                 300

Asp Glu Glu Pro Ser Phe Lys Ile Gly Glu Asn Asp Ile Ile Gln Pro
305                 310                 315                 320

Pro Trp Glu Asp Thr Ala Pro Tyr His Ser Ile Asp Asp Glu Glu Leu
                325                 330                 335

Asp Asn Leu Met Arg Leu Thr Ala Gln Glu Thr Ser Asp Asp His Glu
            340                 345                 350

Glu Gly Asn Gly Lys Leu Asn Thr Asn Lys Ser Glu Lys Thr Glu Arg

```
              355                 360                 365
Lys Ser His Asp Thr Gln Thr Pro Gln Glu Ile Tyr Glu Glu Leu Asp
        370                 375                 380

Asn Leu Leu Arg Leu Thr Ala Gln Glu Ile Tyr Glu Glu Arg Lys Glu
385                 390                 395                 400

Gly His Gly Lys Pro Asn Thr Asn Lys Ser Glu Lys Ala Glu Arg Lys
                405                 410                 415

Ser His Asp Thr Gln Thr Thr Gln Glu Ile Cys Glu Glu Cys Glu Glu
                420                 425                 430

Gly His Asp Lys Ile Asn Lys Asn Lys Ser Gly Asn Ala Gly Ile Lys
            435                 440                 445

Ser Tyr Asp Thr Gln Thr Thr Gln Glu Ile Cys Glu Glu Cys Glu Glu
        450                 455                 460

Gly His Asp Lys Ile Asn Lys Asn Lys Ser Gly Asn Ala Gly Ile Lys
465                 470                 475                 480

Ser Tyr Asp Thr Gln Thr Pro Gln Glu Thr Ser Asp Ala His Glu Glu
                485                 490                 495

Gly His Asp Lys Ile Asn Thr Asn Lys Ser Glu Lys Ala Glu Arg Lys
                500                 505                 510

Ser His Asp Thr Gln Thr Thr Gln Glu Ile Cys Glu Glu Cys Glu Glu
            515                 520                 525

Gly His Asp Lys Ile Asn Lys Asn Lys Ser Gly Asn Ala Gly Ile Lys
        530                 535                 540

Ser Tyr Asp Thr Gln Thr Pro Gln Glu Thr Ser Asp Ala His Glu Glu
545                 550                 555                 560

Glu His Gly Asn Leu Asn Lys Asn Lys Ser Gly Lys Ala Gly Ile Lys
                565                 570                 575

Ser His Asn Thr Gln Thr Pro Leu Lys Lys Lys Asp Phe Cys Lys Glu
                580                 585                 590

Gly Cys His Gly Cys Asn Asn Lys Pro Glu Asp Asn Glu Arg Asp Pro
            595                 600                 605

Ser Ser Pro Asp Asp Asp Gly Gly Cys Glu Cys Gly Met Thr Asn His
        610                 615                 620

Phe Val Phe Asp Tyr Lys Thr Thr Leu Leu Leu Lys Ser Leu Lys Thr
625                 630                 635                 640

Glu Thr Ser Thr His Tyr Tyr Ile Ala Met Ala Ala Ile Phe Thr Ile
                645                 650                 655

Ser Leu Phe Pro Cys Met Phe Lys Ala Phe
                660                 665

<210> SEQ ID NO 86
<211> LENGTH: 3402
<212> TYPE: DNA
<213> ORGANISM: Babesia

<400> SEQUENCE: 86
atgcagcatc accaccatca ccacttgact tttggaaata tacgttttca taatataaat      60
ctcccaccat tttcattggg cataattcac tcgattacgg tagaaaaggc gattaactct     120
gaagattttg acgaataca aacacttta caagtgtcta tcattgctag ttacggtcca       180
tctggcgatt acagtagttt tgtgttcact ccagttgtaa cagcagacac caacgttttt     240
tacaaattag agacggattt caaacttgat gttgatgtta ttactaagac atcactagaa     300
ttgcccacaa gtgttcctgg ctttcactac accgaaacta tttaccaagg cacagaattg     360
```

-continued

```
tcaaaatttta gcaagcctca gtgcaaactt aacgatcctc ctattacaac aggatcgggg      420
ttgcaaataa tacatgatgg tttgaataat tcgacaatta taaccaacaa agaagttaat      480
gtggatggaa cagatttagt ttttttttgaa ttgctccctc catcggatgg cattcccacc     540
ttgcgatcaa aattatttcc cgtcctgaaa tcaattccaa tgatatctac cggggttaat     600
gaattactgt tggaagtact cgagaacccc tctttcccta gtgcaattag caattacacc     660
ggactgacag gccgacttaa caaattactt acagttttag acggtattgt tgatagcgcc      720
attagtgtca agactacaga aactgtccct gacgacgcag aaacttctat ttcttcattg      780
aaatcattga taaaggcaat acgagataat attactacca ctcgaaacga agttaccaaa     840
gatgatgttt atgcattgaa gaaggccctc acttgtctaa cgacacacct aatatatcat      900
tcaaaagtag atggtatatc attcgacatg ctgggaacac aaaaaaataa atctagccca     960
ctaggcaaga tcggaacgtc tatggacgat attatagcca tgttttcgaa tcccaatatg    1020
tatcttgtga aggtggcgta cttgcaagcc attgaacaca ttttttctcat atcaaccaaa   1080 tacaatgata tatttgatta caccattgat tttagtaagc gtgaagctac tgattctgga    1140
tcatttaccg atatattgct cggaaacaag gtgaaggaat ctttgtcatt tattgagggt    1200
ttgatttctg acataaaatc tcactcattg aaagctgggg ttacaggagg tatatcaagt    1260
tcatcattat ttgatgaaat cttcgacgag ttaaatttgg atcaagcaac aattagaacc    1320
cttgttgcac cattagattg gccacttatc tcagacaaaa gcctccaccc ttcactgaag    1380
atggttgtgg tcctgccagg attttttcata gttcctggat ccactgatga tattaagaag    1440
gcatttgacg aatgcaaatc taatgctatt atattgaaga aaaagatact tgacaatgat    1500
gaagattata agattaattt tagggaaatg gtgaatgaag taacatgtgc aaacacaaaa    1560
tttgaagccc taaatgattt gataatttcc gactgtgaga aaaaaggtat taagataaac    1620
agagatgtga tttcaagcta caaattgctt ctttccacaa tcacctatat tgttggagct    1680
ggagttgaag ctgtaactgt tagtgtgtct gctacatcta atggaactga atctggtgga    1740
gctggtagtg gaactggaac tagtgtgtct gctacatcta ctttaactgg taatggtgga    1800
actgaatctg gtggaacagc tggaactact acgtctagtg gaactgaagc tggtggaact    1860
agtgaactac tacgtctag tggagctgct agtggtaaag ctggaactgg aacagctgga    1920
actactacgt ctagtgaagg tgctggtagt gataaagctg gaactggaac tagtggaact    1980
actacgtcta gtgaactgg tgctggtgga gctggtagtg gtggacctag tggacatgct    2040
tctaatgcaa aaattcctgg aataatgaca ctaactctat ttgcattatt aacatttatt    2100
gtaaatattc cagaacccaa tgcggattca gaatctgtac atgttgaaat ccaggaacat    2160
gataacatca atccacaaga cgcttgcgat agtgagccgc tcgaacaaat ggattctgat    2220
accagggtgt gcccgaaaag tttggatgag ggggtaccac accaattctc tagattaggg    2280
caccactcag acatggcatc tgatataaat gatgaagaac catcatttaa aatcggcgag    2340
aatgacataa ttcaaccacc ctgggaagat acagctccat accattcaat agatgatgaa    2400
gagcttgaca acttaatgag actaacggcg caagaaacaa gtgacgatca tgaagaaggg    2460
aatggcaaac tcaatacgaa taaaagtgag aagactgaaa gaaaatcgca tgatactcag    2520
acaccgcaag aaatatatga agagcttgac aacttactga gactaacggc acaagaaata    2580
tatgaagagc gtaaagaagg gcatggcaaa cccaatacga ataaaagtga aaggctgaa     2640 agaaaatcgc atgatactca gacaacgcaa gaaatatgtg aagagtgtga agaagggcat    2700 gacaaaaatca ataagaataa aagtggaaat gctggaataa aatcgtatga tactcagaca    2760
```

-continued

```
acgcaagaaa tatgtgaaga gtgtgaagaa gggcatgaca aaatcaataa gaataaaagt    2820
ggaaatgctg gaataaaatc gtatgatact cagacaccgc aggaaacaag tgacgctcat    2880 gaagaaggc atgacaaaat caatacgaat aaaagtgaga aggctgaaag aaaatcgcat     2940
gatactcaga caacgcaaga aatatgtgaa gagtgtgaag aagggcatga caaaatcaat    3000
aagaataaaa gtggaaatgc tggaataaaa tcgtatgata ctcagacacc gcaggaaaca    3060
agtgacgctc atgaagaaga gcatggcaat ctcaataaga ataaaagtgg aaggctgga    3120 ataaaatcgc ataatactca gacaccgctg aaaaaaaag acttttgtaa agaagggtgt     3180
catggttgca ataataagcc cgaggataat gaaagagacc cgtcgtcgcc tgatgatgat    3240
ggtggctgcg aatgcggcat gacgaatcac tttgtctttg actacaagac aacactcttg    3300
ttaaagagcc tcaagactga acatccact cattattaca ttgccatggc tgcaatttt     3360 actatttcat tattcccatg catgtttaag gctttctaat ga                        3402
```

<210> SEQ ID NO 87
<211> LENGTH: 1132
<212> TYPE: PRT
<213> ORGANISM: Babesia

<400> SEQUENCE: 87

```
Met Gln His His His His His Leu Thr Phe Gly Asn Ile Arg Phe
              5                   10                  15

His Asn Ile Asn Leu Pro Pro Phe Ser Leu Gly Ile Ile His Ser Ile
             20                  25                  30

Thr Val Glu Lys Ala Ile Asn Ser Glu Asp Phe Asp Gly Ile Gln Thr
             35                  40                  45

Leu Leu Gln Val Ser Ile Ile Ala Ser Tyr Gly Pro Ser Gly Asp Tyr
         50                  55                  60

Ser Ser Phe Val Phe Thr Pro Val Val Thr Ala Asp Thr Asn Val Phe
 65                  70                  75                  80

Tyr Lys Leu Glu Thr Asp Phe Lys Leu Asp Val Asp Ile Thr Lys
                 85                  90                  95

Thr Ser Leu Glu Leu Pro Thr Ser Val Pro Gly Phe His Tyr Thr Glu
            100                 105                 110

Thr Ile Tyr Gln Gly Thr Glu Leu Ser Lys Phe Ser Lys Pro Gln Cys
        115                 120                 125

Lys Leu Asn Asp Pro Pro Ile Thr Thr Gly Ser Gly Leu Gln Ile Ile
130                 135                 140

His Asp Gly Leu Asn Asn Ser Thr Ile Ile Thr Asn Lys Glu Val Asn
145                 150                 155                 160

Val Asp Gly Thr Asp Leu Val Phe Phe Glu Leu Leu Pro Ser Asp
                165                 170                 175

Gly Ile Pro Thr Leu Arg Ser Lys Leu Phe Pro Val Leu Lys Ser Ile
            180                 185                 190

Pro Met Ile Ser Thr Gly Val Asn Glu Leu Leu Leu Glu Val Leu Glu
        195                 200                 205

Asn Pro Ser Phe Pro Ser Ala Ile Ser Asn Tyr Thr Gly Leu Thr Gly
    210                 215                 220

Arg Leu Asn Lys Leu Leu Thr Val Leu Asp Gly Ile Val Asp Ser Ala
225                 230                 235                 240

Ile Ser Val Lys Thr Thr Glu Val Pro Asp Asp Ala Glu Thr Ser
                245                 250                 255
```

-continued

```
Ile Ser Ser Leu Lys Ser Leu Ile Lys Ala Ile Arg Asp Asn Ile Thr
            260                 265                 270
Thr Thr Arg Asn Glu Val Thr Lys Asp Asp Val Tyr Ala Leu Lys Lys
            275                 280                 285
Ala Leu Thr Cys Leu Thr Thr His Leu Ile Tyr His Ser Lys Val Asp
            290                 295                 300
Gly Ile Ser Phe Asp Met Leu Gly Thr Gln Lys Asn Lys Ser Ser Pro
305                 310                 315                 320
Leu Gly Lys Ile Gly Thr Ser Met Asp Asp Ile Ile Ala Met Phe Ser
                325                 330                 335
Asn Pro Asn Met Tyr Leu Val Lys Val Ala Tyr Leu Gln Ala Ile Glu
            340                 345                 350
His Ile Phe Leu Ile Ser Thr Lys Tyr Asn Asp Ile Phe Asp Tyr Thr
            355                 360                 365
Ile Asp Phe Ser Lys Arg Glu Ala Thr Asp Ser Gly Ser Phe Thr Asp
370                 375                 380
Ile Leu Leu Gly Asn Lys Val Lys Glu Ser Leu Ser Phe Ile Glu Gly
385                 390                 395                 400
Leu Ile Ser Asp Ile Lys Ser His Ser Leu Lys Ala Gly Val Thr Gly
                405                 410                 415
Gly Ile Ser Ser Ser Leu Phe Asp Glu Ile Phe Asp Glu Leu Asn
                420                 425                 430
Leu Asp Gln Ala Thr Ile Arg Thr Leu Val Ala Pro Leu Asp Trp Pro
            435                 440                 445
Leu Ile Ser Asp Lys Ser Leu His Pro Ser Leu Lys Met Val Val Val
            450                 455                 460
Leu Pro Gly Phe Phe Ile Val Pro Gly Ser Thr Asp Asp Ile Lys Lys
465                 470                 475                 480
Ala Phe Asp Glu Cys Lys Ser Asn Ala Ile Ile Leu Lys Lys Lys Ile
                485                 490                 495
Leu Asp Asn Asp Glu Asp Tyr Lys Ile Asn Phe Arg Glu Met Val Asn
            500                 505                 510
Glu Val Thr Cys Ala Asn Thr Lys Phe Glu Ala Leu Asn Asp Leu Ile
            515                 520                 525
Ile Ser Asp Cys Glu Lys Lys Gly Ile Lys Ile Asn Arg Asp Val Ile
            530                 535                 540
Ser Ser Tyr Lys Leu Leu Leu Ser Thr Ile Thr Tyr Ile Val Gly Ala
545                 550                 555                 560
Gly Val Glu Ala Val Thr Val Ser Val Ser Ala Thr Ser Asn Gly Thr
                565                 570                 575
Glu Ser Gly Gly Ala Gly Ser Gly Thr Gly Thr Ser Val Ser Ala Thr
            580                 585                 590
Ser Thr Leu Thr Gly Asn Gly Gly Thr Glu Ser Gly Gly Thr Ala Gly
            595                 600                 605
Thr Thr Thr Ser Ser Gly Thr Glu Ala Gly Gly Thr Ser Gly Thr Thr
            610                 615                 620
Thr Ser Ser Gly Ala Ala Ser Gly Lys Ala Gly Thr Gly Thr Ala Gly
625                 630                 635                 640
Thr Thr Thr Ser Ser Glu Gly Ala Gly Ser Asp Lys Ala Gly Thr Gly
                645                 650                 655
Thr Ser Gly Thr Thr Thr Ser Ser Gly Thr Gly Ala Gly Gly Ala Gly
            660                 665                 670
Ser Gly Gly Pro Ser Gly His Ala Ser Asn Ala Lys Ile Pro Gly Ile
```

-continued

```
                675                 680                 685
Met Thr Leu Thr Leu Phe Ala Leu Leu Thr Phe Ile Val Asn Ile Pro
    690                 695                 700
Glu Pro Asn Ala Asp Ser Glu Ser Val His Val Glu Ile Gln Glu His
705                 710                 715                 720
Asp Asn Ile Asn Pro Gln Asp Ala Cys Asp Ser Glu Pro Leu Glu Gln
                725                 730                 735
Met Asp Ser Asp Thr Arg Val Leu Pro Glu Ser Leu Asp Glu Gly Val
            740                 745                 750
Pro His Gln Phe Ser Arg Leu Gly His Ser Asp Met Ala Ser Asp
        755                 760                 765
Ile Asn Asp Glu Glu Pro Ser Phe Lys Ile Gly Glu Asn Asp Ile Ile
    770                 775                 780
Gln Pro Pro Trp Glu Asp Thr Ala Pro Tyr His Ser Ile Asp Asp Glu
785                 790                 795                 800
Glu Leu Asp Asn Leu Met Arg Leu Thr Ala Gln Glu Thr Ser Asp Asp
                805                 810                 815
His Glu Glu Gly Asn Gly Lys Leu Asn Thr Asn Lys Ser Glu Lys Thr
            820                 825                 830
Glu Arg Lys Ser His Asp Thr Gln Thr Pro Gln Glu Ile Tyr Glu Glu
        835                 840                 845
Leu Asp Asn Leu Leu Arg Leu Thr Ala Gln Glu Ile Tyr Glu Glu Arg
    850                 855                 860
Lys Glu Gly His Gly Lys Pro Asn Thr Asn Lys Ser Glu Lys Ala Glu
865                 870                 875                 880
Arg Lys Ser His Asp Thr Gln Thr Thr Gln Glu Ile Cys Glu Glu Cys
                885                 890                 895
Glu Glu Gly His Asp Lys Ile Asn Lys Asn Lys Ser Gly Asn Ala Gly
            900                 905                 910
Ile Lys Ser Tyr Asp Thr Gln Thr Thr Gln Glu Ile Cys Glu Glu Cys
        915                 920                 925
Glu Glu Gly His Asp Lys Ile Asn Lys Asn Lys Ser Gly Asn Ala Gly
    930                 935                 940
Ile Lys Ser Tyr Asp Thr Gln Thr Pro Gln Glu Thr Ser Asp Ala His
945                 950                 955                 960
Glu Glu Gly His Asp Lys Ile Asn Thr Asn Lys Ser Glu Lys Ala Glu
                965                 970                 975
Arg Lys Ser His Asp Thr Gln Thr Thr Gln Glu Ile Cys Glu Glu Cys
            980                 985                 990
Glu Glu Gly His Asp Lys Ile Asn Lys Asn Lys Ser Gly Asn Ala Gly
        995                 1000                1005
Ile Lys Ser Tyr Asp Thr Gln Thr Pro Gln Glu Thr Ser Asp Ala His
    1010                1015                1020
Glu Glu Glu His Gly Asn Leu Asn Lys Asn Lys Ser Gly Lys Ala Gly
1025                1030                1035                1040
Ile Lys Ser His Asn Thr Gln Thr Pro Leu Lys Lys Asp Phe Cys
                1045                1050                1055
Lys Glu Gly Cys His Gly Cys Asn Asn Lys Pro Glu Asp Asn Glu Arg
            1060                1065                1070
Asp Pro Ser Ser Pro Asp Asp Gly Gly Cys Glu Cys Gly Met Thr
        1075                1080                1085
Asn His Phe Val Phe Asp Tyr Lys Thr Thr Leu Leu Leu Lys Ser Leu
    1090                1095                1100
```

```
Lys Thr Glu Thr Ser Thr His Tyr Tyr Ile Ala Met Ala Ala Ile Phe
1105                1110                1115                1120

Thr Ile Ser Leu Phe Pro Cys Met Phe Lys Ala Phe
            1125                1130

<210> SEQ ID NO 88
<211> LENGTH: 29
<212> TYPE: DNA
<213> ORGANISM: Artificial Sequence
<220> FEATURE:
<223> OTHER INFORMATION: PCR Primer

<400> SEQUENCE: 88
ccgtcgcagc tgactttttgg aaatatacg                                29

<210> SEQ ID NO 89
<211> LENGTH: 36
<212> TYPE: DNA
<213> ORGANISM: Artificial Sequence
<220> FEATURE:
<223> OTHER INFORMATION: PCR Primer

<400> SEQUENCE: 89
ctagaattca taggatccag gaactatgaa aaatcc                         36

<210> SEQ ID NO 90
<211> LENGTH: 27
<212> TYPE: DNA
<213> ORGANISM: Artificial Sequence
<220> FEATURE:
<223> OTHER INFORMATION: PCR Primer

<400> SEQUENCE: 90
cgtggatcca ctgatgatat taagaag                                   27
```

What is claimed is:

1. A fusion protein comprising the amino acid sequence of SEQ ID NO:85.

2. The fusion protein of claim 1, where in the fusion protein is encoded by the nucleic acid sequence of SEQ ID NO:84.

3. A fusion protein comprising the amino acid sequence of SEQ ID NO:87.

4. The fusion protein of claim 3, wherein the fusion protein is encoded by the nucleic acid sequence of SEQ ID NO:86.

* * * * *

UNITED STATES PATENT AND TRADEMARK OFFICE
CERTIFICATE OF CORRECTION

PATENT NO.    : 6,451,315 B1
DATED         : September 17, 2002
INVENTOR(S)   : Steven G. Reed et al.

It is certified that error appears in the above-identified patent and that said Letters Patent is hereby corrected as shown below:

<u>Column 145,</u>
Lines 43-45, should read as -- The fusion protein of claim 1, wherein the fusion protein is comprising an amino acid sequence encoded by the nucleic acid sequence of SEQ ID NO:84. --

Signed and Sealed this

Twentieth Day of May, 2003

JAMES E. ROGAN
*Director of the United States Patent and Trademark Office*